United States Patent
Li et al.

(10) Patent No.: US 11,680,262 B2
(45) Date of Patent: Jun. 20, 2023

(54) METHOD FOR INDUCING EXON SKIPPING BY GENOME EDITING

(71) Applicant: KYOTO UNIVERSITY, Kyoto (JP)

(72) Inventors: Hongmei Li, Kyoto (JP); Noriko Sasakawa, Kyoto (JP); Akitsu Hotta, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 209 days.

(21) Appl. No.: 16/499,218

(22) PCT Filed: Nov. 21, 2017

(86) PCT No.: PCT/JP2017/041756
§ 371 (c)(1),
(2) Date: Sep. 27, 2019

(87) PCT Pub. No.: WO2018/179578
PCT Pub. Date: Oct. 4, 2018

(65) Prior Publication Data
US 2021/0087555 A1    Mar. 25, 2021

(30) Foreign Application Priority Data
Mar. 30, 2017   (JP) .............................. JP2017-068909

(51) Int. Cl.
*C12N 15/113*    (2010.01)
*C12N 9/22*    (2006.01)

(52) U.S. Cl.
CPC .............. *C12N 15/113* (2013.01); *C12N 9/22* (2013.01); *C12N 2310/20* (2017.05)

(58) Field of Classification Search
None
See application file for complete search history.

(56) References Cited

U.S. PATENT DOCUMENTS

| | | | | |
|---|---|---|---|---|
| 10,687,520 | B2 * | 6/2020 | Min | ..................... A61P 21/00 |
| 2011/0053975 | A1 | 3/2011 | Tazi | |
| 2012/0270925 | A1 * | 10/2012 | Wilton | ..................... A61P 21/04 |
| | | | | 536/24.5 |
| 2017/0106055 | A1 * | 4/2017 | Jantz | ..................... A61P 21/00 |
| 2018/0320197 | A1 * | 11/2018 | Gersbach | .............. C12N 15/907 |
| 2019/0048337 | A1 * | 2/2019 | Hsu | ..................... C12N 15/907 |
| 2019/0151476 | A1 * | 5/2019 | Gersbach | .............. C12N 15/907 |
| 2019/0338311 | A1 * | 11/2019 | Amoasii | ................ C12N 5/0696 |
| 2019/0364862 | A1 * | 12/2019 | Amoasii | ............. A01K 67/0278 |
| 2020/0046854 | A1 * | 2/2020 | Zhang | ..................... C12N 15/11 |
| 2020/0260698 | A1 * | 8/2020 | Kyrychenko | ...... A01K 67/0276 |

FOREIGN PATENT DOCUMENTS

| | | |
|---|---|---|
| JP | 2011-509280 A | 3/2011 |
| JP | 2016-521554 A | 7/2016 |
| JP | 2016-523560 A | 8/2016 |
| WO | WO 2014/197568 A2 | 12/2014 |
| WO | WO 2015/006294 A2 | 1/2015 |
| WO | WO 2015/105928 A1 | 7/2015 |
| WO | WO-2015138739 A2 * | 9/2015 ........... A61K 38/465 |
| WO | WO 2016/025469 A1 | 2/2016 |
| WO | WO-2019017321 A1 * | 1/2019 ............. C07K 19/00 |

OTHER PUBLICATIONS

Machine English translation of WO 2019017321, retrieved on Oct. 4, 2021, pp. 1-36 (Year: 2019).*
International Search Report, dated Feb. 20, 2018, in International Application No. PCT/JP2017/041756.
Translation of the International Preliminary Report on Patentability, dated Oct. 1, 2019, in International Application No. PCT/JP2017/041756.
Li, H.L., et al., Stem Cell Reports, vol. 4, pp. 143-154, plus Supplemental Information, 2015.
Ran, F.A., et al., Cell, vol. 154, pp. 1380-1389, 2013.
Mali, P., et al., Nature Biotechnology, vol. 31. No. 9, pp. 833-838, 2013.
Kleinstiver, B.P., et al., Nature Biotechnology, vol. 34, No. 8, pp. 869-874, plus Supplemental Information, 2016.
Kim, D., et al., Nature Biotechnology, vol. 34, No. 8, pp. 863-868, plus Supplemental Information, 2016.
Zhang, Y., et al., Scientific Advances, vol. 3, e1602814, 10 pages, 2017.
Pichavant, C., et al., Molecular Therapy, vol. 19, No. 5, pp. 830-840, 2011.
Ousterout, D.G., et al., Nature Communications, 6:6244, 13 pages, 2015.
Iyombe-Engembe, J-P,. et al., Molecular Therapy-Nucleic Acids, vol. 5, e283, 12 pages, 2016.
Xu, L., et al., Molecular Therapy, vol. 24, No. 3, pp. 564-569, 2016.
Long, C., et al., Science, vol. 351, Issue 6271, pp. 400-403, 2016.
Nelson, C.E., et al., Science, vol. 351, Issue 6271, pp. 403-407, 2016.
Tabebordbar, M., et al., Science, vol. 351, Issue 6271, pp. 407-411, 2016.
Mah, J.K., Current and emerging treatment strategies for Duchenne muscular dystrophy, Neuropsychiatric Disease and Treatment, vol. 12, pp. 1795-1807, 2016.
Partial Supplementary European Search Report dated Dec. 18, 2020 in European Application No. 17904337.7.

(Continued)

*Primary Examiner* — Brian Whiteman
(74) *Attorney, Agent, or Firm* — Leydig, Voit & Mayer, Ltd.

(57) ABSTRACT

A method of skipping a target exon of a gene of interest in a genome uses CRISPR-Cas and guide RNA. The guide RNA contains a spacer sequence such that the site of cleavage by the CRISPR-Cas is positioned within 80 bases from the splice donor site immediately before the target exon or the splice acceptor site immediately after the target exon.

9 Claims, 20 Drawing Sheets

Specification includes a Sequence Listing.

(56) References Cited

OTHER PUBLICATIONS

Gee et al., "Extracellular nanovesicles for packaging of CRISPR-Cas9 protein and sgRNA to induce therapeutic exon skipping," *Nature Communications*, 11: 1334 (2020).
Japan Patent Office, Decision of Refusal in Japanese Patent Application No. 2019-508550 (dated Jan. 10, 2023).

* cited by examiner

Luc2 +Int cDNA    Pseudo-splicing donor sequence (31st base in Fig. 6)

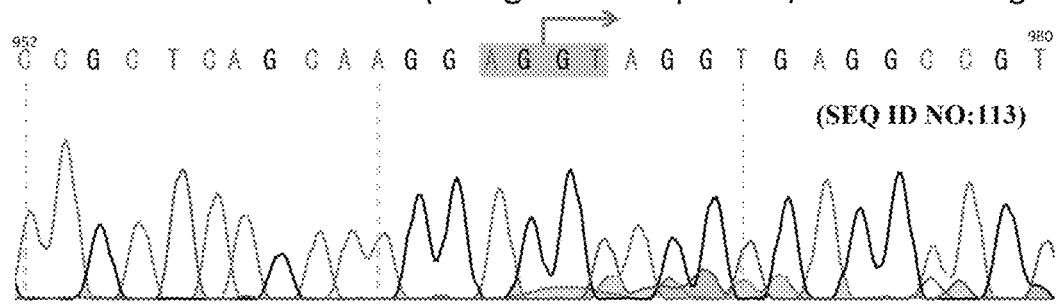

(SEQ ID NO:113)

(b)

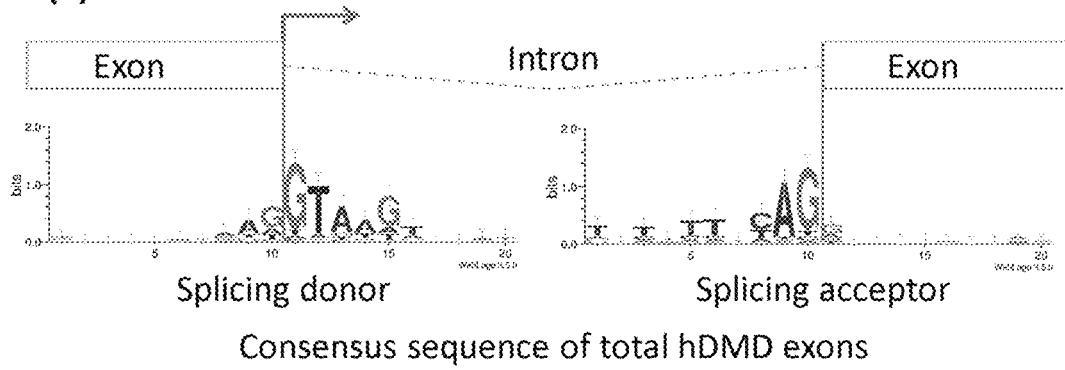

Consensus sequence of total hDMD exons (c)

```
                    Pseudo-splicing donor sequence
Original Luc:  AAGGAGGTAGGTGAG    (SEQ ID NO:114)
               LysGluValGlyGlu    (SEQ ID NO:115)

Modified Luc:  AAGGAGATAGGTGAG    (SEQ ID NO:116)
               LysGluIleGlyGlu    (SEQ ID NO:117)
```

G, which is most important for the splicing donor, is converted to A (G967A) to disrupt the pseudo-splicing donor sequence (conversion of the amino acid from Val to Ile)

Fig. 4

*Dystrophin* gene → Exon 45 tttgccttttggtatcttacag|GAACTCCAGGATGGCATTGGGCAGCGGCAAACTGTTGTCAGAACATTGA
aaaacggaaaaccatagaatgtcCTTGAGGTCCTACGGTAACCGTGCCGTTTGACAACAGTCTTGAACT (SEQ ID NO:126)

1) 5'-TGGTATCTTACAGGAACTCCAGG (SEQ ID NO:127)
4) 5'-TCCAGGATGGCATTGGGCAGCGG (SEQ ID NO:128)   SpCas9
5) GGAAAACCATAGAATGTCCTTG-5' (SEQ ID NO:129)

(SEQ ID NO:130)

5) 5'-CTTACAGGAACTCCAGGATGGCATTGGGC (SEQ ID NO:131)   SaCas9
8) TGAGGTCCTACGTAACCGTGCCGTTT-5' (SEQ ID NO:132)

1) 5'-TTTTTGGTATCTTACAGGAACTCC (SEQ ID NO:133)
2) 5'-TTTTGGTATCTTACAGGAACTCCA (SEQ ID NO:134)   AsCpf1
3) 5'-TTTGGTATCTTACAGGAACTCCAG (SEQ ID NO:135)
4) TCCTACGTAACCCGTGGCCGTTT-5' (SEQ ID NO:136)

| sgRNA | Target strand | Target sequence | sgRNA spacer sequence used for cloning | PAM | Cleavage position (bp) (*1) | T7E1 indel activity [%] | Exon skipping Luc activity [A.U.] | Exon skipping Luc activity [A.U.] |
|---|---|---|---|---|---|---|---|---|
| DMD#1 | + | TGCTATCTTAAGAACGAACTCCAGGA (SEQ ID NO:165) | GTCTTATTCTACAGGAACTCC (SEQ ID NO:167) | AGG | 4 | 19.1 | 1.459 ± 0.024 | 1.459 |
| DMD#2 | + | AACTTTACAGGAACTCCAGGATGGC (SEQ ID NO:166) | GTCTTATTCTACAGGAACTCCAGGA (SEQ ID NO:168) | TGG | 6 | 18.3 | 2.069 ± 0.171 | 2.069 |
| DMD#3 | + | CAGGAACTCCAGGATGGCATTGG (SEQ ID NO:169) | GGAGGAACTCCAGGATGGCAT (SEQ ID NO:170) | TGG | 14 | 15.4 | 0.925 ± 0.097 | 0.925 |
| DMD#4 | + | TCCAGGATGGCATTGGCAGGG (SEQ ID NO:171) | GCCAAGGAATGGCATTGGCAG (SEQ ID NO:172) | CGG | 21 | 16.9 | 1.293 ± 0.063 | 1.293 |
| DMD#5 | + | GTTCCTGTAAGATACCAAAAAGG (SEQ ID NO:173) | GTTCCTGTAAGATACCAAAA (SEQ ID NO:174) | AGG | -13 | 13.2 | 0.622 ± 0.041 | 0.622 |
| DMD#6 | + | TCATTTTGGTTTTGGTATCTTACAGG (SEQ ID NO:175) | ACATTTTGGTTTTGGTATCTTAC (SEQ ID NO:176) | TGG | -16 | 8.6 | 0.073 ± 0.005 | 0.073 |
| DMD#7 | + | TTTGGTATCTTACAGG (SEQ ID NO:177) | ATGCCTTTTGGTATCTTAC (SEQ ID NO:178) | AGG | -5 | 21.5 | 0.648 ± 0.022 | 0.648 |
| DMD#8 | + | AGGAACTCCAGGATGGCATTGGC (SEQ ID NO:179) | AGGAACTCCAGGATGGCATT (SEQ ID NO:180) | GGG | 15 | 21.9 | 1.209 ± 0.066 | 1.209 |
| DMD#9 | - | GCCATGCTGGAGCATTGAATGGCCAATGCC (SEQ ID NO:181) | GCCAAGCTGGTGCAATGCATGCC (SEQ ID NO:182) | TGG | 11 | 24.0 | 1.03 ± 0.039 | 1.03 |
| DMD#10 | + | GTCAGAACATTGAATGAACTGG (SEQ ID NO:183) | GTCAAGAACATTGAATGCAAC (SEQ ID NO:184) | TGG | 53 | 21.0 | 0.294 ± 0.025 | 0.294 |
| DMD#11 | + | TCAGAACATTGAATGCAACTGGC (SEQ ID NO:185) | ACAGAACATTGAATGCACT (SEQ ID NO:186) | GGG | 54 | 20.0 | 0.633 ± 0.087 | 0.633 |
| DMD#12 | + | CAGAACATTGAATGCAACTGGGG (SEQ ID NO:187) | GGAACATTGAATGCAACTGG (SEQ ID NO:188) | GGG | 55 | 15.5 | 0.711 ± 0.065 | 0.711 |
| DMD#13 | - | AATACTGGATCCTTTTTGAGCC (SEQ ID NO:189) | AATACTGGATCCTTTTTG (SEQ ID NO:190) | AGG | 86 | 14.7 | 0.082 ± 0.009 | 0.082 |
| DMD#14 | + | AACAATGCCAGTATTCTACAGG (SEQ ID NO:191) | AACAATGCCAGTATTCTAC (SEQ ID NO:192) | AGG | 103 | 16.2 | 0.211 ± 0.008 | 0.211 |
| DMD#15 | - | CAATTTTTCCTGTAGAATACTGGC (SEQ ID NO:193) | GAATTTTTCCTGTAGAATAC (SEQ ID NO:194) | TGG | 108 | 18.3 | 0.188 ± 0.021 | 0.188 |
| DMD#16 | + | CAGTATTCTACAGGAAAAATTGCC (SEQ ID NO:195) | GAGTATTCTACAGGAAAAT (SEQ ID NO:196) | TGG | 112 | 24.0 | 0.124 ± 0.023 | 0.124 |
| DMD#17 | + | AGTATTCTACAGGAAAAATTGGG (SEQ ID NO:197) | AGTATTCTACAGGAAAAATT (SEQ ID NO:198) | GGG | 113 | 23.6 | 0.131 ± 0.007 | 0.131 |
| DMD#18 | + | AATTGGCCAACCTCAAATCCGGG (SEQ ID NO:199) | AATTGGGAAGCCTCAAATCGG (SEQ ID NO:200) | CGG | 129 | 20.2 | 0.784 ± 0.04 | 0.784 |
| DMD#19 | - | TGGGAAGCCTGAATCTGGGCTGA (SEQ ID NO:201) | AGGGAAGGCTGAATCTGGGC (SEQ ID NO:202) | TGG | 132 | 13.0 | 0.367 ± 0.036 | 0.367 |
| DMD#20 | + | AAGCCTGAATCTGGGCTGGAGGG (SEQ ID NO:203) | AAGCTGAATCTGGGCTGG (SEQ ID NO:204) | AGG | 136 | 17.4 | 1.39 ± 0.077 | 1.39 |
| DMD#21 | + | CCTGAATCTGGGTGGGAGGCAGGG (SEQ ID NO:205) | CCTGAATCTGGGCTGGAGGC (SEQ ID NO:206) | AGG | 139 | 15.4 | 0.874 ± 0.073 | 0.874 |
| DMD#22 | - | CCCTGCCTCCCAGATTCAGC (SEQ ID NO:207) | GCCTGCCTCCAGCCAGATTC (SEQ ID NO:208) | AGG | 128 | 18.3 | 0.482 ± 0.062 | 0.482 |
| DMD#23 | + | AGCTTGTCAGACAGAAAAAGAGG (SEQ ID NO:209) | AGCTGTCAGACAGAAAAAG (SEQ ID NO:210) | AGG | 171 | 23.0 | 1.057 ± 0.06 | 1.057 |
| DMD#24 | + | GTCAGACAGAAAAAGAGGTAGG (SEQ ID NO:211) | GTCAGACAGAAAAAGAGGT (SEQ ID NO:212) | AGG | 175 | 23.2 | 0.433 ± 0.041 | 0.433 |
| DMD#25 | + | TCAGACAGAAAAAGAGGTAGGGG (SEQ ID NO:213) | ACAGACAGAAAAAGAGGTA (SEQ ID NO:214) | GGG | 176 | 22.6 | 0.499 ± 0.066 | 0.499 |
| DMD#26 | + | GGTAGGGCAGAGATTCAATAGG (SEQ ID NO:215) | GGTAGGGCAGAGATCAAT (SEQ ID NO:216) | AGG | 192 | 29.6 | 0.168 ± 0.022 | 0.168 |

Fig. 14b

| sgRNA | Exon skipping activity[%] (Relative to the "Luc2 (G967A) +Int") |
|---|---|
| No transfection | 0.03 ± 0.05 |
| 100% skipping "Luc2 (G967A) +Int" | 100 ± 10.96 |
| No gRNA | 0.03 ± 0.01 |
| DMD#1 ×2 | 0.79 ± 0.28 |
| DMD#1 | 0.64 ± 0.24 |
| DMD#2 | 0.87 ± 0.19 |
| DMD#4 | 0.74 ± 0.43 |
| DMD#8 | 0.4 ± 0.18 |
| DMD#9 | 0.41 ± 0.14 |
| DMD#20 | 0.59 ± 0.15 |
| DMD#23 | 0.94 ± 0.43 |
| DMD#1 & #2 | 0.71 ± 0.16 |
| DMD#1 & #4 | 1.01 ± 0.17 |
| DMD#1 &# 8 | 0.5 ± 0.08 |
| DMD#1 & #9 | 0.58 ± 0.08 |
| DMD#1 & #20 | 28.76 ± 4.21 |
| DMD#1 & #23 | 48.43 ± 11.06 |
| DMD#2 &# 4 | 4.31 ± 0.56 |
| DMD#2 & #8 | 0.52 ± 0.18 |
| DMD#2 &# 9 | 0.61 ± 0.21 |
| DMD#2 & #20 | 12.64 ± 4.02 |
| DMD#2 & #23 | 43.23 ± 11.44 |
| DMD#4 &# 8 | 4.3 ± 0.59 |
| DMD#4 &# 9 | 7.39 ± 0.3 |
| DMD#4 &# 20 | 24.91 ± 5.96 |
| DMD#4 & #23 | 33.63 ± 6.48 |
| DMD#8 & #9 | 0.4 ± 0.1 |
| DMD#8 &# 20 | 2.62 ± 0.56 |
| DMD#8 & #23 | 45.6 ± 13.25 |
| DMD#9 & #20 | 3.05 ± 0.4 |
| DMD#9 & #23 | 38.42 ± 6.92 |
| DMD#20 & #23 | 0.23 ± 0.08 |

Fig.15

SEQUENCE LISTING

<160> NUMBER OF SEQ ID NOS: 219

<210> SEQ ID NO 1

```
<210> SEQ ID NO 1
<211> LENGTH: 20
<212> TYPE: DNA
<213> ORGANISM: Artificial Sequence
<220> FEATURE:
<223> OTHER INFORMATION: primer Luc2-Fwd-Splice

<400> SEQUENCE: 1
tgcccacact atttagcttc                                                    20

<210> SEQ ID NO 2
<211> LENGTH: 20
<212> TYPE: DNA
<213> ORGANISM: Artificial Sequence
<220> FEATURE:
<223> OTHER INFORMATION: primer Luc2-Rev-Splice

<400> SEQUENCE: 2
gtcgatgaga gcgtttgtag                                                    20

<210> SEQ ID NO 3
<211> LENGTH: 83
<212> TYPE: DNA
<213> ORGANISM: Artificial Sequence
<220> FEATURE:
<223> OTHER INFORMATION: scaffold1

<400> SEQUENCE: 3
gttttagagc tagaaatagc aagttaaaat aaggctagtc cgttatcaac ttgaaaaagt        60
ggcaccgagt cggtgctttt ttt                                                83

<210> SEQ ID NO 4
<211> LENGTH: 95
<212> TYPE: DNA
<213> ORGANISM: Artificial Sequence
<220> FEATURE:
<223> OTHER INFORMATION: modified scaffold

<400> SEQUENCE: 4
gttttagagc tatgctggaa acagcatagc aagttaaaat aaggctagtc cgttatcaac        60
ttgaaaaagt ggcaccgagt cggtgctttt ttttt                                   95

<210> SEQ ID NO 5
<211> LENGTH: 21
<212> TYPE: DNA
<213> ORGANISM: Artificial Sequence
<220> FEATURE:
<223> OTHER INFORMATION: scaffold for Cpf1
<220> FEATURE:
<221> NAME/KEY: misc_feature
<222> LOCATION: (22)..(41)
<223> OTHER INFORMATION: spacer sequence

<400> SEQUENCE: 5
gtaatttcta ctcttgtaga t                                                  21

<210> SEQ ID NO 6
<211> LENGTH: 23
<212> TYPE: DNA
<213> ORGANISM: Artificial Sequence
<220> FEATURE:
<223> OTHER INFORMATION: scaffold for Cpf1
<220> FEATURE:
<221> NAME/KEY: misc_feature
<222> LOCATION: (24)..(43)
<223> OTHER INFORMATION: spacer sequence

<400> SEQUENCE: 6
```
gggtaatttc tactcttgta gat                                              23

<210> SEQ ID NO 7
<211> LENGTH: 23
<212> TYPE: DNA
<213> ORGANISM: Artificial Sequence
<220> FEATURE:
<223> OTHER INFORMATION: spacer for Type II Cas9
<220> FEATURE:
<221> NAME/KEY: misc_feature
<222> LOCATION: (1)..(21)
<223> OTHER INFORMATION: n is a, c, g, or t

<400> SEQUENCE: 7
nnnnnnnnnn nnnnnnnnnn ngg                                              23

<210> SEQ ID NO 8
<211> LENGTH: 25
<212> TYPE: DNA
<213> ORGANISM: Artificial Sequence
<220> FEATURE:
<223> OTHER INFORMATION: Type V Cfp1 for Type V Cfp1
<220> FEATURE:
<221> NAME/KEY: misc_feature
<222> LOCATION: (6)..(25)
<223> OTHER INFORMATION: n is a, c, g, or t

<400> SEQUENCE: 8 ttttvnnnn nnnnnnnnnn nnnnn                                             25

<210> SEQ ID NO 9
<211> LENGTH: 20
<212> TYPE: DNA
<213> ORGANISM: Artificial Sequence
<220> FEATURE:
<223> OTHER INFORMATION: crRNA 1

<400> SEQUENCE: 9
tggtatctta caggaactcc                                                  20

<210> SEQ ID NO 10
<211> LENGTH: 20
<212> TYPE: DNA
<213> ORGANISM: Artificial Sequence
<220> FEATURE:
<223> OTHER INFORMATION: crRNA2

<400> SEQUENCE: 10
atcttacagg aactccagga                                                  20

<210> SEQ ID NO 11
<211> LENGTH: 20
<212> TYPE: DNA
<213> ORGANISM: Artificial Sequence
<220> FEATURE:
<223> OTHER INFORMATION: crRNA3

<400> SEQUENCE: 11
caggaactcc aggatggcat                                                  20

<210> SEQ ID NO 12
<211> LENGTH: 20
<212> TYPE: DNA
<213> ORGANISM: Artificial Sequence
<220> FEATURE:
<223> OTHER INFORMATION: crRNA4

<400> SEQUENCE: 12
tccaggatgg cattgggcag                                                    20

<210> SEQ ID NO 13
<211> LENGTH: 20
<212> TYPE: DNA
<213> ORGANISM: Artificial Sequence
<220> FEATURE:
<223> OTHER INFORMATION: crRNA5

<400> SEQUENCE: 13
gttcctgtaa gataccaaaa                                                    20

<210> SEQ ID NO 14
<211> LENGTH: 275
<212> TYPE: DNA
<213> ORGANISM: Artificial Sequence
<220> FEATURE:
<223> OTHER INFORMATION: SphcCas9-D10A

<400> SEQUENCE: 14
attcagtcga ccatggataa gaaatacagc attggactgg ccattgggac aaactccgtg        60
ggatgggccg tgattacaga cgaatacaaa gtgccttcaa agaagttcaa ggtgctgggc       120
aacaccgata gacacagcat caagaaaaat ctgattggag ccctgctgtt cgactccggc       180
gagacagctg aagcaactcg gctgaaaaga actgctcgga gaaggtatac cgccgaaag       240 aataggatct gctacctgca ggagattttc agcaa                                 275

<210> SEQ ID NO 15
<211> LENGTH: 135
<212> TYPE: DNA
<213> ORGANISM: Artificial Sequence
<220> FEATURE:
<223> OTHER INFORMATION: PCR product
<220> FEATURE:
<221> NAME/KEY: misc_feature
<222> LOCATION: (18)..(36)
<223> OTHER INFORMATION: n is a, c, g, or t

<400> SEQUENCE: 15
gagaccactt ggatccrnnn nnnnnnnnn nnnnnngttt tagagctaga aatagcaagt         60
taaaataagg ctagtccgtt atcaacttga aaaagtggca ccgagtcggt gcttttttg       120 aattcaaacc cgggc                                                      135

<210> SEQ ID NO 16
<211> LENGTH: 57
<212> TYPE: DNA
<213> ORGANISM: Artificial Sequence
<220> FEATURE:
<223> OTHER INFORMATION: Sp-sgRNA-XXX-fwd
<220> FEATURE:
<221> NAME/KEY: misc_feature
<222> LOCATION: (18)..(36)
<223> OTHER INFORMATION: n is a, c, g, or t

<400> SEQUENCE: 16
gagaccactt ggatccrnnn nnnnnnnnn nnnnnngttt tagagctaga aatagca            57

<210> SEQ ID NO 17
<211> LENGTH: 57
<212> TYPE: DNA
<213> ORGANISM: Artificial Sequence
<220> FEATURE:
<223> OTHER INFORMATION: primer Sp-sgRNA-DMD1-fwd

```
<400> SEQUENCE: 17
gagaccactt ggatccgggt atcttacagg aactccgttt tagagctaga aatagca        57

<210> SEQ ID NO 18
<211> LENGTH: 57
<212> TYPE: DNA
<213> ORGANISM: Artificial Sequence
<220> FEATURE:
<223> OTHER INFORMATION: primer Sp-sgRNA-DMD2-fwd

<400> SEQUENCE: 18
gagaccactt ggatccgtct tacaggaact ccaggagttt tagagctaga aatagca        57

<210> SEQ ID NO 19
<211> LENGTH: 57
<212> TYPE: DNA
<213> ORGANISM: Artificial Sequence
<220> FEATURE:
<223> OTHER INFORMATION: primer Sp-sgRNA-DMD3-fwd

<400> SEQUENCE: 19
gagaccactt ggatccgagg aactccagga tggcatgttt tagagctaga aatagca        57

<210> SEQ ID NO 20
<211> LENGTH: 57
<212> TYPE: DNA
<213> ORGANISM: Artificial Sequence
<220> FEATURE:
<223> OTHER INFORMATION: primer Sp-sgRNA-DMD4-fwd

<400> SEQUENCE: 20
gagaccactt ggatccgcca ggatggcatt gggcaggttt tagagctaga aatagca        57

<210> SEQ ID NO 21
<211> LENGTH: 57
<212> TYPE: DNA
<213> ORGANISM: Artificial Sequence
<220> FEATURE:
<223> OTHER INFORMATION: primer Sp-sgRNA-DMD5-fwd

<400> SEQUENCE: 21
gagaccactt ggatccgttc ctgtaagata ccaaaagttt tagagctaga aatagca        57

<210> SEQ ID NO 22
<211> LENGTH: 57
<212> TYPE: DNA
<213> ORGANISM: Artificial Sequence
<220> FEATURE:
<223> OTHER INFORMATION: primer Sp-sgRNA-DMD6-fwd

<400> SEQUENCE: 22
gagaccactt ggatccgcat ttttgttttg cctttttgtt tagagctaga aatagca        57

<210> SEQ ID NO 23
<211> LENGTH: 57
<212> TYPE: DNA
<213> ORGANISM: Artificial Sequence
<220> FEATURE:
<223> OTHER INFORMATION: primer Sp-sgRNA-DMD7fwd

<400> SEQUENCE: 23
gagaccactt ggatccgtgc cttttttggta tcttacgttt tagagctaga aatagca       57

<210> SEQ ID NO 24
```

```
<211> LENGTH: 57
<212> TYPE: DNA
<213> ORGANISM: Artificial Sequence
<220> FEATURE:
<223> OTHER INFORMATION: primer Sp-sgRNA-DMD8-fwd

<400> SEQUENCE: 24
gagaccactt ggatccagga actccaggat ggcattgttt tagagctaga aatagca          57

<210> SEQ ID NO 25
<211> LENGTH: 57
<212> TYPE: DNA
<213> ORGANISM: Artificial Sequence
<220> FEATURE:
<223> OTHER INFORMATION: primer Sp-sgRNA-DMD9-fwd

<400> SEQUENCE: 25
gagaccactt ggatccgccg ctgcccaatg ccatccgttt tagagctaga aatagca          57

<210> SEQ ID NO 26
<211> LENGTH: 57
<212> TYPE: DNA
<213> ORGANISM: Artificial Sequence
<220> FEATURE:
<223> OTHER INFORMATION: primer Sp-sgRNA-DMD10-fwd

<400> SEQUENCE: 26
gagaccactt ggatccgtca gaacattgaa tgcaacgttt tagagctaga aatagca          57

<210> SEQ ID NO 27
<211> LENGTH: 57
<212> TYPE: DNA
<213> ORGANISM: Artificial Sequence
<220> FEATURE:
<223> OTHER INFORMATION: primer Sp-sgRNA-DMD11-fwd

<400> SEQUENCE: 27
gagaccactt ggatccgcag aacattgaat gcaactgttt tagagctaga aatagca          57

<210> SEQ ID NO 28
<211> LENGTH: 57
<212> TYPE: DNA
<213> ORGANISM: Artificial Sequence
<220> FEATURE:
<223> OTHER INFORMATION: primer Sp-sgRNA-DMD12-fwd

<400> SEQUENCE: 28
gagaccactt ggatccgaga acattgaatg caactggttt tagagctaga aatagca          57

<210> SEQ ID NO 29
<211> LENGTH: 57
<212> TYPE: DNA
<213> ORGANISM: Artificial Sequence
<220> FEATURE:
<223> OTHER INFORMATION: primer Sp-sgRNA-DMD13-fwd

<400> SEQUENCE: 29
gagaccactt ggatccaata ctggcatctg tttttggttt tagagctaga aatagca          57

<210> SEQ ID NO 30
<211> LENGTH: 57
<212> TYPE: DNA
<213> ORGANISM: Artificial Sequence
<220> FEATURE:
<223> OTHER INFORMATION: primer Sp-sgRNA-DMD14-fwd

<400> SEQUENCE: 30
```
gagaccactt ggatccaaca gatgccagta ttctacgttt tagagctaga aatagca        57

<210> SEQ ID NO 31
<211> LENGTH: 57
<212> TYPE: DNA
<213> ORGANISM: Artificial Sequence
<220> FEATURE:
<223> OTHER INFORMATION: primer Sp-sgRNA-DMD15-fwd

<400> SEQUENCE: 31
gagaccactt ggatccgaat ttttcctgta gaatacgttt tagagctaga aatagca        57

<210> SEQ ID NO 32
<211> LENGTH: 57
<212> TYPE: DNA
<213> ORGANISM: Artificial Sequence
<220> FEATURE:
<223> OTHER INFORMATION: primer Sp-sgRNA-DMD16-fwd

<400> SEQUENCE: 32
gagaccactt ggatccgagt attctacagg aaaaatgttt tagagctaga aatagca        57

<210> SEQ ID NO 33
<211> LENGTH: 57
<212> TYPE: DNA
<213> ORGANISM: Artificial Sequence
<220> FEATURE:
<223> OTHER INFORMATION: primer Sp-sgRNA-DMD17-fwd

<400> SEQUENCE: 33
gagaccactt ggatccagta ttctacagga aaaattgttt tagagctaga aatagca        57

<210> SEQ ID NO 34
<211> LENGTH: 57
<212> TYPE: DNA
<213> ORGANISM: Artificial Sequence
<220> FEATURE:
<223> OTHER INFORMATION: primer Sp-sgRNA-DMD18-fwd

<400> SEQUENCE: 34
gagaccactt ggatccaatt gggaagcctg aatctggttt tagagctaga aatagca        57

<210> SEQ ID NO 35
<211> LENGTH: 57
<212> TYPE: DNA
<213> ORGANISM: Artificial Sequence
<220> FEATURE:
<223> OTHER INFORMATION: primer Sp-sgRNA-DMD19-fwd

<400> SEQUENCE: 35
gagaccactt ggatccgggg aagcctgaat ctgcgggttt tagagctaga aatagca        57

<210> SEQ ID NO 36
<211> LENGTH: 57
<212> TYPE: DNA
<213> ORGANISM: Artificial Sequence
<220> FEATURE:
<223> OTHER INFORMATION: primer Sp-sgRNA-DMD20-fwd

<400> SEQUENCE: 36
gagaccactt ggatccaagc ctgaatctgc ggtggcgttt tagagctaga aatagca        57

<210> SEQ ID NO 37
<211> LENGTH: 57
<212> TYPE: DNA

```
<213> ORGANISM: Artificial Sequence
<220> FEATURE:
<223> OTHER INFORMATION: primer Sp-sgRNA-DMD21-fwd

<400> SEQUENCE: 37
gagaccactt ggatccgctg aatctgcggt ggcagggttt tagagctaga aatagca      57

<210> SEQ ID NO 38
<211> LENGTH: 57
<212> TYPE: DNA
<213> ORGANISM: Artificial Sequence
<220> FEATURE:
<223> OTHER INFORMATION: primer Sp-sgRNA-DMD22-fwd

<400> SEQUENCE: 38
gagaccactt ggatccgctc ctgccaccgc agattcgttt tagagctaga aatagca      57

<210> SEQ ID NO 39
<211> LENGTH: 57
<212> TYPE: DNA
<213> ORGANISM: Artificial Sequence
<220> FEATURE:
<223> OTHER INFORMATION: primer Sp-sgRNA-DMD23-fwd

<400> SEQUENCE: 39
gagaccactt ggatccagct gtcagacaga aaaaggttt tagagctaga aatagca       57

<210> SEQ ID NO 40
<211> LENGTH: 57
<212> TYPE: DNA
<213> ORGANISM: Artificial Sequence
<220> FEATURE:
<223> OTHER INFORMATION: primer Sp-sgRNA-DMD24-fwd

<400> SEQUENCE: 40
gagaccactt ggatccgtca gacagaaaaa agaggtgttt tagagctaga aatagca      57

<210> SEQ ID NO 41
<211> LENGTH: 57
<212> TYPE: DNA
<213> ORGANISM: Artificial Sequence
<220> FEATURE:
<223> OTHER INFORMATION: primer Sp-sgRNA-DMD25-fwd

<400> SEQUENCE: 41
gagaccactt ggatccgcag acagaaaaaa gaggtagttt tagagctaga aatagca      57

<210> SEQ ID NO 42
<211> LENGTH: 57
<212> TYPE: DNA
<213> ORGANISM: Artificial Sequence
<220> FEATURE:
<223> OTHER INFORMATION: primer Sp-sgRNA-DMD26-fwd

<400> SEQUENCE: 42
gagaccactt ggatccggta gggcgacaga tctaatgttt tagagctaga aatagca      57

<210> SEQ ID NO 43
<211> LENGTH: 96
<212> TYPE: DNA
<213> ORGANISM: Artificial Sequence
<220> FEATURE:
<223> OTHER INFORMATION: primer Sp-sgRNA-Universal-rev

<400> SEQUENCE: 43
gcccgggttt gaattcaaaa aaagcaccga ctcggtgcca cttttttcaag ttgataacgg  60
```

```
actagcctta ttttaacttg ctatttctag ctctaa                                    96

<210> SEQ ID NO 44
<211> LENGTH: 63
<212> TYPE: DNA
<213> ORGANISM: Artificial Sequence
<220> FEATURE:
<223> OTHER INFORMATION: primer sgRNA-DMD-SA-5

<400> SEQUENCE: 44
gagaccactt ggatccatta caggaactcc aggatggcag ttttagtact ctggaaacag          60
aat                                                                        63

<210> SEQ ID NO 45
<211> LENGTH: 63
<212> TYPE: DNA
<213> ORGANISM: Artificial Sequence
<220> FEATURE:
<223> OTHER INFORMATION: primer sgRNA-DMD-SA-8

<400> SEQUENCE: 45
gagaccactt ggatccattg ccgctgccca atgccatccg ttttagtact ctggaaacag          60
aat                                                                        63

<210> SEQ ID NO 46
<211> LENGTH: 96
<212> TYPE: DNA
<213> ORGANISM: Artificial Sequence
<220> FEATURE:
<223> OTHER INFORMATION: primer SA1-gRNA-Universal-Rev

<400> SEQUENCE: 46
gcccgggttt gaattcaaaa aaatctcgcc aacaagttga cgagataaac acggcatttt          60
gccttgtttt agtagattct gtttccagag tactaa                                   96

<210> SEQ ID NO 47
<211> LENGTH: 39
<212> TYPE: DNA
<213> ORGANISM: Artificial Sequence
<220> FEATURE:
<223> OTHER INFORMATION: primer AsCpf1-gRNA-Universal-GGG-fwd

<400> SEQUENCE: 47
gagaccactt ggatccgggt aatttctact cttgtagat                                 39

<210> SEQ ID NO 48
<211> LENGTH: 37
<212> TYPE: DNA
<213> ORGANISM: Artificial Sequence
<220> FEATURE:
<223> OTHER INFORMATION: primer AsCpf1-gRNA-Universal-G-fwd

<400> SEQUENCE: 48
gagaccactt ggatccgtaa tttctactct tgtagat                                   37

<210> SEQ ID NO 49
<211> LENGTH: 63
<212> TYPE: DNA
<213> ORGANISM: Artificial Sequence
<220> FEATURE:
<223> OTHER INFORMATION: primer AsCpf1-gRNA-XXX-rev
<220> FEATURE:
<221> NAME/KEY: misc_feature
<222> LOCATION: (24)..(43)
```

<223> OTHER INFORMATION: n is a, c, g, or t

<400> SEQUENCE: 49
gcccgggttt gaattcaaaa aaannnnnnn nnnnnnnnnn nnnatctaca agagtagaaa    60
tta    63

<210> SEQ ID NO 50
<211> LENGTH: 63
<212> TYPE: DNA
<213> ORGANISM: Artificial Sequence
<220> FEATURE:
<223> OTHER INFORMATION: primer AsCpf1-gRNA-DMD1-rev

<400> SEQUENCE: 50
gcccgggttt gaattcaaaa aaaggagttc ctgtaagata ccaatctaca agagtagaaa    60
tta    63

<210> SEQ ID NO 51
<211> LENGTH: 63
<212> TYPE: DNA
<213> ORGANISM: Artificial Sequence
<220> FEATURE:
<223> OTHER INFORMATION: primer AsCpf1-gRNA-DMD2-rev

<400> SEQUENCE: 51
gcccgggttt gaattcaaaa aaatggagtt cctgtaagat accatctaca agagtagaaa    60
tta    63

<210> SEQ ID NO 52
<211> LENGTH: 63
<212> TYPE: DNA
<213> ORGANISM: Artificial Sequence
<220> FEATURE:
<223> OTHER INFORMATION: primer AsCpf1-gRNA-DMD3-rev

<400> SEQUENCE: 52
gcccgggttt gaattcaaaa aaactggagt tcctgtaaga tacatctaca agagtagaaa    60
tta    63

<210> SEQ ID NO 53
<211> LENGTH: 63
<212> TYPE: DNA
<213> ORGANISM: Artificial Sequence
<220> FEATURE:
<223> OTHER INFORMATION: primer AsCpf1-gRNA-DMD4-rev

<400> SEQUENCE: 53
gcccgggttt gaattcaaaa aaaaggatgg cattgggcag cggatctaca agagtagaaa    60
tta    63

<210> SEQ ID NO 54
<211> LENGTH: 74
<212> TYPE: DNA
<213> ORGANISM: Artificial Sequence
<220> FEATURE:
<223> OTHER INFORMATION: primer SSA-DMD-all-ss

<400> SEQUENCE: 54
gtcgtgcctt tttggtatct tacaggaact ccaggatggc attgggcagc ggcaaactgt    60
tgtcagaaca tggt    74

```
<210> SEQ ID NO 55
<211> LENGTH: 74
<212> TYPE: DNA
<213> ORGANISM: Artificial Sequence
<220> FEATURE:
<223> OTHER INFORMATION: primer SSA-DMD-all-as

<400> SEQUENCE: 55
cggtaccatg ttctgacaac agtttgccgc tgcccaatgc catcctggag ttcctgtaag    60
ataccaaaaa ggca                                                      74

<210> SEQ ID NO 56
<211> LENGTH: 56
<212> TYPE: DNA
<213> ORGANISM: Artificial Sequence
<220> FEATURE:
<223> OTHER INFORMATION: primer DMD-MiSeq-Rd1-fwd-X
<220> FEATURE:
<221> NAME/KEY: misc_feature
<222> LOCATION: (31)..(34)
<223> OTHER INFORMATION: n is a, c, g, or t

<400> SEQUENCE: 56
ctctttccct acacgacgct cttccgatct nnnnaataaa agacatggg gcttca         56

<210> SEQ ID NO 57
<211> LENGTH: 54
<212> TYPE: DNA
<213> ORGANISM: Artificial Sequence
<220> FEATURE:
<223> OTHER INFORMATION: primer DMD-MiSeq-Rd2-rev-X
<220> FEATURE:
<221> NAME/KEY: misc_feature
<222> LOCATION: (31)..(34)
<223> OTHER INFORMATION: n is a, c, g, or t

<400> SEQUENCE: 57
ctggagttca gacgtgtgct cttccgatct nnnnctggca tctgttttg agga           54

<210> SEQ ID NO 58
<211> LENGTH: 49
<212> TYPE: DNA
<213> ORGANISM: Artificial Sequence
<220> FEATURE:
<223> OTHER INFORMATION: primer Multiplex P5 fwd

<400> SEQUENCE: 58
aatgatacgg cgaccaccga gatctacact ctttccctac acgacgctc                49

<210> SEQ ID NO 59
<211> LENGTH: 49
<212> TYPE: DNA
<213> ORGANISM: Artificial Sequence
<220> FEATURE:
<223> OTHER INFORMATION: primer Multiplex P7 rev

<400> SEQUENCE: 59
caagcagaag acggcatacg agatgtgact ggagttcaga cgtgtgctc                49

<210> SEQ ID NO 60
<211> LENGTH: 56
<212> TYPE: DNA
<213> ORGANISM: Artificial Sequence
<220> FEATURE:
<223> OTHER INFORMATION: primer DMD-MiSeq-Rd1-fwd1-AGTC

<400> SEQUENCE: 60
```
ctctttccct acacgacgct cttccgatct agtcaataaa aagacatggg gcttca       56

<210> SEQ ID NO 61
<211> LENGTH: 56
<212> TYPE: DNA
<213> ORGANISM: Artificial Sequence
<220> FEATURE:
<223> OTHER INFORMATION: primer DMD-MiSeq-Rd1-fwd2-GTCA

<400> SEQUENCE: 61
ctctttccct acacgacgct cttccgatct gtcaaataaa aagacatggg gcttca       56

<210> SEQ ID NO 62
<211> LENGTH: 56
<212> TYPE: DNA
<213> ORGANISM: Artificial Sequence
<220> FEATURE:
<223> OTHER INFORMATION: primer DMD-MiSeq-Rd1-fwd3-TCAG

<400> SEQUENCE: 62
ctctttccct acacgacgct cttccgatct tcagaataaa aagacatggg gcttca       56

<210> SEQ ID NO 63
<211> LENGTH: 56
<212> TYPE: DNA
<213> ORGANISM: Artificial Sequence
<220> FEATURE:
<223> OTHER INFORMATION: primer DMD-MiSeq-Rd1-fwd4-CAGT

<400> SEQUENCE: 63
ctctttccct acacgacgct cttccgatct cagtaataaa aagacatggg gcttca       56

<210> SEQ ID NO 64
<211> LENGTH: 56
<212> TYPE: DNA
<213> ORGANISM: Artificial Sequence
<220> FEATURE:
<223> OTHER INFORMATION: primer DMD-MiSeq-Rd1-fwd5-ATGC

<400> SEQUENCE: 64
ctctttccct acacgacgct cttccgatct atgcaataaa aagacatggg gcttca       56

<210> SEQ ID NO 65
<211> LENGTH: 56
<212> TYPE: DNA
<213> ORGANISM: Artificial Sequence
<220> FEATURE:
<223> OTHER INFORMATION: primer DMD-MiSeq-Rd1-fwd6-TGCA

<400> SEQUENCE: 65
ctctttccct acacgacgct cttccgatct tgcaaataaa aagacatggg gcttca       56

<210> SEQ ID NO 66
<211> LENGTH: 56
<212> TYPE: DNA
<213> ORGANISM: Artificial Sequence
<220> FEATURE:
<223> OTHER INFORMATION: primer DMD-MiSeq-Rd1-fwd7-GCAT

<400> SEQUENCE: 66
ctctttccct acacgacgct cttccgatct gcataataaa aagacatggg gcttca       56

<210> SEQ ID NO 67
<211> LENGTH: 56
<212> TYPE: DNA
<213> ORGANISM: Artificial Sequence

```
<220> FEATURE:
<223> OTHER INFORMATION: primer DMD-MiSeq-Rd1-fwd8-CATG

<400> SEQUENCE: 67
ctctttccct acacgacgct cttccgatct catgaataaa aagacatggg gcttca      56

<210> SEQ ID NO 68
<211> LENGTH: 56
<212> TYPE: DNA
<213> ORGANISM: Artificial Sequence
<220> FEATURE:
<223> OTHER INFORMATION: primer DMD-MiSeq-Rd1-fwd9-AACG

<400> SEQUENCE: 68
ctctttccct acacgacgct cttccgatct aacgaataaa aagacatggg gcttca      56

<210> SEQ ID NO 69
<211> LENGTH: 56
<212> TYPE: DNA
<213> ORGANISM: Artificial Sequence
<220> FEATURE:
<223> OTHER INFORMATION: primer DMD-MiSeq-Rd1-fwd10-ACGA

<400> SEQUENCE: 69
ctctttccct acacgacgct cttccgatct acgaaataaa aagacatggg gcttca      56

<210> SEQ ID NO 70
<211> LENGTH: 56
<212> TYPE: DNA
<213> ORGANISM: Artificial Sequence
<220> FEATURE:
<223> OTHER INFORMATION: primer DMD-MiSeq-Rd1-fwd11-CGAA

<400> SEQUENCE: 70
ctctttccct acacgacgct cttccgatct cgaaaataaa aagacatggg gcttca      56

<210> SEQ ID NO 71
<211> LENGTH: 56
<212> TYPE: DNA
<213> ORGANISM: Artificial Sequence
<220> FEATURE:
<223> OTHER INFORMATION: primer DMD-MiSeq-Rd1-fwd12-GAAC

<400> SEQUENCE: 71
ctctttccct acacgacgct cttccgatct gaacaataaa aagacatggg gcttca      56

<210> SEQ ID NO 72
<211> LENGTH: 56
<212> TYPE: DNA
<213> ORGANISM: Artificial Sequence
<220> FEATURE:
<223> OTHER INFORMATION: primer DMD-MiSeq-Rd1-fwd13-TACC

<400> SEQUENCE: 72
ctctttccct acacgacgct cttccgatct taccaataaa aagacatggg gcttca      56

<210> SEQ ID NO 73
<211> LENGTH: 56
<212> TYPE: DNA
<213> ORGANISM: Artificial Sequence
<220> FEATURE:
<223> OTHER INFORMATION: primer DMD-MiSeq-Rd1-fwd14-ACCT

<400> SEQUENCE: 73
ctctttccct acacgacgct cttccgatct acctaataaa aagacatggg gcttca      56
```

<210> SEQ ID NO 74
<211> LENGTH: 54
<212> TYPE: DNA
<213> ORGANISM: Artificial Sequence
<220> FEATURE:
<223> OTHER INFORMATION: primer DMD-MiSeq-Rd2-rev1-AGTC

<400> SEQUENCE: 74
ctggagttca gacgtgtgct cttccgatct agtcctggca tctgttttg agga          54

<210> SEQ ID NO 75
<211> LENGTH: 54
<212> TYPE: DNA
<213> ORGANISM: Artificial Sequence
<220> FEATURE:
<223> OTHER INFORMATION: primer DMD-MiSeq-Rd2-rev2-GTCA

<400> SEQUENCE: 75
ctggagttca gacgtgtgct cttccgatct gtcactggca tctgttttg agga          54

<210> SEQ ID NO 76
<211> LENGTH: 54
<212> TYPE: DNA
<213> ORGANISM: Artificial Sequence
<220> FEATURE:
<223> OTHER INFORMATION: primer DMD-MiSeq-Rd2-rev3-TCAG

<400> SEQUENCE: 76
ctggagttca gacgtgtgct cttccgatct tcagctggca tctgttttg agga          54

<210> SEQ ID NO 77
<211> LENGTH: 54
<212> TYPE: DNA
<213> ORGANISM: Artificial Sequence
<220> FEATURE:
<223> OTHER INFORMATION: primer DMD-MiSeq-Rd2-rev4-CAGT

<400> SEQUENCE: 77
ctggagttca gacgtgtgct cttccgatct cagtctggca tctgttttg agga          54

<210> SEQ ID NO 78
<211> LENGTH: 54
<212> TYPE: DNA
<213> ORGANISM: Artificial Sequence
<220> FEATURE:
<223> OTHER INFORMATION: primer DMD-MiSeq-Rd2-rev5-ATGC

<400> SEQUENCE: 78
ctggagttca gacgtgtgct cttccgatct atgcctggca tctgttttg agga          54

<210> SEQ ID NO 79
<211> LENGTH: 54
<212> TYPE: DNA
<213> ORGANISM: Artificial Sequence
<220> FEATURE:
<223> OTHER INFORMATION: primer DMD-MiSeq-Rd2-rev6-TGCA

<400> SEQUENCE: 79
ctggagttca gacgtgtgct cttccgatct tgcactggca tctgttttg agga          54

<210> SEQ ID NO 80
<211> LENGTH: 54
<212> TYPE: DNA
<213> ORGANISM: Artificial Sequence
<220> FEATURE:
<223> OTHER INFORMATION: primer DMD-MiSeq-Rd2-rev7-GCAT

<400> SEQUENCE: 80
ctggagttca gacgtgtgct cttccgatct gcatctggca tctgttttg agga            54

<210> SEQ ID NO 81
<211> LENGTH: 54
<212> TYPE: DNA
<213> ORGANISM: Artificial Sequence
<220> FEATURE:
<223> OTHER INFORMATION: primer DMD-MiSeq-Rd2-rev8-CATG

<400> SEQUENCE: 81
ctggagttca gacgtgtgct cttccgatct catgctggca tctgttttg agga            54

<210> SEQ ID NO 82
<211> LENGTH: 54
<212> TYPE: DNA
<213> ORGANISM: Artificial Sequence
<220> FEATURE:
<223> OTHER INFORMATION: primer DMD-MiSeq-Rd2-rev9-AACG

<400> SEQUENCE: 82
ctggagttca gacgtgtgct cttccgatct aacgctggca tctgttttg agga            54

<210> SEQ ID NO 83
<211> LENGTH: 54
<212> TYPE: DNA
<213> ORGANISM: Artificial Sequence
<220> FEATURE:
<223> OTHER INFORMATION: primer DMD-MiSeq-Rd2-rev10-ACGA

<400> SEQUENCE: 83
ctggagttca gacgtgtgct cttccgatct acgactggca tctgttttg agga            54

<210> SEQ ID NO 84
<211> LENGTH: 54
<212> TYPE: DNA
<213> ORGANISM: Artificial Sequence
<220> FEATURE:
<223> OTHER INFORMATION: primer DMD-MiSeq-Rd2-rev11-CGAA

<400> SEQUENCE: 84
ctggagttca gacgtgtgct cttccgatct cgaactggca tctgttttg agga            54

<210> SEQ ID NO 85
<211> LENGTH: 54
<212> TYPE: DNA
<213> ORGANISM: Artificial Sequence
<220> FEATURE:
<223> OTHER INFORMATION: primer DMD-MiSeq-Rd2-rev12-GAAC

<400> SEQUENCE: 85
ctggagttca gacgtgtgct cttccgatct gaacctggca tctgttttg agga            54

<210> SEQ ID NO 86
<211> LENGTH: 54
<212> TYPE: DNA
<213> ORGANISM: Artificial Sequence
<220> FEATURE:
<223> OTHER INFORMATION: primer DMD-MiSeq-Rd2-rev13-TACC

<400> SEQUENCE: 86
ctggagttca gacgtgtgct cttccgatct taccctggca tctgttttg agga            54

<210> SEQ ID NO 87

```
<211> LENGTH: 54
<212> TYPE: DNA
<213> ORGANISM: Artificial Sequence
<220> FEATURE:
<223> OTHER INFORMATION: primer DMD-MiSeq-Rd2-rev14-ACCT

<400> SEQUENCE: 87
ctggagttca gacgtgtgct cttccgatct acctctggca tctgttttg agga        54

<210> SEQ ID NO 88
<211> LENGTH: 1000
<212> TYPE: DNA
<213> ORGANISM: Artificial Sequence
<220> FEATURE:
<223> OTHER INFORMATION: NarI-AgeI-DMD-Ex45-gBlock

<400> SEQUENCE: 88
gccagcggcg gggcgccgct cagcaaggag gtaggtgagg ccgtggccaa acgcttccac    60
ctaccaggta agtctttgat ttgtcgaccg tatccacgat cactaagaaa cccaaatact   120
ttgttcatgt ttaaattta caacatttca tagactatta aacatggaac atccttgtgg   180
ggacaagaaa tcgaatttgc tcttgaaaag gtttccaact aattgatttg taggacatta   240
taacatcctc tagctgacaa gcttacaaaa ataaaaactg gagctaaccg agagggtgct   300
tttttccctg acacataaaa ggtgtctttc tgtcttgtat cctttggata tgggcatgtc   360
agtttcatag ggaaattttc acatggagct tttgtatttc tttctttgcc agtacaactg   420
catgtggtag cacactgttt aatctttct caaataaaaa gacatggggc ttcatttttg   480
ttttgccttt ttggtatctt acaggaactc caggatggca ttgggcagcg gcaaactgtt   540
gtcagaacat tgaatgcaac tggggaagaa ataattcagc aatcctcaaa aacagatgcc   600
agtattctac aggaaaaatt gggaagcctg aatctgcggt ggcaggaggt ctgcaaacag   660
ctgtcagaca gaaaaagag gtagggcgac agatctaata ggaatgaaaa cattttagca   720 gacttttaa gctttcttta gaagaatatt tcatgagaga ttataagcag ggtgaaaggc   780
gtcgacgttt gcattaacaa atagtttgag aactatgttg gaaaaaaaa taacaatttt   840 attcttcttt ctccaggcat ccgccagggc tacggcctga cagaaacaac cagcgccatt   900
ctgatcaccc ccgaagggga cgacaagcct ggcgcagtag gcaaggtggt gcccttcttc   960
gaggctaagg tggtggactt ggacaccggt aagacactgg                        1000

<210> SEQ ID NO 89
<211> LENGTH: 396
<212> TYPE: DNA
<213> ORGANISM: Artificial Sequence
<220> FEATURE:
<223> OTHER INFORMATION: gBlock11-PV-3'TR-5'TR

<400> SEQUENCE: 89
gaaaagtgcc acctgacgtc atctgttaac attatacgcg tttaacccta gaaagataat    60
catattgtga cgtacgttaa agataatcat gcgtaaaatt gacgcatgtg ttttatcggt   120
ctgtatatcg aggtttattt attaatttga atagatatta gtttattta tatttacact   180 tacatactaa taataaattc aacaaacaat ttatttatgt ttatttattt attaaaaaaa   240
aacaaaaact caaaatttct tctataaagt aacaaaactt ttaaacattc tctcttttac   300
aaaaataaac ttattttgta ctttaaaaac agtcatgttg tattataaaa taagtaatta   360
gcttaaccta tacataatag aaacaaatta tactta                              396
```

```
<210> SEQ ID NO 90
<211> LENGTH: 308
<212> TYPE: DNA
<213> ORGANISM: Artificial Sequence
<220> FEATURE:
<223> OTHER INFORMATION: gBlock12-PV-3'TR-5'TR

<400> SEQUENCE: 90
cctatacata atagaaacaa attatactta ttagtcagtc agaaacaact ttggcacata      60
tcaatattat gctctgctag cgatatctgt aaaacgacgg ccagttctag acttaagctt    120
catggtcata gctgtttcct gctcgagtta attaaccaac aagctcgtca tcgctttgca    180
gaagagcaga gaggatatgc tcatcgtcta aagaactacc cattttatta tatattagtc    240
acgatatcta taacaagaaa atatatatat aataagttat cacgtaagta gaacatgaaa    300
taacaata                                                             308

<210> SEQ ID NO 91
<211> LENGTH: 315
<212> TYPE: DNA
<213> ORGANISM: Artificial Sequence
<220> FEATURE:
<223> OTHER INFORMATION: gBlock13-PV-3'TR-5'TR

<400> SEQUENCE: 91
atcacgtaag tagaacatga aataacaata taattatcgt atgagttaaa tcttaaaagt     60
cacgtaaaag ataatcatgc gtcattttga ctcacgcggt cgttatagtt caaaatcagt    120
gacacttacc gcattgacaa gcacgcctca cgggagctcc aagcggcgac tgagatgtcc    180
taaatgcaca gcgacggatt cgcgctattt agaaagagag agcaatattt caagaatgca    240
tgcgtcaatt ttacgcagac tatctttcta gggttaatac gtataataca tatgattcag    300
ctgcattaat gaatc                                                     315

<210> SEQ ID NO 92
<211> LENGTH: 33
<212> TYPE: DNA
<213> ORGANISM: Artificial Sequence
<220> FEATURE:
<223> OTHER INFORMATION: primer pHL-PacI-rHBB-pA-IF-fw

<400> SEQUENCE: 92
gtatacctcg agttaaattc actcctcagg tgc                                  33

<210> SEQ ID NO 93
<211> LENGTH: 38
<212> TYPE: DNA
<213> ORGANISM: Artificial Sequence
<220> FEATURE:
<223> OTHER INFORMATION: primer pPV-PacI-rHBB-pA-IF-rev

<400> SEQUENCE: 93
cgagcttgtt ggttaattaa gtcgagggat ctccataa                             38

<210> SEQ ID NO 94
<211> LENGTH: 19
<212> TYPE: DNA
<213> ORGANISM: Artificial Sequence
<220> FEATURE:
<223> OTHER INFORMATION: primer Luc2-NcoI-IF-Fwd

<400> SEQUENCE: 94
gcccccttca ccatggaag                                                  19
```

<210> SEQ ID NO 95
<211> LENGTH: 20
<212> TYPE: DNA
<213> ORGANISM: Artificial Sequence
<220> FEATURE:
<223> OTHER INFORMATION: primer Luc2-V323I-fwd

<400> SEQUENCE: 95
cagcaaggag ataggtgagg                                              20

<210> SEQ ID NO 96
<211> LENGTH: 20
<212> TYPE: DNA
<213> ORGANISM: Artificial Sequence
<220> FEATURE:
<223> OTHER INFORMATION: primer Luc2-V323I-rev

<400> SEQUENCE: 96
cctcacctat ctccttgctg                                              20

<210> SEQ ID NO 97
<211> LENGTH: 27
<212> TYPE: DNA
<213> ORGANISM: Artificial Sequence
<220> FEATURE:
<223> OTHER INFORMATION: primer Luc2-SalI-IF-Rev

<400> SEQUENCE: 97
taatgcaaac gtcgacaaat caaagac                                      27

<210> SEQ ID NO 98
<211> LENGTH: 22
<212> TYPE: DNA
<213> ORGANISM: Artificial Sequence
<220> FEATURE:
<223> OTHER INFORMATION: primer DMD-Ex45-SalI-IF-F

<400> SEQUENCE: 98
tctttgattt gtcgaccgta tc                                           22

<210> SEQ ID NO 99
<211> LENGTH: 19
<212> TYPE: DNA
<213> ORGANISM: Artificial Sequence
<220> FEATURE:
<223> OTHER INFORMATION: primer DMD-Ex45-SalI-IF-R

<400> SEQUENCE: 99
taatgcaaac gtcgacgcc                                               19

<210> SEQ ID NO 100
<211> LENGTH: 38
<212> TYPE: DNA
<213> ORGANISM: Artificial Sequence
<220> FEATURE:
<223> OTHER INFORMATION: primer HDMD-SR-1kbFrag-fwd

<400> SEQUENCE: 100
tctttgattt gtcgagggat atcttgatgg gatgctcc                          38

<210> SEQ ID NO 101
<211> LENGTH: 37
<212> TYPE: DNA
<213> ORGANISM: Artificial Sequence
<220> FEATURE:
<223> OTHER INFORMATION: primer HDMD-SR-1kbFrag-rev

<400> SEQUENCE: 101
taatgcaaac gtcgaaaacc actaactagc cacaagt                                    37

<210> SEQ ID NO 102
<211> LENGTH: 35
<212> TYPE: DNA
<213> ORGANISM: Artificial Sequence
<220> FEATURE:
<223> OTHER INFORMATION: primer HDMD-SR-2kbFrag-fwd

<400> SEQUENCE: 102
tctttgattt gtcgaattgt gaggcaccgt gtcac                                      35

<210> SEQ ID NO 103
<211> LENGTH: 36
<212> TYPE: DNA
<213> ORGANISM: Artificial Sequence
<220> FEATURE:
<223> OTHER INFORMATION: primer HDMD-SR-2kbFrag-rev

<400> SEQUENCE: 103
taatgcaaac gtcgactctt tggctcaagt tcccct                                     36

<210> SEQ ID NO 104
<211> LENGTH: 37
<212> TYPE: DNA
<213> ORGANISM: Artificial Sequence
<220> FEATURE:
<223> OTHER INFORMATION: primer HDMD-SR-4kbFrag-fwd

<400> SEQUENCE: 104
tctttgattt gtcgagctgc agcattagtt tatagca                                    37

<210> SEQ ID NO 105
<211> LENGTH: 35
<212> TYPE: DNA
<213> ORGANISM: Artificial Sequence
<220> FEATURE:
<223> OTHER INFORMATION: primer HDMD-SR-4kbFrag-rev

<400> SEQUENCE: 105
taatgcaaac gtcgaaactt tggcaagggg tgtgt                                      35

<210> SEQ ID NO 106
<211> LENGTH: 1744
<212> TYPE: DNA
<213> ORGANISM: Artificial Sequence
<220> FEATURE:
<223> OTHER INFORMATION: Luc2(V323I)-hDMD-Ex45[-]

<400> SEQUENCE: 106
atggaagatg ccaaaaacat taagaagggc ccagcgccat tctacccact cgaagacggg          60
accgccggcg agcagctgca caaagccatg aagcgctacg ccctggtgcc cggcaccatc         120
gcctttaccg acgcacatat cgaggtggac attacctacg ccgagtactt cgagatgagc         180
gttcggctgg cagaagctat gaagcgctat gggctgaata caaaccatcg gatcgtggtg         240
tgcagcgaga atagcttgca gttcttcatg cccgtgttgg gtgccctgtt catcggtgtg         300
gctgtggccc cagctaacga catctacaac gagcgcgagc tgctgaacag catgggcatc         360
agccagccca ccgtcgtatt cgtgagcaag aaagggctgc aaaagatcct caacgtgcaa         420
aagaagctac cgatcataca aaagatcatc atcatggata gcaagaccga ctaccagggc         480

```
ttccaaagca tgtacacctt cgtgacttcc catttgccac ccggcttcaa cgagtacgac      540
ttcgtgcccg agagcttcga ccgggacaaa accatcgccc tgatcatgaa cagtagtggc      600
agtaccggat tgcccaaggg cgtagcccta ccgcaccgca ccgcttgtgt ccgattcagt      660
catgcccgcg accccatctt cggcaaccag atcatccccg acaccgctat cctcagcgtg      720
gtgccatttc accacggctt cggcatgttc accacgctgg gctacttgat ctgcggcttt      780
cgggtcgtgc tcatgtaccg cttcgaggag gagctattct tgcgcagctt gcaagactat      840
aagattcaat ctgccctgct ggtgcccaca ctatttagct tcttcgctaa gagcactctc      900
atcgacaagt acgacctaag caacttgcac gagatcgcca gcggcggggc gccgctcagc      960
aaggagatag gtgaggccgt ggccaaacgc ttccacctac caggtaagtc tttgatttgt     1020
cgacgtttgc attaacaaat agtttgagaa ctatgttgga aaaaaaaata acaattttat     1080
tcttcttcct ccaggcatcc gccagggcta cggcctgaca gaaacaacca gcgccattct     1140
gatcaccccc gaaggggacg acaagcctgg cgcagtaggc aaggtggtgc ccttcttcga     1200
ggctaaggtg gtggacttgg acaccggtaa gacactgggt gtgaaccagc gcggcgagct     1260
gtgcgtccgt ggccccatga tcatgagcgg ctacgttaac aaccccgagg ctacaaacgc     1320
tctcatcgac aaggacggct ggctgcacag cggcgacatc gcctactggg acgaggacga     1380
gcacttcttc atcgtggacc ggctgaagag cctgatcaaa tacaagggct accaggtagc     1440
cccagccgaa ctgagagca tcctgctgca acacccaac atcttcgacg ccggggtcgc      1500
cggcctgccc gacgacgatg ccggcgagct gcccgccgca gtcgtcgtgc tggaacacgg     1560
taaaaccatg accgagaagg agatcgtgga ctatgtggcc agccaggtta caaccgccaa     1620
gaagctgcgc ggtggtgttg tgttcgtgga cgaggtgcct aaaggactga ccggcaagtt     1680
ggacgcccgc aagatccgcg agattctcat taaggccaag aagggcggca agatcgccgt     1740
gtaa                                                                  1744
```

<210> SEQ ID NO 107
<211> LENGTH: 2442
<212> TYPE: DNA
<213> ORGANISM: Artificial Sequence
<220> FEATURE:
<223> OTHER INFORMATION: Luc2(V323I)-hDMD-Ex45[+]

<400> SEQUENCE: 107

```
atggaagatg ccaaaaacat taagaagggc ccagcgccat tctacccact cgaagacggg       60
accgccggcg agcagctgca caaagccatg aagcgctacg ccctggtgcc cggcaccatc      120
gcctttaccg acgcacatat cgaggtggac attacctacg ccgagtactt cgagatgagc      180
gttcggctgg cagaagctat gaagcgctat gggctgaata caaaccatcg gatcgtggtg      240
tgcagcgaga atagcttgca gttcttcatg cccgtgttgg gtgccctgtt catcggtgtg      300
gctgtggccc cagctaacga catctacaac gagcgcgagc tgctgaacag catgggcatc      360
agccagccca ccgtcgtatt cgtgagcaag aaagggctgc aaaagatcct caacgtgcaa      420
aagaagctac cgatcataca aaagatcatc atcatggata gcaagaccga ctaccagggc      480
ttccaaagca tgtacaccct tcgtgacttc ccatttgcca ccggcttcaa cgagtacgac      540
ttcgtgcccg agagcttcga ccgggacaaa accatcgccc tgatcatgaa cagtagtggc      600
agtaccggat tgcccaaggg cgtagcccta ccgcaccgca ccgcttgtgt ccgattcagt      660
catgcccgcg accccatctt cggcaaccag atcatccccg acaccgctat cctcagcgtg      720
gtgccatttc accacggctt cggcatgttc accacgctgg gctacttgat ctgcggcttt      780
```

```
cgggtcgtgc tcatgtaccg cttcgaggag gagctattct tgcgcagctt gcaagactat    840
aagattcaat ctgccctgct ggtgcccaca ctatttagct tcttcgctaa gagcactctc    900
atcgacaagt acgacctaag caacttgcac gagatcgcca gcggcggggc gccgctcagc    960
aaggagatag gtgaggccgt ggccaaacgc ttccacctac caggtaagtc tttgatttgt   1020
cgaccgtatc cacgatcact aagaaaccca aatactttgt tcatgtttaa attttacaac   1080
atttcataga ctattaaaca tggaacatcc ttgtggggac aagaaatcga atttgctctt   1140
gaaaaggttt ccaactaatt gatttgtagg acattataac atcctctagc tgacaagctt   1200
acaaaaataa aaactggagc taaccgagag ggtgcttttt tccctgacac ataaaaggtg   1260
tctttctgtc ttgtatcctt tggatatggg catgtcagtt tcatagggaa attttcacat   1320
ggagcttttg tatttctttc tttgccagta caactgcatg tggtagcaca ctgtttaatc   1380
ttttctcaaa taaaagaca tggggcttca tttttgtttt gccttttggg tatcttacag    1440
gaactccagg atggcattgg gcagcggcaa actgttgtca gaacattgaa tgcaactggg   1500
gaagaaataa ttcagcaatc ctcaaaaaca gatgccagta ttctacagga aaaattggga   1560
agcctgaatc tgcggtggca ggaggtctgc aaacagctgt cagacagaaa aaagaggtag   1620
ggcgacagat ctaataggaa tgaaaacatt ttagcagact ttttaagctt tctttagaag   1680
aatatttcat gagagattat aagcagggtg aaaggcgtcg acgtttgcat taacaaatag   1740
tttgagaact atgttggaaa aaaaaataac aattttattc ttctttctcc aggcatccgc   1800
cagggctacg gcctgacaga aacaaccagc gccattctga tcacccccga aggggacgac   1860
aagcctggcg cagtaggcaa ggtggtgccc ttcttcgagg ctaaggtggt ggacttggac   1920
accggtaaga cactgggtgt gaaccagcgc ggcgagctgt gcgtccgtgg ccccatgatc   1980
atgagcggct acgttaacaa ccccgaggct acaaacgctc tcatcgacaa ggacggctgg   2040
ctgcacagcg gcgacatcgc ctactgggac gaggacgagc acttcttcat cgtggaccgg   2100
ctgaagagcc tgatcaaata caagggctac caggtagccc cagccgaact ggagagcatc   2160
ctgctgcaac accccaacat cttcgacgcc gggtcgccg  gcctgccga cgacgatgcc    2220 ggcgagctgc ccgccgcagt cgtcgtgctg gaacacggta aaaccatgac cgagaaggag   2280
atcgtggact atgtggccag ccaggttaca accgccaaga agctgcgcgg tggtgttgtg   2340
ttcgtggacg aggtgcctaa aggactgacc ggcaagttgg acgcccgcaa gatccgcgag   2400
attctcatta aggccaagaa gggcggcaag atcgccgtgt aa                      2442

<210> SEQ ID NO 108
<211> LENGTH: 2676
<212> TYPE: DNA
<213> ORGANISM: Artificial Sequence
<220> FEATURE:
<223> OTHER INFORMATION: Luc2(V323I)-hDMD-Ex45[+](1kb)

<400> SEQUENCE: 108
atggaagatg ccaaaaacat taagaagggc ccagcgccat tctacccact cgaagacggg     60
accgccggcg agcagctgca caaagccatg aagcgctacg ccctggtgcc cggcaccatc    120
gcctttaccg acgcacatat cgaggtggac attacctacg ccgagtactt cgagatgagc    180
gttcggctgg cagaagctat gaagcgctat gggctgaata caaaccatcg gatcgtggtg    240
tgcagcgaga atagcttgca gttcttcatg cccgtgttgg gtgccctgtt catcggtgtg    300
gctgtggccc cagctaacga catctacaac gagcgcgagc tgctgaacag catgggcatc    360
```

-continued

```
agccagccca ccgtcgtatt cgtgagcaag aaagggctgc aaaagatcct caacgtgcaa      420
aagaagctac cgatcataca aaagatcatc atcatggata gcaagaccga ctaccagggc      480
ttccaaagca tgtacacctt cgtgacttcc catttgccac ccggcttcaa cgagtacgac      540
ttcgtgcccg agagcttcga ccgggacaaa accatcgccc tgatcatgaa cagtagtggc      600
agtaccggat tgcccaaggg cgtagcccta ccgcaccgca ccgcttgtgt ccgattcagt      660
catgcccgcg accccatctt cggcaaccag atcatccccg acaccgctat cctcagcgtg      720
gtgccatttc accacggctt cggcatgttc accacgctgg gctacttgat ctgcggcttt      780
cgggtcgtgc tcatgtaccg cttcgaggag gagctattct tgcgcagctt gcaagactat      840
aagattcaat ctgccctgct ggtgcccaca ctatttagct tcttcgctaa gagcactctc      900
atcgacaagt acgacctaag caacttgcac gagatcgcca gcggcggggc gccgctcagc      960
aaggagatag gtgaggccgt ggccaaacgc ttccacctac caggtaagtc tttgatttgt     1020
cgaagcacgc atttggcttt ctgtgccttc aatacattcc aagggaaatt taaatgatga     1080
ttgaatttga cagtaacctt tttgaggttt tgttttcccc attaaacttg tacctctttg     1140
gctcaagttc cccttcaaga atgtattcac aaatgtggtg aaactagagg taagtgacac     1200
tatcactttt tttagcttca tagtcatatt catagctatt tttaaaacta agcaaagatc     1260
tgtctttcct acaaaacaat catttataat tgctttctaa aatcttcttg aaaaacaact     1320
gagattcagc ttgttgaagt taaaatatat tgaagatatt caccctttaag caatcatggg    1380 tgatttttaa agcaaacttc aagtttaaaa tagcagaaaa ccactaacta gccacaagta     1440
tatattttag tatatgaaaa aaagaaataa aaaatttctt tactgctgtt gattaatggt     1500
tgataggttc tttaatgtta gtgcctttca ccctgcttat aatctctcat gaaatattct     1560
tctaaagaaa gcttaaaaag tctgctaaaa tgttttcatt cctattagat ctgtcgccct     1620
acctcttttt tctgtctgac agctgtttgc agacctcctg ccaccgcaga ttcaggcttc     1680 ccaattttc ctgtagaata ctggcatctg tttttgagga ttgctgaatt atttcttccc      1740
cagttgcatt caatgttctg acaacagttt gccgctgccc aatgccatcc tggagttcct     1800
gtaagatacc aaaaaggcaa aacaaaaatg aagccccatg tcttttttatt tgagaaaaga    1860 ttaaacagtg tgctaccaca tgcagttgta ctggcaaaga aagaaataca aaagctccat     1920
gtgaaaattt ccctatgaaa ctgacatgcc ctcgacgttt gcattaacaa atagtttgag     1980
aactatgttg gaaaaaaaaa taacaatttt attcttcttt ctccaggcat ccgccagggc     2040
tacggcctga cagaaacaac cagcgccatt ctgatcaccc ccgaagggga cgacaagcct     2100
ggcgcagtag gcaaggtggt gcccttcttc gaggctaagg tggtggactt ggacaccggt     2160
aagacactgg gtgtgaacca gcgcggcgag ctgtgcgtcc gtggcccccat gatcatgagc     2220 ggctacgtta caaccccga ggctacaaac gctctcatcg acaaggacgg ctggctgcac      2280
agcggcgaca tcgcctactg ggacgaggac gagcacttct tcatcgtgga ccggctgaag     2340
agcctgatca aatacaaggg ctaccaggta gccccagccg aactggagag catcctgctg     2400 caacaccccca acatcttcga cgccggggtc gccggcctgc ccgacgacga tgccggcgag     2460
ctgcccgccg cagtcgtcgt gctggaacac ggtaaaacca tgaccgagaa ggagatcgtg     2520
gactatgtgg ccagccaggt tacaaccgcc aagaagctgc gcggtggtgt tgtgttcgtg     2580
gacgaggtgc ctaaaggact gaccggcaag ttggacgccc gcaagatccg cgagattctc     2640
attaaggcca agaagggcgg caagatcgcc gtgtaa                               2676
```

<210> SEQ ID NO 109
<211> LENGTH: 3651
<212> TYPE: DNA
<213> ORGANISM: Artificial Sequence
<220> FEATURE:
<223> OTHER INFORMATION: Luc2(V323I)-hDMD-Ex45[+](2kb)

<400> SEQUENCE: 109

| | | | | | |
|---|---|---|---|---|---|
| atggaagatg | ccaaaaacat | taagaagggc | ccagcgccat | tctacccact | cgaagacggg | 60 |
| accgccggcg | agcagctgca | caaagccatg | aagcgctacg | ccctggtgcc | cggcaccatc | 120 |
| gcctttaccg | acgcacatat | cgaggtggac | attacctacg | ccgagtactt | cgagatgagc | 180 |
| gttcggctgg | cagaagctat | gaagcgctat | gggctgaata | caaaccatcg | gatcgtggtg | 240 |
| tgcagcgaga | atagcttgca | gttcttcatg | cccgtgttgg | gtgccctgtt | catcggtgtg | 300 |
| gctgtggccc | cagctaacga | catctacaac | gagcgcgagc | tgctgaacag | catgggcatc | 360 |
| agccagccca | ccgtcgtatt | cgtgagcaag | aaagggctgc | aaaagatcct | caacgtgcaa | 420 |
| aagaagctac | cgatcataca | aaagatcatc | atcatggata | gcaagaccga | ctaccagggc | 480 |
| ttccaaagca | tgtacacctt | cgtgacttcc | catttgccac | ccggcttcaa | cgagtacgac | 540 |
| ttcgtgcccg | agagcttcga | ccgggacaaa | accatcgccc | tgatcatgaa | cagtagtggc | 600 |
| agtaccggat | tgcccaaggg | cgtagcccta | ccgcaccgca | ccgcttgtgt | ccgattcagt | 660 |
| catgcccgcg | accccatctt | cggcaaccag | atcatccccg | acaccgctat | cctcagcgtg | 720 |
| gtgccatttc | accacggctt | cggcatgttc | accacgctgg | gctacttgat | ctgcggcttt | 780 |
| cgggtcgtgc | tcatgtaccg | cttcgaggag | gagctattct | tgcgcagctt | gcaagactat | 840 |
| aagattcaat | ctgccctgct | ggtgcccaca | ctatttagct | tcttcgctaa | gagcactctc | 900 |
| atcgacaagt | acgacctaag | caacttgcac | gagatcgcca | gcggcggggc | cgcgctcagc | 960 |
| aaggagatag | gtgaggccgt | ggccaaacgc | ttccacctac | caggtaagtc | tttgatttgt | 1020 |
| cgatctttaa | ctttggcaag | gggtgtgtgt | gtgtgtgtgt | gtgtgtgtgt | gtgtgtgtgt | 1080 |
| gtgtgtgtgt | gtgtgtgtgt | ttaggtcaac | taatgtgttt | attttgtaca | aaatatgaat | 1140 |
| tgtatctact | ttctgaataa | tgtaacatga | ataaagaggg | aaagaggagg | tgggcaaaga | 1200 |
| caactgacat | aattccaaaa | tcttctttt | aatacatctt | aacgaaagat | attcatcaat | 1260 |
| gagttgttct | agcttcctga | atattaaaat | ccacctatta | tgtggatgat | gggtgggatg | 1320 |
| caagagcttg | gcaaaagaac | gaagtttca | ttgttcataa | caatagtctc | atttggtaaa | 1380 |
| taaaggccaa | gtcttccttt | acgaaacaag | acacattaac | atcaacaact | ggaagcataa | 1440 |
| tacaaaatcc | catttataaa | ctctctaggc | tttccaactg | cagcagcacg | catttggctt | 1500 |
| tctgtgcctt | caatacattc | caagggaaat | ttaaatgatg | attgaatttg | acagtaacct | 1560 |
| ttttgaggtt | ttgttttccc | cattaaactt | gtacctcttt | ggctcaagtt | ccccttcaag | 1620 |
| aatgtattca | caaatgtggt | gaaactagag | gtaagtgaca | ctatcacttt | ttttagcttc | 1680 |
| atagtcatat | tcatagctat | ttttaaaact | aagcaaagat | ctgtcttcc | tacaaaacaa | 1740 |
| tcatttataa | ttgctttcta | aaatcttctt | gaaaacaac | tgagattcag | cttgttgaag | 1800 |
| ttaaaatata | ttgaagatat | tcacctttaa | gcaatcatgg | gtgattttta | aagcaaactt | 1860 |
| caagtttaaa | atagcagaaa | accactaact | agccacaagt | atatattta | gtatatgaaa | 1920 |
| aaaagaaata | aaaaatttct | ttactgctgt | tgattaatgg | ttgataggtt | ctttaatgtt | 1980 |
| agtgcctttc | accctgctta | taatctctca | tgaaatattc | ttctaaagaa | agcttaaaaa | 2040 |
| gtctgctaaa | atgttttcat | tcctattaga | tctgtcgccc | tacctctttt | ttctgtctga | 2100 |

| | |
|---|---|
| cagctgtttg cagacctcct gccaccgcag attcaggctt cccaattttt cctgtagaat | 2160 |
| actggcatct gttttgagg attgctgaat tatttcttcc ccagttgcat tcaatgttct | 2220 |
| gacaacagtt tgccgctgcc caatgccatc ctggagttcc tgtaagatac caaaaaggca | 2280 |
| aaacaaaaat gaagcccat gtctttttat ttgagaaaag attaaacagt gtgctaccac | 2340 |
| atgcagttgt actggcaaag aagaaatac aaaagctcca tgtgaaaatt tccctatgaa | 2400 |
| actgacatgc ccatatccaa aggatacaag acagaaagac acctttatg tgtcagggaa | 2460 |
| aaaagcaccc tctcggttag ctccagtttt tatttttgta agcttgtcag ctagaggatg | 2520 |
| ttataatgtc ctacaaatca attagttgga aaccttttca agagcaaatt cgatttcttg | 2580 |
| tccccacaag gatgttccat gtttaatagt ctatgaaatg ttgtaaaatt taaacatgaa | 2640 |
| caaagtattt gggtttctta gtgatcgtgg atacgagagg tgaaaaagaa caaacatagg | 2700 |
| ttagtcacag tattaaaaaa aaactctaga gatatttaaa taaaattaat tgctatatta | 2760 |
| gaagaaaatt catttcaaat tctgtctgcg tcaatgtatt ttgcattaga agccacaaaa | 2820 |
| aactgagaat taattgcttt caggagcatc ccatcaagat atccctaagc tacagtaata | 2880 |
| aattttaaaa taatctatag tcaccagagc attttttatga ttgtcatcga cgtttgcatt | 2940 |
| aacaaatagt ttgagaacta tgttggaaaa aaaaataaca attttattct tctttctcca | 3000 |
| ggcatccgcc agggctacgg cctgacagaa acaaccagcg ccattctgat caccccgaa | 3060 |
| ggggacgaca agcctggcgc agtaggcaag gtggtgccct tcttcgaggc taaggtggtg | 3120 |
| gacttggaca ccggtaagac actgggtgtg aaccagcgcg gcgagctgtg cgtccgtggc | 3180 |
| cccatgatca tgagcggcta cgttaacaac cccgaggcta caaacgctct catcgacaag | 3240 |
| gacggctggc tgcacagcgg cgacatcgcc tactgggacg aggacgagca cttcttcatc | 3300 |
| gtggaccggc tgaagagcct gatcaaatac aagggctacc agtagccccc agccgaactg | 3360 |
| gagagcatcc tgctgcaaca ccccaacatc ttcgacgccg gggtcgccgg cctgcccgac | 3420 |
| gacgatgccg gcgagctgcc cgccgcagtc gtcgtgctgg aacacggtaa aaccatgacc | 3480 |
| gagaaggaga tcgtggacta tgtggccagc caggttacaa ccgccaagaa gctgcgcggt | 3540 |
| ggtgttgtgt tcgtggacga ggtgcctaaa ggactgaccg gcaagttgga cgcccgcaag | 3600 |
| atccgcgaga ttctcattaa ggccaagaag ggcggcaaga tcgccgtgta a | 3651 |

<210> SEQ ID NO 110
<211> LENGTH: 5709
<212> TYPE: DNA
<213> ORGANISM: Artificial Sequence
<220> FEATURE:
<223> OTHER INFORMATION: Luc2(V323I)-hDMD-Ex45[+](4kb)

<400> SEQUENCE: 110

| | |
|---|---|
| atggaagatg ccaaaaacat taagaagggc ccagcgccat tctacccact cgaagacggg | 60 |
| accgccggcg agcagctgca caaagccatg aagcgctacg ccctggtgcc cggcaccatc | 120 |
| gcctttaccg acgcacatat cgaggtggac attacctacg ccgagtactt cgagatgagc | 180 |
| gttcggctgg cagaagctat gaagcgctat gggctgaata caaaccatcg gatcgtggtg | 240 |
| tgcagcgaga atagcttgca gttcttcatg cccgtgttgg gtgccctgtt catcggtgtg | 300 |
| gctgtggccc cagctaacga catctacaac gagcgcgagc tgctgaacag catgggcatc | 360 |
| agccagccca ccgtcgtatt cgtgagcaag aaagggctgc aaaagatcct caacgtgcaa | 420 |
| aagaagctac cgatcataca aaagatcatc atcatggata gcaagaccga ctaccagggc | 480 |
| ttccaaagca tgtacacctt cgtgacttcc catttgccac ccggcttcaa cgagtacgac | 540 |

```
ttcgtgcccg agagcttcga ccgggacaaa accatcgccc tgatcatgaa cagtagtggc    600
agtaccggat tgcccaaggg cgtagcccta ccgcaccgca ccgcttgtgt ccgattcagt    660
catgcccgcg accccatctt cggcaaccag atcatcccg acaccgctat cctcagcgtg     720
gtgccatttc accacggctt cggcatgttc accacgctgg gctacttgat ctgcggcttt    780
cgggtcgtgc tcatgtaccg cttcgaggag gagctattct tgcgcagctt gcaagactat    840
aagattcaat ctgccctgct ggtgcccaca ctatttagct tcttcgctaa gagcactctc    900
atcgacaagt acgacctaag caacttgcac gagatcgcca gcggcggggc gccgctcagc    960
aaggagatag gtgaggccgt ggccaaacgc ttccacctac caggtaagtc tttgatttgt   1020
cgatttgcaa ctacagggct ccatatagac atctagcttg aatttataca ctttctttca   1080
ttgatgtccc tggactaaaa aatgttaaat atttctaacc gctgtactta aagtccatta   1140
caaacgaaga ctactgttgt taagttgaat aggcatctta tatattttc accggtgcaa    1200 taaataactt ctattcccctt ctaacatctg cttgcgttgc actgagagta cactattgat  1260
tagcaatagg ttcgtgatta cagccccttct ataattaatt gttaggttaa catattattc  1320
ataaaatatt atttttattaa ttttttacttg atttgctact ggatgcttag aaatagctat 1380
gagtatattg gtagaaccag tactatatt ttattacatt tttacatttc ataaaattta    1440
agtgatataa aaatcctgag gaagtatgcc acaaaagtgg tctcagtgga aatttaaata   1500
tgttaacatt tatttttaaa atgtagcgtg aaatagacaa ctttaaaagc tcagcttaaa   1560
aaaaaaactc aaggaagctg aacttgactt tttaaagcac tgaagtgcaa tatttaatgt   1620
aggtcaacat gtttaaatgg gaaattttt ttcctaatta cagccaaatc cctagctgta    1680
attaacttaa aatttgtata ctatttcaca acagagtcag catataccac tttcttataa   1740
aattagaaag atctaaaatt ttagagctta tttggtgaaa caggcatatt gctacatctt   1800 tgttttataaa ttataatgtg cctttagagc ccaataacag ataacaagat tttgaaaatt  1860
caggtgaatt agagttatca gagggaatgt taatacactc tattcaaata ctatatgagt   1920
aagcatttta aaataggaaa caatactttt atatattatag aaaaataatc ttccagtcga  1980
tttaatccac tttatgaatt ctctccgtat atatatattt atagtatggt attcaatttt   2040
tttaattttc tcatttctta ccatcttaat ttggattaga ttgagcctag ttcagaaatg   2100
acattataca ggtttatacc tgttcatagt ataagcacat cagttatcta ataataaaa    2160 tacttgtatg attaagagaa gaatttcaat ctgggaaaaa agtatatgac ttacctaagg   2220
aagtagttta actacaaagt ttagttcttt attttatcta tctataatca agaagatttt   2280
caaaaccaag acttaattat tcaaaatatc ttttgatgag gctataattc tttaactttg   2340
gcaagggggt tgtgtgtgtg tgtgtgtgtg tgtgtgtgtg tgtgtgtgtg tgtgtgtgtg   2400
tgtgtttagg tcaactaatg tgtttatttt gtacaaaata tgaattgtat ctactttctg   2460
aataatgtaa catgaataaa gagggaaaga ggaggtgggc aaagacaact gacataattc   2520
caaaatcttc ttttttaatac atcttaacga aagatattca tcaatgagtt gttctagctt  2580
cctgaatatt aaaatccacc tattatgtgg atgatgggtg ggatgcaaga gcttggcaaa   2640
agaacgaagt tttcattgtt cataacaata gtctcatttg gtaaataaag gccaagtctt   2700
cctttacgaa acaagacaca ttaacatcaa caactggaag cataatacaa aatcccattt   2760
ataaactctc taggctttcc aactgcagca gcacgcattt ggctttctgt gccttcaata   2820
cattccaagg gaaatttaaa tgatgattga atttgacagt aaccttttg aggttttgtt    2880
```

```
ttccccatta aacttgtacc tctttggctc aagttcccct tcaagaatgt attcacaaat    2940
gtggtgaaac tagaggtaag tgacactatc actttttta gcttcatagt catattcata    3000 gctatttta aaactaagca aagatctgtc tttcctacaa aacaatcatt tataattgct    3060
ttctaaaatc ttccttgaaaa acaactgaga ttcagcttgt tgaagttaaa atatattgaa    3120
gatattcacc tttaagcaat catgggtgat ttttaaagca aacttcaagt ttaaaatagc    3180
agaaaaccac taactagcca caagtatata ttttagtata tgaaaaaaag aaataaaaaa    3240 tttcttact gctgttgatt aatggttgat aggttcttta atgttagtgc ctttcaccct    3300
gcttataatc tctcatgaaa tattcttcta aagaaagctt aaaaagtctg ctaaaatgtt    3360
ttcattccta ttagatctgt cgccctacct ctttttctg tctgacagct gtttgcagac    3420
ctcctgccac cgcagattca ggcttcccaa ttttcctgt agaatactgg catctgtttt    3480
tgaggattgc tgaattattt cttccccagt tgcattcaat gttctgacaa cagtttgccg    3540
ctgcccaatg ccatcctgga gttcctgtaa gataccaaaa aggcaaaaca aaatgaagc    3600 cccatgtctt tttatttgag aaaagattaa acagtgtgct accacatgca gttgtactgg    3660
caaagaaaga aatacaaaag ctccatgtga aatttccct atgaaactga catgcccata    3720 tccaaggat acaagacaga aagacaccttt ttatgtgtca gggaaaaag caccctctcg    3780 gttagctcca gttttattt ttgtaagctt gtcagctaga ggatgttata atgtcctaca    3840
aatcaattag ttggaaacct tttcaagagc aaattcgatt tcttgtcccc acaaggatgt    3900
tccatgttta atagtctatg aaatgttgta aaatttaaac atgaacaaag tatttgggtt    3960
tcttagtgat cgtggatacg agaggtgaaa aagaacaaac ataggttagt cacagtatta    4020
aaaaaaaact ctagagatat ttaaataaaa ttaattgcta tattagaaga aaattcattt    4080
caaattctgt ctgcgtcaat gtattttgca ttagaagcca caaaaactg agaattaatt    4140 gctttcagga gcatcccatc aagatatccc taagctacag taataaattt taaaataatc    4200
tatagtcacc agagcatttt tatgattgtc aagcttaaat attgtttact tttttcctga    4260
atgaaatttt aagagtaaag tatcagaaaa atagctcaat tgaaaggag aatattacaa    4320 ccaagtacac acaaaaacaa aatgctttt taccattaaa taaaaatggc aattacgttc    4380
tatttaactt tttaaaaaag ataatctaga atttgtaagg ccattaaaat aacatattaa    4440
ctaaatacga accttagaaa atgaaataat atctgagaac ttgaggtacc taccgtattt    4500
aaatctgaat gactcaaatc cttatgtcac tgacagaata atgtgcgtat gtagaaaact    4560
ctcctaatag atgtgattca tattctctaa tattttgta ttctcctact ccttgacaca    4620
atagcaagct gacagtagac cccagtacat gcttcctaaa tgaaggaagg aatgcatgtt    4680
ttctgagact gaggtaaagc tcccttagac tctcgtttca catacatttc ttggctttt    4740 tcttttcta cattcaagca aaattatttt cgaatactgg aaattttggt agcatacagt    4800
tagcaattaa aatactctgt aaatcagcaa accggtgaca cggtgcctca caatgaatat    4860
aaaactatgc acagttactg aactattcac aagctgtcct ggccatactc tcttgaatgc    4920
ccatgagatg tgctctagta acatgtgat atttccttgt aactagttgg ctttgctcca    4980
ttgctcgacg tttgcattaa caaatagttt gagaactatg ttggaaaaaa aataacaat    5040 tttattcttc tttctccagg catccgccag ggctacggcc tgacagaaac aaccagcgcc    5100
attctgatca cccccgaagg ggacgacaag cctggcgcag taggcaaggt ggtgcccttc    5160
ttcgaggcta aggtggtgga cttggacacc ggtaagacac tgggtgtgaa ccagcgcggc    5220
gagctgtgcg tccgtggccc catgatcatg agcggctacg ttaacaaccc cgaggctaca    5280
```

```
aacgctctca tcgacaagga cggctggctg cacagcggcg acatcgccta ctgggacgag    5340
gacgagcact tcttcatcgt ggaccggctg aagagcctga tcaaatacaa gggctaccag    5400
gtagccccag ccgaactgga gagcatcctg ctgcaacacc ccaacatctt cgacgccggg    5460
gtcgccggcc tgcccgacga cgatgccggc gagctgcccg ccgcagtcgt cgtgctggaa    5520
cacggtaaaa ccatgaccga aaggagatc gtggactatg tggccagcca ggttacaacc    5580
gccaagaagc tgcgcggtgg tgttgtgttc gtggacgagg tgcctaaagg actgaccggc    5640
aagttggacg cccgcaagat ccgcgagatt ctcattaagg ccaagaaggg cggcaagatc    5700
gccgtgtaa                                                            5709
```

<210> SEQ ID NO 111
<211> LENGTH: 22
<212> TYPE: PRT
<213> ORGANISM: Artificial Sequence
<220> FEATURE:
<223> OTHER INFORMATION: artificial peptide

<400> SEQUENCE: 111

Ala Ser Gly Gly Ala Pro Leu Ser Lys Glu Val Gly Glu Ala Val Ala
1               5                   10                  15

Lys Arg Phe His Leu Pro
            20

<210> SEQ ID NO 112
<211> LENGTH: 48
<212> TYPE: PRT
<213> ORGANISM: Artificial Sequence
<220> FEATURE:
<223> OTHER INFORMATION: artificial peptide

<400> SEQUENCE: 112

Gly Ile Arg Gln Gly Tyr Gly Leu Thr Glu Thr Thr Ser Ala Ile Leu
1               5                   10                  15

Ile Thr Pro Glu Gly Asp Asp Lys Pro Gly Ala Val Gly Lys Val Val
            20                  25                  30

Pro Phe Phe Glu Ala Lys Val Val Asp Leu Asp Thr Gly Lys Thr Leu
        35                  40                  45

<210> SEQ ID NO 113
<211> LENGTH: 29
<212> TYPE: DNA
<213> ORGANISM: Artificial Sequence
<220> FEATURE:
<223> OTHER INFORMATION: artificial sequence

<400> SEQUENCE: 113
ccgctcagca aggaggtagg tgaggccgt                                      29

<210> SEQ ID NO 114
<211> LENGTH: 15
<212> TYPE: DNA
<213> ORGANISM: Artificial Sequence
<220> FEATURE:
<223> OTHER INFORMATION: artificial sequence

<400> SEQUENCE: 114
aaggaggtag gtgag                                                     15

<210> SEQ ID NO 115
<211> LENGTH: 5

```
<212> TYPE: PRT
<213> ORGANISM: Artificial Sequence
<220> FEATURE:
<223> OTHER INFORMATION: artificial sequence

<400> SEQUENCE: 115

Lys Glu Val Gly Glu
1               5

<210> SEQ ID NO 116
<211> LENGTH: 15
<212> TYPE: DNA
<213> ORGANISM: Artificial Sequence
<220> FEATURE:
<223> OTHER INFORMATION: artificial sequence

<400> SEQUENCE: 116
aaggagatag gtgag                                                         15

<210> SEQ ID NO 117
<211> LENGTH: 5
<212> TYPE: PRT
<213> ORGANISM: Artificial Sequence
<220> FEATURE:
<223> OTHER INFORMATION: artificial sequence

<400> SEQUENCE: 117

Lys Glu Ile Gly Glu
1               5

<210> SEQ ID NO 118
<211> LENGTH: 79
<212> TYPE: DNA
<213> ORGANISM: Artificial Sequence
<220> FEATURE:
<223> OTHER INFORMATION: artificial sequence

<400> SEQUENCE: 118
gttttgcctt tttggtatct tacaggaact ccaggatggc attgggcagc ggcaaactgt        60
tgtcagaaca ttgaatgca                                                     79

<210> SEQ ID NO 119
<211> LENGTH: 79
<212> TYPE: DNA
<213> ORGANISM: Artificial Sequence
<220> FEATURE:
<223> OTHER INFORMATION: artificial sequence

<400> SEQUENCE: 119
tgcattcaat gttctgacaa cagtttgccg ctgcccaatg ccatcctgga gttcctgtaa        60
gataccaaaa aggcaaaac                                                     79

<210> SEQ ID NO 120
<211> LENGTH: 23
<212> TYPE: DNA
<213> ORGANISM: Artificial Sequence
<220> FEATURE:
<223> OTHER INFORMATION: artificial sequence

<400> SEQUENCE: 120
tggtatctta caggaactcc agg                                                23

<210> SEQ ID NO 121
<211> LENGTH: 23
<212> TYPE: DNA
```

```
<213> ORGANISM: Artificial Sequence
<220> FEATURE:
<223> OTHER INFORMATION: artificial sequence

<400> SEQUENCE: 121
atcttacagg aactccagga tgg                                              23

<210> SEQ ID NO 122
<211> LENGTH: 23
<212> TYPE: DNA
<213> ORGANISM: Artificial Sequence
<220> FEATURE:
<223> OTHER INFORMATION: artificial sequence

<400> SEQUENCE: 122
caggaactcc aggatggcat tgg                                              23

<210> SEQ ID NO 123
<211> LENGTH: 23
<212> TYPE: DNA
<213> ORGANISM: Artificial Sequence
<220> FEATURE:
<223> OTHER INFORMATION: artificial sequence

<400> SEQUENCE: 123
tccaggatgg cattgggcag cgg                                              23

<210> SEQ ID NO 124
<211> LENGTH: 23
<212> TYPE: DNA
<213> ORGANISM: Artificial Sequence
<220> FEATURE:
<223> OTHER INFORMATION: artificial sequence

<400> SEQUENCE: 124
gttcctgtaa gataccaaaa agg                                              23

<210> SEQ ID NO 125
<211> LENGTH: 62
<212> TYPE: DNA
<213> ORGANISM: Artificial Sequence
<220> FEATURE:
<223> OTHER INFORMATION: artificial sequence

<400> SEQUENCE: 125
ttgttttgcc ttttggtat cttacaggaa ctccaggatg gcattgggca gcggcaaact       60
gt                                                                     62

<210> SEQ ID NO 126
<211> LENGTH: 73
<212> TYPE: DNA
<213> ORGANISM: Artificial Sequence
<220> FEATURE:
<223> OTHER INFORMATION: artificial sequence

<400> SEQUENCE: 126
ttttgccttt tggtatctt acaggaactc caggatggca ttgggcagcg gcaaactgtt       60
gtcagaacat tga                                                         73

<210> SEQ ID NO 127
<211> LENGTH: 73
<212> TYPE: DNA
<213> ORGANISM: Artificial Sequence
<220> FEATURE:
<223> OTHER INFORMATION: artificial sequence
```

```
<400> SEQUENCE: 127
tcaatgttct gacaacagtt tgccgctgcc caatgccatc ctggagttcc tgtaagatac    60
caaaaaggca aaa                                                      73

<210> SEQ ID NO 128
<211> LENGTH: 23
<212> TYPE: DNA
<213> ORGANISM: Artificial Sequence
<220> FEATURE:
<223> OTHER INFORMATION: artificial sequence

<400> SEQUENCE: 128
tggtatctta caggaactcc agg                                           23

<210> SEQ ID NO 129
<211> LENGTH: 23
<212> TYPE: DNA
<213> ORGANISM: Artificial Sequence
<220> FEATURE:
<223> OTHER INFORMATION: artificial sequence

<400> SEQUENCE: 129
tccaggatgg cattgggcag cgg                                           23

<210> SEQ ID NO 130
<211> LENGTH: 23
<212> TYPE: DNA
<213> ORGANISM: Artificial Sequence
<220> FEATURE:
<223> OTHER INFORMATION: artificial sequence

<400> SEQUENCE: 130
gttcctgtaa gataccaaaa agg                                           23

<210> SEQ ID NO 131
<211> LENGTH: 29
<212> TYPE: DNA
<213> ORGANISM: Artificial Sequence
<220> FEATURE:
<223> OTHER INFORMATION: artificial sequence

<400> SEQUENCE: 131
cttacaggaa ctccaggatg gcattgggc                                     29

<210> SEQ ID NO 132
<211> LENGTH: 29
<212> TYPE: DNA
<213> ORGANISM: Artificial Sequence
<220> FEATURE:
<223> OTHER INFORMATION: artificial sequence

<400> SEQUENCE: 132
tttgccgctg cccaatgcca tcctggagt                                     29

<210> SEQ ID NO 133
<211> LENGTH: 24
<212> TYPE: DNA
<213> ORGANISM: Artificial Sequence
<220> FEATURE:
<223> OTHER INFORMATION: artificial sequence

<400> SEQUENCE: 133
tttttggtat cttacaggaa ctcc                                          24
```

```
<210> SEQ ID NO 134
<211> LENGTH: 24
<212> TYPE: DNA
<213> ORGANISM: Artificial Sequence
<220> FEATURE:
<223> OTHER INFORMATION: artificial sequence

<400> SEQUENCE: 134
ttttggtatc ttacaggaac tcca                                            24

<210> SEQ ID NO 135
<211> LENGTH: 24
<212> TYPE: DNA
<213> ORGANISM: Artificial Sequence
<220> FEATURE:
<223> OTHER INFORMATION: artificial sequence

<400> SEQUENCE: 135
tttggtatct tacaggaact ccag                                            24

<210> SEQ ID NO 136
<211> LENGTH: 24
<212> TYPE: DNA
<213> ORGANISM: Artificial Sequence
<220> FEATURE:
<223> OTHER INFORMATION: artificial sequence

<400> SEQUENCE: 136
tttgccgctg cccaatgcca tcct                                            24

<210> SEQ ID NO 137
<211> LENGTH: 23
<212> TYPE: DNA
<213> ORGANISM: Artificial Sequence
<220> FEATURE:
<223> OTHER INFORMATION: artificial sequence

<400> SEQUENCE: 137
ggtcctaccg taacccgtcg ccg                                             23

<210> SEQ ID NO 138
<211> LENGTH: 23
<212> TYPE: DNA
<213> ORGANISM: Artificial Sequence
<220> FEATURE:
<223> OTHER INFORMATION: artificial sequence

<400> SEQUENCE: 138
ggtcataaga tgtcctttt aac                                              23

<210> SEQ ID NO 139
<211> LENGTH: 23
<212> TYPE: DNA
<213> ORGANISM: Artificial Sequence
<220> FEATURE:
<223> OTHER INFORMATION: artificial sequence

<400> SEQUENCE: 139
ggaaaaacca tagaatgtcc ttg                                             23

<210> SEQ ID NO 140
<211> LENGTH: 23
<212> TYPE: DNA
<213> ORGANISM: Artificial Sequence
<220> FEATURE:
<223> OTHER INFORMATION: artificial sequence
```

<400> SEQUENCE: 140
ggagtttttg tctacggtca taa                                            23

<210> SEQ ID NO 141
<211> LENGTH: 23
<212> TYPE: DNA
<213> ORGANISM: Artificial Sequence
<220> FEATURE:
<223> OTHER INFORMATION: artificial sequence

<400> SEQUENCE: 141
ggacttagac gccaccgtcc tcc                                            23

<210> SEQ ID NO 142
<211> LENGTH: 247
<212> TYPE: DNA
<213> ORGANISM: Artificial Sequence
<220> FEATURE:
<223> OTHER INFORMATION: artificial sequence

<400> SEQUENCE: 142
catgggcttt catttttgtt ttgccttttt ggtatcttac aggaactcca ggatggcatt     60
gggcagcggc aaactgttgt cagaacattg aatgcaactg gggaagaaat aattcagcaa    120
tcctcaaaaa cagatgccag tattctacag gaaaaattgg gaagcctgaa tctgcggtgg    180
caggaggtct gcaaacagct gtcagacaga aaaagaggt agggcgacag atctaatagg    240
aatgaaa                                                             247

<210> SEQ ID NO 143
<211> LENGTH: 247
<212> TYPE: DNA
<213> ORGANISM: Artificial Sequence
<220> FEATURE:
<223> OTHER INFORMATION: artificial sequence

<400> SEQUENCE: 143
tttcattcct attagatctg tcgccctacc tctttttct gtctgacagc tgtttgcaga      60
cctcctgcca ccgcagattc aggcttccca attttcctg tagaatactg gcatctgttt    120
ttgaggattg ctgaattatt tcttccccag ttgcattcaa tgttctgaca acagtttgcc    180
gctgcccaat gccatcctgg agttcctgta agataccaaa aaggcaaaac aaaaatgaag   240
ccccatg                                                             247

<210> SEQ ID NO 144
<211> LENGTH: 23
<212> TYPE: DNA
<213> ORGANISM: Artificial Sequence
<220> FEATURE:
<223> OTHER INFORMATION: artificial sequence

<400> SEQUENCE: 144
tcatttttgt tttgcctttt tgg                                            23

<210> SEQ ID NO 145
<211> LENGTH: 23
<212> TYPE: DNA
<213> ORGANISM: Artificial Sequence
<220> FEATURE:
<223> OTHER INFORMATION: artificial sequence

<400> SEQUENCE: 145

```
gtcagaacat tgaatgcaac tgg                                              23

<210> SEQ ID NO 146
<211> LENGTH: 23
<212> TYPE: DNA
<213> ORGANISM: Artificial Sequence
<220> FEATURE:
<223> OTHER INFORMATION: artificial sequence

<400> SEQUENCE: 146
aacagatgcc agtattctac agg                                              23

<210> SEQ ID NO 147
<211> LENGTH: 23
<212> TYPE: DNA
<213> ORGANISM: Artificial Sequence
<220> FEATURE:
<223> OTHER INFORMATION: artificial sequence

<400> SEQUENCE: 147
agctgtcaga cagaaaaaag agg                                              23

<210> SEQ ID NO 148
<211> LENGTH: 23
<212> TYPE: DNA
<213> ORGANISM: Artificial Sequence
<220> FEATURE:
<223> OTHER INFORMATION: artificial sequence

<400> SEQUENCE: 148
ttgccttttt ggtatcttac agg                                              23

<210> SEQ ID NO 149
<211> LENGTH: 23
<212> TYPE: DNA
<213> ORGANISM: Artificial Sequence
<220> FEATURE:
<223> OTHER INFORMATION: artificial sequence

<400> SEQUENCE: 149
tcagaacatt gaatgcaact ggg                                              23

<210> SEQ ID NO 150
<211> LENGTH: 23
<212> TYPE: DNA
<213> ORGANISM: Artificial Sequence
<220> FEATURE:
<223> OTHER INFORMATION: artificial sequence

<400> SEQUENCE: 150
cagtattcta caggaaaaat tgg                                              23

<210> SEQ ID NO 151
<211> LENGTH: 23
<212> TYPE: DNA
<213> ORGANISM: Artificial Sequence
<220> FEATURE:
<223> OTHER INFORMATION: artificial sequence

<400> SEQUENCE: 151
gtcagacaga aaaagaggt agg                                               23

<210> SEQ ID NO 152
<211> LENGTH: 23
<212> TYPE: DNA
<213> ORGANISM: Artificial Sequence
```

-continued

<220> FEATURE:
<223> OTHER INFORMATION: artificial sequence

<400> SEQUENCE: 152
tggtatctta caggaactcc agg                                              23

<210> SEQ ID NO 153
<211> LENGTH: 23
<212> TYPE: DNA
<213> ORGANISM: Artificial Sequence
<220> FEATURE:
<223> OTHER INFORMATION: artificial sequence

<400> SEQUENCE: 153
cagaacattg aatgcaactg ggg                                              23

<210> SEQ ID NO 154
<211> LENGTH: 23
<212> TYPE: DNA
<213> ORGANISM: Artificial Sequence
<220> FEATURE:
<223> OTHER INFORMATION: artificial sequence

<400> SEQUENCE: 154
agtattctac aggaaaaatt ggg                                              23

<210> SEQ ID NO 155
<211> LENGTH: 23
<212> TYPE: DNA
<213> ORGANISM: Artificial Sequence
<220> FEATURE:
<223> OTHER INFORMATION: artificial sequence

<400> SEQUENCE: 155
tcagacagaa aaagaggta ggg                                               23

<210> SEQ ID NO 156
<211> LENGTH: 23
<212> TYPE: DNA
<213> ORGANISM: Artificial Sequence
<220> FEATURE:
<223> OTHER INFORMATION: artificial sequence

<400> SEQUENCE: 156
atcttacagg aactccagga tgg                                              23

<210> SEQ ID NO 157
<211> LENGTH: 23
<212> TYPE: DNA
<213> ORGANISM: Artificial Sequence
<220> FEATURE:
<223> OTHER INFORMATION: artificial sequence

<400> SEQUENCE: 157
aattgggaag cctgaatctg cgg                                              23

<210> SEQ ID NO 158
<211> LENGTH: 23
<212> TYPE: DNA
<213> ORGANISM: Artificial Sequence
<220> FEATURE:
<223> OTHER INFORMATION: artificial sequence

<400> SEQUENCE: 158
ggtagggcga cagatctaat agg                                              23

<210> SEQ ID NO 159
<211> LENGTH: 23
<212> TYPE: DNA
<213> ORGANISM: Artificial Sequence
<220> FEATURE:
<223> OTHER INFORMATION: artificial sequence

<400> SEQUENCE: 159
caggaactcc aggatggcat tgg                                          23

<210> SEQ ID NO 160
<211> LENGTH: 23
<212> TYPE: DNA
<213> ORGANISM: Artificial Sequence
<220> FEATURE:
<223> OTHER INFORMATION: artificial sequence

<400> SEQUENCE: 160
tgggaagcct gaatctgcgg tgg                                          23

<210> SEQ ID NO 161
<211> LENGTH: 23
<212> TYPE: DNA
<213> ORGANISM: Artificial Sequence
<220> FEATURE:
<223> OTHER INFORMATION: artificial sequence

<400> SEQUENCE: 161
aggaactcca ggatggcatt ggg                                          23

<210> SEQ ID NO 162
<211> LENGTH: 23
<212> TYPE: DNA
<213> ORGANISM: Artificial Sequence
<220> FEATURE:
<223> OTHER INFORMATION: artificial sequence

<400> SEQUENCE: 162
aagcctgaat ctgcggtggc agg                                          23

<210> SEQ ID NO 163
<211> LENGTH: 23
<212> TYPE: DNA
<213> ORGANISM: Artificial Sequence
<220> FEATURE:
<223> OTHER INFORMATION: artificial sequence

<400> SEQUENCE: 163
tccaggatgg cattgggcag cgg                                          23

<210> SEQ ID NO 164
<211> LENGTH: 23
<212> TYPE: DNA
<213> ORGANISM: Artificial Sequence
<220> FEATURE:
<223> OTHER INFORMATION: artificial sequence

<400> SEQUENCE: 164
cctgaatctg cggtggcagg agg                                          23

<210> SEQ ID NO 165
<211> LENGTH: 23
<212> TYPE: DNA
<213> ORGANISM: Artificial Sequence
<220> FEATURE:
<223> OTHER INFORMATION: artificial sequence

<400> SEQUENCE: 165
tggtatctta caggaactcc agg                                           23

<210> SEQ ID NO 166
<211> LENGTH: 20
<212> TYPE: DNA
<213> ORGANISM: Artificial Sequence
<220> FEATURE:
<223> OTHER INFORMATION: artificial sequence

<400> SEQUENCE: 166
gggtatctta caggaactcc                                               20

<210> SEQ ID NO 167
<211> LENGTH: 23
<212> TYPE: DNA
<213> ORGANISM: Artificial Sequence
<220> FEATURE:
<223> OTHER INFORMATION: artificial sequence

<400> SEQUENCE: 167
atcttacagg aactccagga tgg                                           23

<210> SEQ ID NO 168
<211> LENGTH: 20
<212> TYPE: DNA
<213> ORGANISM: Artificial Sequence
<220> FEATURE:
<223> OTHER INFORMATION: artificial sequence

<400> SEQUENCE: 168
gtcttacagg aactccagga                                               20

<210> SEQ ID NO 169
<211> LENGTH: 23
<212> TYPE: DNA
<213> ORGANISM: Artificial Sequence
<220> FEATURE:
<223> OTHER INFORMATION: artificial sequence

<400> SEQUENCE: 169
caggaactcc aggatggcat tgg                                           23

<210> SEQ ID NO 170
<211> LENGTH: 20
<212> TYPE: DNA
<213> ORGANISM: Artificial Sequence
<220> FEATURE:
<223> OTHER INFORMATION: artificial sequence

<400> SEQUENCE: 170
gaggaactcc aggatggcat                                               20

<210> SEQ ID NO 171
<211> LENGTH: 23
<212> TYPE: DNA
<213> ORGANISM: Artificial Sequence
<220> FEATURE:
<223> OTHER INFORMATION: artificial sequence

<400> SEQUENCE: 171
tccaggatgg cattgggcag cgg                                           23

<210> SEQ ID NO 172

```
<211> LENGTH: 20
<212> TYPE: DNA
<213> ORGANISM: Artificial Sequence
<220> FEATURE:
<223> OTHER INFORMATION: artificial sequence

<400> SEQUENCE: 172
gccaggatgg cattgggcag                                               20

<210> SEQ ID NO 173
<211> LENGTH: 23
<212> TYPE: DNA
<213> ORGANISM: Artificial Sequence
<220> FEATURE:
<223> OTHER INFORMATION: artificial sequence

<400> SEQUENCE: 173
gttcctgtaa gataccaaaa agg                                           23

<210> SEQ ID NO 174
<211> LENGTH: 20
<212> TYPE: DNA
<213> ORGANISM: Artificial Sequence
<220> FEATURE:
<223> OTHER INFORMATION: artificial sequence

<400> SEQUENCE: 174
gttcctgtaa gataccaaaa                                               20

<210> SEQ ID NO 175
<211> LENGTH: 23
<212> TYPE: DNA
<213> ORGANISM: Artificial Sequence
<220> FEATURE:
<223> OTHER INFORMATION: artificial sequence

<400> SEQUENCE: 175 tcattttttgt tttgcctttt tgg                                          23

<210> SEQ ID NO 176
<211> LENGTH: 20
<212> TYPE: DNA
<213> ORGANISM: Artificial Sequence
<220> FEATURE:
<223> OTHER INFORMATION: artificial sequence

<400> SEQUENCE: 176
acatttttgt tttgcctttt                                               20

<210> SEQ ID NO 177
<211> LENGTH: 23
<212> TYPE: DNA
<213> ORGANISM: Artificial Sequence
<220> FEATURE:
<223> OTHER INFORMATION: artificial sequence

<400> SEQUENCE: 177
ttgccttttt ggtatcttac agg                                           23

<210> SEQ ID NO 178
<211> LENGTH: 20
<212> TYPE: DNA
<213> ORGANISM: Artificial Sequence
<220> FEATURE:
<223> OTHER INFORMATION: artificial sequence

<400> SEQUENCE: 178
``` atgcctttt ggtatcttac                                           20

<210> SEQ ID NO 179
<211> LENGTH: 23
<212> TYPE: DNA
<213> ORGANISM: Artificial Sequence
<220> FEATURE:
<223> OTHER INFORMATION: artificial sequence

<400> SEQUENCE: 179
aggaactcca ggatggcatt ggg                                      23

<210> SEQ ID NO 180
<211> LENGTH: 20
<212> TYPE: DNA
<213> ORGANISM: Artificial Sequence
<220> FEATURE:
<223> OTHER INFORMATION: artificial sequence

<400> SEQUENCE: 180
aggaactcca ggatggcatt                                          20

<210> SEQ ID NO 181
<211> LENGTH: 23
<212> TYPE: DNA
<213> ORGANISM: Artificial Sequence
<220> FEATURE:
<223> OTHER INFORMATION: artificial sequence

<400> SEQUENCE: 181
gccgctgccc aatgccatcc tgg                                      23

<210> SEQ ID NO 182
<211> LENGTH: 20
<212> TYPE: DNA
<213> ORGANISM: Artificial Sequence
<220> FEATURE:
<223> OTHER INFORMATION: artificial sequence

<400> SEQUENCE: 182
gccgctgccc aatgccatcc                                          20

<210> SEQ ID NO 183
<211> LENGTH: 23
<212> TYPE: DNA
<213> ORGANISM: Artificial Sequence
<220> FEATURE:
<223> OTHER INFORMATION: artificial sequence

<400> SEQUENCE: 183
gtcagaacat tgaatgcaac tgg                                      23

<210> SEQ ID NO 184
<211> LENGTH: 20
<212> TYPE: DNA
<213> ORGANISM: Artificial Sequence
<220> FEATURE:
<223> OTHER INFORMATION: artificial sequence

<400> SEQUENCE: 184
gtcagaacat tgaatgcaac                                          20

<210> SEQ ID NO 185
<211> LENGTH: 23
<212> TYPE: DNA

```
<213> ORGANISM: Artificial Sequence
<220> FEATURE:
<223> OTHER INFORMATION: artificial sequence

<400> SEQUENCE: 185
tcagaacatt gaatgcaact ggg                                          23

<210> SEQ ID NO 186
<211> LENGTH: 20
<212> TYPE: DNA
<213> ORGANISM: Artificial Sequence
<220> FEATURE:
<223> OTHER INFORMATION: artificial sequence

<400> SEQUENCE: 186
acagaacatt gaatgcaact                                              20

<210> SEQ ID NO 187
<211> LENGTH: 23
<212> TYPE: DNA
<213> ORGANISM: Artificial Sequence
<220> FEATURE:
<223> OTHER INFORMATION: artificial sequence

<400> SEQUENCE: 187
cagaacattg aatgcaactg ggg                                          23

<210> SEQ ID NO 188
<211> LENGTH: 20
<212> TYPE: DNA
<213> ORGANISM: Artificial Sequence
<220> FEATURE:
<223> OTHER INFORMATION: artificial sequence

<400> SEQUENCE: 188
gagaacattg aatgcaactg                                              20

<210> SEQ ID NO 189
<211> LENGTH: 23
<212> TYPE: DNA
<213> ORGANISM: Artificial Sequence
<220> FEATURE:
<223> OTHER INFORMATION: artificial sequence

<400> SEQUENCE: 189
aatactggca tctgtttttg agg                                          23

<210> SEQ ID NO 190
<211> LENGTH: 20
<212> TYPE: DNA
<213> ORGANISM: Artificial Sequence
<220> FEATURE:
<223> OTHER INFORMATION: artificial sequence

<400> SEQUENCE: 190
aatactggca tctgtttttg                                              20

<210> SEQ ID NO 191
<211> LENGTH: 23
<212> TYPE: DNA
<213> ORGANISM: Artificial Sequence
<220> FEATURE:
<223> OTHER INFORMATION: artificial sequence

<400> SEQUENCE: 191
aacagatgcc agtattctac agg                                          23
```

<210> SEQ ID NO 192
<211> LENGTH: 20
<212> TYPE: DNA
<213> ORGANISM: Artificial Sequence
<220> FEATURE:
<223> OTHER INFORMATION: artificial sequence

<400> SEQUENCE: 192
aacagatgcc agtattctac                                                   20

<210> SEQ ID NO 193
<211> LENGTH: 23
<212> TYPE: DNA
<213> ORGANISM: Artificial Sequence
<220> FEATURE:
<223> OTHER INFORMATION: artificial sequence

<400> SEQUENCE: 193 caattttttcc tgtagaatac tgg                                              23

<210> SEQ ID NO 194
<211> LENGTH: 20
<212> TYPE: DNA
<213> ORGANISM: Artificial Sequence
<220> FEATURE:
<223> OTHER INFORMATION: artificial sequence

<400> SEQUENCE: 194
gaatttttcc tgtagaatac                                                   20

<210> SEQ ID NO 195
<211> LENGTH: 23
<212> TYPE: DNA
<213> ORGANISM: Artificial Sequence
<220> FEATURE:
<223> OTHER INFORMATION: artificial sequence

<400> SEQUENCE: 195
cagtattcta caggaaaaat tgg                                               23

<210> SEQ ID NO 196
<211> LENGTH: 20
<212> TYPE: DNA
<213> ORGANISM: Artificial Sequence
<220> FEATURE:
<223> OTHER INFORMATION: artificial sequence

<400> SEQUENCE: 196
gagtattcta caggaaaaat                                                   20

<210> SEQ ID NO 197
<211> LENGTH: 23
<212> TYPE: DNA
<213> ORGANISM: Artificial Sequence
<220> FEATURE:
<223> OTHER INFORMATION: artificial sequence

<400> SEQUENCE: 197
agtattctac aggaaaaatt ggg                                               23

<210> SEQ ID NO 198
<211> LENGTH: 20
<212> TYPE: DNA
<213> ORGANISM: Artificial Sequence
<220> FEATURE:

```
<223> OTHER INFORMATION: artificial sequence

<400> SEQUENCE: 198
agtattctac aggaaaaatt                                              20

<210> SEQ ID NO 199
<211> LENGTH: 23
<212> TYPE: DNA
<213> ORGANISM: Artificial Sequence
<220> FEATURE:
<223> OTHER INFORMATION: artificial sequence

<400> SEQUENCE: 199
aattgggaag cctgaatctg cgg                                          23

<210> SEQ ID NO 200
<211> LENGTH: 20
<212> TYPE: DNA
<213> ORGANISM: Artificial Sequence
<220> FEATURE:
<223> OTHER INFORMATION: artificial sequence

<400> SEQUENCE: 200
aattgggaag cctgaatctg                                              20

<210> SEQ ID NO 201
<211> LENGTH: 23
<212> TYPE: DNA
<213> ORGANISM: Artificial Sequence
<220> FEATURE:
<223> OTHER INFORMATION: artificial sequence

<400> SEQUENCE: 201
tgggaagcct gaatctgcgg tgg                                          23

<210> SEQ ID NO 202
<211> LENGTH: 20
<212> TYPE: DNA
<213> ORGANISM: Artificial Sequence
<220> FEATURE:
<223> OTHER INFORMATION: artificial sequence

<400> SEQUENCE: 202
agggaagcct gaatctgcgg                                              20

<210> SEQ ID NO 203
<211> LENGTH: 23
<212> TYPE: DNA
<213> ORGANISM: Artificial Sequence
<220> FEATURE:
<223> OTHER INFORMATION: artificial sequence

<400> SEQUENCE: 203
aagcctgaat ctgcggtggc agg                                          23

<210> SEQ ID NO 204
<211> LENGTH: 20
<212> TYPE: DNA
<213> ORGANISM: Artificial Sequence
<220> FEATURE:
<223> OTHER INFORMATION: artificial sequence

<400> SEQUENCE: 204
aagcctgaat ctgcggtggc                                              20
```

```
<210> SEQ ID NO 205
<211> LENGTH: 23
<212> TYPE: DNA
<213> ORGANISM: Artificial Sequence
<220> FEATURE:
<223> OTHER INFORMATION: artificial sequence

<400> SEQUENCE: 205
cctgaatctg cggtggcagg agg                                              23

<210> SEQ ID NO 206
<211> LENGTH: 20
<212> TYPE: DNA
<213> ORGANISM: Artificial Sequence
<220> FEATURE:
<223> OTHER INFORMATION: artificial sequence

<400> SEQUENCE: 206
gctgaatctg cggtggcagg                                                  20

<210> SEQ ID NO 207
<211> LENGTH: 23
<212> TYPE: DNA
<213> ORGANISM: Artificial Sequence
<220> FEATURE:
<223> OTHER INFORMATION: artificial sequence

<400> SEQUENCE: 207
cctcctgcca ccgcagattc agg                                              23

<210> SEQ ID NO 208
<211> LENGTH: 20
<212> TYPE: DNA
<213> ORGANISM: Artificial Sequence
<220> FEATURE:
<223> OTHER INFORMATION: artificial sequence

<400> SEQUENCE: 208
gctcctgcca ccgcagattc                                                  20

<210> SEQ ID NO 209
<211> LENGTH: 23
<212> TYPE: DNA
<213> ORGANISM: Artificial Sequence
<220> FEATURE:
<223> OTHER INFORMATION: artificial sequence

<400> SEQUENCE: 209
agctgtcaga cagaaaaaag agg                                              23

<210> SEQ ID NO 210
<211> LENGTH: 20
<212> TYPE: DNA
<213> ORGANISM: Artificial Sequence
<220> FEATURE:
<223> OTHER INFORMATION: artificial sequence

<400> SEQUENCE: 210
agctgtcaga cagaaaaaag                                                  20

<210> SEQ ID NO 211
<211> LENGTH: 23
<212> TYPE: DNA
<213> ORGANISM: Artificial Sequence
<220> FEATURE:
<223> OTHER INFORMATION: artificial sequence
```

```
<400> SEQUENCE: 211
gtcagacaga aaaaagaggt agg                                               23

<210> SEQ ID NO 212
<211> LENGTH: 20
<212> TYPE: DNA
<213> ORGANISM: Artificial Sequence
<220> FEATURE:
<223> OTHER INFORMATION: artificial sequence

<400> SEQUENCE: 212
gtcagacaga aaaaagaggt                                                   20

<210> SEQ ID NO 213
<211> LENGTH: 23
<212> TYPE: DNA
<213> ORGANISM: Artificial Sequence
<220> FEATURE:
<223> OTHER INFORMATION: artificial sequence

<400> SEQUENCE: 213
tcagacagaa aaagaggta ggg                                                23

<210> SEQ ID NO 214
<211> LENGTH: 20
<212> TYPE: DNA
<213> ORGANISM: Artificial Sequence
<220> FEATURE:
<223> OTHER INFORMATION: artificial sequence

<400> SEQUENCE: 214
acagacagaa aaagaggta                                                    20

<210> SEQ ID NO 215
<211> LENGTH: 23
<212> TYPE: DNA
<213> ORGANISM: Artificial Sequence
<220> FEATURE:
<223> OTHER INFORMATION: artificial sequence

<400> SEQUENCE: 215
ggtagggcga cagatctaat agg                                               23

<210> SEQ ID NO 216
<211> LENGTH: 20
<212> TYPE: DNA
<213> ORGANISM: Artificial Sequence
<220> FEATURE:
<223> OTHER INFORMATION: artificial sequence

<400> SEQUENCE: 216
ggtagggcga cagatctaat                                                   20

<210> SEQ ID NO 217
<211> LENGTH: 7
<212> TYPE: PRT
<213> ORGANISM: Artificial Sequence
<220> FEATURE:
<223> OTHER INFORMATION: NLS

<400> SEQUENCE: 217

Pro Lys Lys Lys Arg Lys Val
1               5

<210> SEQ ID NO 218
```

```
<211> LENGTH: 16
<212> TYPE: PRT
<213> ORGANISM: Artificial Sequence
<220> FEATURE:
<223> OTHER INFORMATION: NLS

<400> SEQUENCE: 218

Lys Arg Pro Ala Ala Thr Lys Lys Ala Gly Gln Ala Lys Lys Lys Lys
1               5                   10                  15

<210> SEQ ID NO 219
<211> LENGTH: 27
<212> TYPE: PRT
<213> ORGANISM: Artificial Sequence
<220> FEATURE:
<223> OTHER INFORMATION: HA

<400> SEQUENCE: 219

Tyr Pro Tyr Asp Val Pro Asp Tyr Ala Tyr Pro Tyr Asp Val Pro Asp
1               5                   10                  15

Tyr Ala Tyr Pro Tyr Asp Val Pro Asp Tyr Ala
            20                  25
```

METHOD FOR INDUCING EXON SKIPPING BY GENOME EDITING

PRIORITY AND CROSS REFERENCE TO RELATED APPLICATIONS

This application is the U.S. National Stage Application under 35 U.S.C. § 371 of International Application No. PCT/JP2017/041756, filed Nov. 21, 2017, designating the U.S. and published as WO 2018/179578 A1 on Oct. 4, 2018, which claims the benefit of Japanese Patent Application No. JP 2017-068909, filed Mar. 30, 2017. Any and all applications for which a foreign or a domestic priority is claimed is/are identified in the Application Data Sheet filed herewith and is/are hereby incorporated by reference in their entirety under 37 C.F.R. § 1.57.

SEQUENCE LISTING IN ELECTRONIC FORMAT

The present application is being filed along with an Electronic Sequence Listing as an ASCII text file via EFS-Web. The Electronic Sequence Listing is provided as a file entitled TOYA166026APCSEQLIST.txt, created and last saved on Sep. 27, 2019, which is 69,586 bytes in size. The information in the Electronic Sequence Listing is incorporated herein by reference in its entirety.

TECHNICAL FIELD

The present invention relates to a gene recombination technique, and relates to a method of inducing exon skipping by genome editing, which method is useful in the field of research and the field of medicine.

BACKGROUND ART

Duchenne muscular dystrophy (hereinafter referred to as DMD) is a disease causing atrophy of muscle fibers due to loss of function of the dystrophin gene. The skeletal muscle isoform (Dp427m) of the dystrophin gene is constituted by 79 exons. In cases where shifting of the reading frame occurs in this gene due to partial deletion of the exons or the like, normal production of the dystrophin protein becomes impossible, leading to development of DMD (Non-patent Document 1).

Aiming at radical cure of DMD, various studies have been carried out for gene therapies in which a functional exogenous dystrophin gene is added to replace a dysfunctional endogenous dystrophin gene. Since the full-length cDNA of dystrophin has a size of as long as 14 kb, attempts are being made to reduce its size by elimination of unnecessary domain portions, and to introduce the thus prepared minidystrophin or microdystrophin into muscular tissue using various vectors for gene transfer (AAV, lentivirus, Sleeping Beauty transposon vectors, and the like). However, since introduction of a huge gene is difficult, no effective therapeutic method has been established so far.

In a study in progress, an antisense oligonucleotide is used to prevent reading of part of a particular exon during splicing of mRNA in order to restore dystrophin having the normal function (exon skipping). However, since the antisense oligonucleotide is only temporarily effective, a method for repairing the gene itself has been demanded for the radical cure.

As methods for repairing the gene itself, genome editing techniques such as TALEN and CRISPR-Cas systems have recently been developed. In these techniques, a particular sequence position is recognized in the genome sequence, and then DNA double-strand break is induced to cause local induction of a DNA repair mechanism through non-homologous recombination (non-homologous end joining, NHEJ) or homologous recombination (homology directed repair, HDR), thereby enabling addition of a base(s) to or deletion of a base(s) from the cleaved site.

For CRISPR-Cas genome editing techniques, the type II and type V CRISPR systems of bacteria and archaebacteria are widely used. They can bind to a target DNA dependently on a spacer sequence contained in a guide RNA (gRNA or sgRNA), to induce a double-strand DNA break by the action of a Cas nuclease (Cas9 in cases of type II, and Cpf1 in cases of type V). In the type II CRISPR system, the guide RNA is a complex containing crRNA and tracrRNA, or an sgRNA (single guide RNA) containing crRNA and tracrRNA linked to each other.

It has been reported that exon skipping for dystrophin using a genome editing technique was carried out in myoblasts [Non-patent Documents 2 and 3] or at the mdx mouse level [Non-patent Documents 4 to 7].

In these studies, both ends of the exon to be skipped are cleaved using two guide RNAs, to induce a large deletion including the whole exon. However, such a method increases the risk of non-specific cleavage since two gRNAs are required. Moreover, cleavage by only one of the gRNAs cannot induce exon skipping, and the two gRNA sequences need to act in the same genome. Moreover, at least several hundred bases need to be deleted, and, in cases where the region contains an unknown regulatory region or miRNA-coding region, there is a risk of occurrence of unexpected side effects.

On the other hand, the present inventors have previously reported that, by using a genome editing technique such as TALEN or CRISPR-Cas9 in iPS cells derived from DMD patients, a dystrophin gene mutation can be repaired by (1) exon skipping, (2) frameshift induction, and (3) knock-in of a deleted exon [Non-patent Document 8]. Among these, the method of (1) employs a method in which the splice acceptor of the exon is deleted. Since exon skipping can be sufficiently induced in cases where deletion of several bases to several ten bases can be induced with one gRNA, the method is superior to the methods reported by [Non-patent Documents 2 to 7] in terms of the three facts: a higher efficiency, a smaller risk of side-effect mutations, and requirement of only small DNA base deletion.

On the other hand, although a splice acceptor is an attractive target site for induction of exon skipping, it contains a polypyrimidine sequence (consecutive T/C's), and similar sequences are contained in a large number of exon sequences. Therefore, the method has a problem in that a gRNA having a high specificity cannot be easily designed. The double-nicking method, in which the specificity is increased by combination of two units of nickase-modified CRISPR-Cas containing a mutation introduced into the DNA cleavage domain of CRISPR-Cas such that a single-strand break rather than a DNA double-strand break is induced [Mali P et al., Nat Biotechnol. 2013 September; 31(9): 833-8.] [Ran F A et al., Cell. 2013 Sep. 12; 154(6): 1380-9.], is known. Since type V AsCpf1 is known to have a higher specificity than Type II SpCas9 in human cells [Kleinstiver B P et al., Nat Biotechnol, 2016 August; 34(8): 869-74.|Kim D et al., Nat Biotechnol, 2016 August; 34(8): 863-8.], it is thought that the problem of the specificity can be avoided by targeting a site near the splicing acceptor using the double-nicking method or Cpf1.

It is also known that the cleavage activity and the cleavage length vary depending on the spacer sequence in the guide RNA and the type of the CRISPR-Cas, and guide sequences and design methods that enable efficient induction of exon skipping have been empirically unknown.

PRIOR ART DOCUMENTS

Non-Patent Documents

[Non-patent Document 1] Pichavant et al., Mol Ther. 2011 May; 19(5): 830-40.
[Non-patent Document 2] Ousterout D G et al., Nat Commun. 2015 Feb. 18; 6: 6244
[Non-patent Document 3] Iyombe-Engembe J P Mol Ther Nucleic Acids. 2016 Jan. 26; 5: e283.
[Non-patent Document 4] Xu L et al., Mol Ther. 2016 March; 24(3): 564-9.
[Non-patent Document 5] Long C et al., Science, 2016 Jan. 22; 351(6271): 400-3.
[Non-patent Document 6] Nelson C E et al., Science. 2016 Jan. 22; 351(6271): 403-7
[Non-patent Document 7] Tabebordbar M et al., Science. 2016 Jan. 22; 351(6271): 407-11
[Non-patent Document 8] Li H L et al., Stem Cell Reports. 2015 Jan. 13; 4(1): 143-54.

SUMMARY

An object of the present invention is to provide an efficient method of exon skipping. Another object of the present invention is to provide a simple method of evaluation of exon skipping.

The present inventors intensively studied to solve the above problems. The present inventors discovered that, by using, as a target gene for exon skipping, a marker gene containing a sequence which is inserted in a coding region and which contains a first intron, an exon to be analyzed, and a second intron, and by designing the marker gene such that the marker gene functions when the exon to be analyzed is skipped, the exon skipping can be efficiently analyzed based on the phenotype of the marker gene. As a result, the present inventors discovered that, when targeted exon skipping is carried out for a gene of interest in a genome using CRISPR-Cas and guide RNA, by arranging the guide RNA such that the site of cleavage by the CRISPR-Cas is positioned within 80 bases from the splice acceptor site or the splice donor site of the target exon, the efficiency of the exon skipping can be increased, thereby completing the present invention.

More specifically, the present invention provides the followings.

[1] A method of skipping a target exon of a gene of interest in a genome, comprising using CRISPR-Cas and guide RNA, wherein the guide RNA contains a spacer sequence such that the site of cleavage by the CRISPR-Cas is positioned within 80 bases from the splice acceptor site immediately before the target exon or the splice donor site immediately after the target exon.
[2] The method according to [1], wherein two or more kinds of the guide RNA are used.
[3] The method according to [1], wherein the CRISPR-Cas is a nickase-modified Cas containing a substitution in the nuclease activity residue in the RuvC domain, and wherein a guide RNA for the sense strand and a guide RNA for the antisense strand of the gene of interest are used, the guide RNAs containing spacer sequences such that the cleavage site in the sense strand of the gene of interest and the cleavage site in the antisense strand of the gene of interest are both positioned within 80 bases from the splice acceptor site immediately before the target exon or the splice donor site immediately after the target exon.
[4] The method according to any one of [1] to [3], wherein the CRISPR-Cas is Cas9.
[5] The method according to [4], wherein the Cas9 is derived from *Streptococcus pyogenes*, or derived from *Staphylococcus aureus*.
[6] The method according to any one of [1] to [3], wherein the CRISPR-Cas is Cpf1.
[7] The method according to [6], wherein the Cpf1 is derived from *Acidaminococcus* sp. BV3L6, or derived from Lachnospiraceae.
[8] The method according to any one of [1] to [7], wherein the gene of interest is a human dystrophin gene.
[9] The method according to [8], wherein the target exon is exon 45.
[10] The method according to [9], wherein the guide RNA contains a spacer sequence having the base sequence of bases from 17 to 36 in the base sequence of any of SEQ ID NOs:17 to 42, the base sequence of bases from 17 to 39 in the base sequence of any of SEQ ID NOs:44 to 45, or the base sequence of bases from 24 to 43 in the base sequence of any of SEQ ID NOs:50 to 53.
[11] A reagent for skipping a target exon of a gene of interest in a genome, comprising CRISPR-Cas and guide RNA, wherein the guide RNA contains a spacer sequence such that the site of cleavage by the CRISPR-Cas is positioned within 80 bases from the splice acceptor site immediately before the target exon or the splice donor site immediately after the target exon.
[12] A method of evaluating exon skipping, comprising using a marker gene containing a sequence which is inserted in a coding region and which contains a first intron, an exon to be analyzed, and a second intron, wherein the marker gene is designed such that the marker gene functions when the exon to be analyzed is skipped.
[13] The method according to [12], wherein the exon skipping is exon skipping using CRISPR-Cas and guide RNA.
[14] The method according to [12] or [13], wherein a transposon vector is used for inserting the marker gene into the genome of a cell to be analyzed.
[15] The method according to any one of [12] to [14], wherein the marker gene is a luciferase gene.
[16] The method according to any one of [12] to [15], wherein the exon to be analyzed is exon 45 of a human dystrophin gene.

According to the method of the present invention, the efficiency of exon skipping can be increased in exon skipping utilizing a genome editing technique, so that the method is effective for treatment of diseases and the like. Further, by using, as a target gene for the exon skipping, a marker gene containing a sequence which is inserted in a coding region and which contains a first intron, an exon to be analyzed, and a second intron, and by designing the marker gene such that the marker gene functions when the exon is skipped, the exon skipping can be efficiently analyzed based on the phenotype of the marker gene.

BRIEF DESCRIPTION OF THE DRAWINGS

FIG. 3 shows part of the sequence of a reporter vector for detection of the exon skipping efficiency for the dystrophin gene. The sequence was designed by finding "CAG|G", which is the sequence most frequently found as an exon-exon junction, in the middle of cDNA of the firefly luciferase gene, and then placing, at this position, a sequence around the splicing donor (SD) immediately after exon 44 of the dystrophin gene ("+" symbols), exon 45 (">" symbols) and intron sequences before and after it, and a splice acceptor (SA) sequence immediately before exon 46 ("+" symbols), in that order. The restriction enzyme sites (NarI, AgeI, and SalI) used for the construction of the vector are indicated with "#" symbols.

FIG. 4 shows alteration of the Luc sequence by introduction of a mutation, which alteration was carried out such that splicing occurs only at the inserted dystrophin sequence portion. Panel (a) shows the result of observation of the splicing pattern, which observation was carried out by introducing the exon skipping vector of FIG. 3 into 293T cells, extracting mRNA therefrom, and then performing the Sanger sequencing method. As a result, it was found that a pseudo-splicing donor sequence is present in the middle (at the 31th base in FIG. 3) of the Luc gene, causing unexpected splicing (the presence of an extra wave in the sequence electrogram). Panel (b) shows the result of an analysis that was carried out by obtaining the entire exon sequences of the dystrophin gene from Ensemble BioMart, and then analyzing the consensus sequences of the splicing donor portions and the splice acceptor portions using WebLogo. As a result, trends of base sequences similar to those of common human gene base sequences were found, and it could be confirmed that the "GT" sequence is conserved with the highest frequency among splicing donors, and that "AG" is conserved with the highest frequency among splice acceptor sequences. Panel (c) shows alteration of "G" at the 967th position as counted from the first base of the Luc cDNA (the 31st base in FIG. 3) to "A", which alteration was carried out in order to prevent the pseudo-splicing donor sequence of (a) from functioning. By this, the Val amino acid at the 323rd position of the Luc protein was changed to Ile.

FIG. 13a shows target sequences of gRNAs derived from various kinds of CRISPR-Cas (SpCas9, SaCas9, and AsCpf1), which were designed for positions near the splice acceptor site of dystrophin exon 45. The PAM sequence is indicated with an underline.

FIG. 14a shows 26 kinds of gRNAs prepared for target sites of SpCas9-gRNA which can be designed in dystrophin exon 45.

FIG. 14b shows a list of the target sequences and the spacer sequences of sgRNA-DMD1 to 26 used in FIG. 14a. Each gRNA was introduced into 293T cells together with an SpCas9 expression vector and a Luc2 (G967A)+hEx45 (0.7 kb) exon skipping reporter vector, and a T7E1 assay was carried out using the following primers: (Luc2-Fwd-Splice: TGCCCACACTATTTAGCTTC (SEQ ID NO:1), Luc2-Rev-Splice: GTCGATGAGAGCGTTTGTAG) (SEQ ID NO:2)), to measure the DNA cleavage activity for the target site of each gRNA in the reporter vector (T7E1 Indel activity [%]). In addition, the exon skipping efficiency was also measured (Exon skipping Luc activity [A.U.]).

FIG. 15 shows the results of evaluation of the exon skipping efficiencies using SpCas9 in the same manner as in FIG. 14b, which evaluation was carried out for combinations of two kinds of sgRNAs used in FIG. 14b.

DETAILED DESCRIPTION

Figure 1:
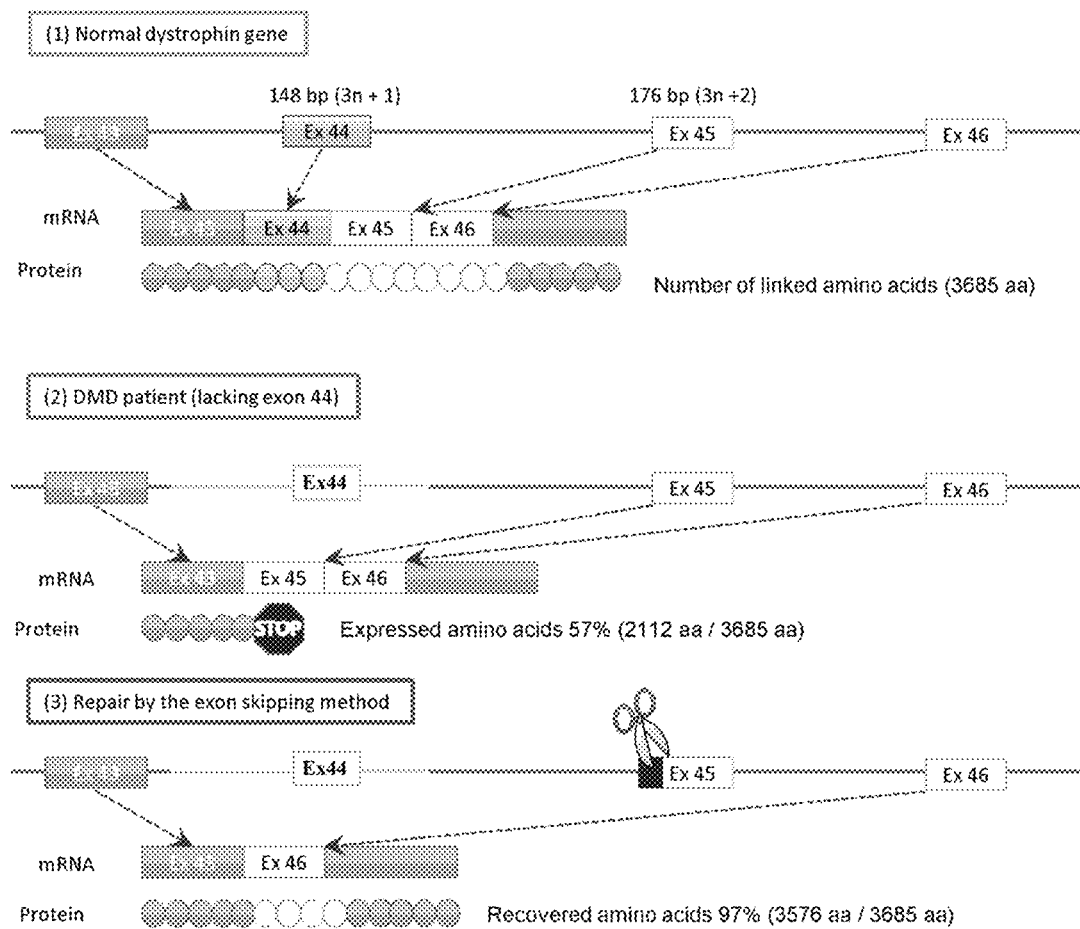
FIG. 1 shows the principle of repair of dystrophin protein by a genome editing exon skipping method.

The method of the present invention is a method of skipping a target exon of a gene of interest in a genome, comprising using CRISPR-Cas and guide RNA, wherein the guide RNA contains a spacer sequence such that the site of cleavage by the CRISPR-Cas is positioned within 80 bases from the splice acceptor site immediately before the target exon or the splice donor site immediately after the target exon.

<CRISPR-Cas Systems>

As CRISPR systems, class 1, which acts as a complex formed by a plurality of factors, and class 2, which acts even as a single factor, are known. Examples of class 1 include type I, type III, and type IV, and examples of class 2 include type II, type V, and type VI (Makarova K S et al., Nat Rev Microbiol. 2015|Mohanraju P et al., Science, 2016). At present, for use in genome editing in mammalian cells, class 2 CRISPR-Cas, which acts as a single factor, is mainly used. Representative examples of the class 2 CRISPR-Cas include type II Cas9 and type V Cpf1.

As a CRISPR-Cas9 system, class 2 type II Cas9 derived from *Streptococcus pyogenes*, which is widely used as a genome editing tool, may be used. Class 2 type II Cas9 systems derived from other bacteria have also been reported, and, for example, Cas9 derived from *Staphylococcus aureus* (Sa), Cas9 derived from *Neisseria meningitidis* (Nm), or Cas9 derived from *Streptococcus thermophilus* (St) may also be used.

[I]
An updated evolutionary classification of CRISPR-Cas systems.
Makarova K S, Wolf Y I, Alkhnbashi O S, Costa F, Shah S A, Saunders S J, Barrangou R, Brouns S J, Charpentier E, Haft D H, Horvath P, Moineau S, Mojica F J, Terns R M, Terns M P, White M F, Yakunin A F, Garrett R A, van der Oost J, Backofen R, Koonin E V.
Nat Rev Microbiol. 2015 November; 13(11): 722-36. doi: 10.1038/nrmicro3569.

[II]
Diverse evolutionary roots and mechanistic variations of the CRISPR-Cas systems. Mohanraju P, Makarova K S, Zetsche B, Zhang F, Koonin E V, van der Oost J. Science. 2016 Aug. 5; 353(6299):aad5147. doi: 10.1126/science.aad5147

[III] In vivo genome editing using *Staphylococcus aureus* Cas9. Nature. 2015 Apr. 9; 520(7546): 186-91.

[IV] Orthogonal Cas9 proteins for RNA-guided gene regulation and editing. Nat Methods. 2013 November; 10(11): 1116-21.

[V] Efficient genome engineering in human pluripotent stem cells using Cas9 from *Neisseria meningitidis*. Proc Natl Acad Sci USA. 2013 Sep. 24; 110(39): 15644-9.

[VI] *Streptococcus thermophilus* CRISPR-Cas9 systems enable specific editing of the human genome. Mol Ther. 2016 March; 24(3): 636-44.

Further, as a class 2 type V CRISPR-Cas system, Cpf1 has been identified, and it is reported that, by using Cpf1 derived from *Acidaminococcus* sp. (As) or Cpf1 derived from Lachnospiraceae, genome editing in human cells is possible dependently on the gRNA sequence. Thus, these kinds of CRISPR-Cpf1 may also be used.

[V] Cpf1 Is a Single RNA-Guided Endonuclease of a Class 2 CRISPR-Cas System. Cell. 2015 Oct. 22; 163(3): 759-71

[VI] Multiplex gene editing by CRISPR-Cpf1 using a single crRNA array. Nat Biotechnol. 2017 January; 35(1): 31-34.

CRISPR-Cas9 has two nuclease domains, the RuvC domain and the HNH domain, each of which is involved in cleavage of one strand of the double-stranded DNA. CRISPR-Cpf1 has the RuvC domain and the Nuc domain. In cases where Asp at the 10th position in the RuvC domain of Cas9 derived from *Streptococcus pyogenes* is substituted with Ala (D10A), no cleavage occurs in the DNA strand to which the gRNA does not bind. In cases where His at the 840th position in the HNH domain is substituted with Ala (H840A), no cleavage occurs in the DNA strand to which the gRNA binds [Jinek M et al., Science. 2012 Aug. 17; 337 (6096): 816-21.]. This property was used for development of the double nicking (or paired nickases) method, in which nickases each of which cleaves only one strand of a double-stranded DNA are used, in a state where they are positioned close to each other, to cleave the respective separate DNA strands, to induce a DNA double-strand break in a target region [Mali P et al., Nat Biotechnol. 2013 September; 31(9): 833-8.] [Ran F A et al., Cell. 2013 Sep. 12; 154(6): 1380-9.]. By this, genome editing such as targeting by insertion of an arbitrary sequence by knock-in became possible while the risk of inducing a sequence mutation at a site other than the target site was reduced [WO 2014204725 A1].

Thus, in the method of the present invention, D10A Cas9 nickase may be used as CRISPR-Cas9, and two kinds of guide RNAs for cleavage of the sense strand and the antisense strand, respectively, may be used (double nicking method). A nickase-type Cas9 or a nickase-type Cpf1 applicable to the double nicking method can be obtained also by introducing a mutation to an active amino acid residue of the RuvC domain of a system other than the Cas9 derived from *Streptococcus pyogenes*.

A DNA encoding the above CRISPR-Cas can be obtained by performing cloning based on a sequence encoding CRISPR-Cas deposited in GenBank or the like. Further, a commercially available plasmid containing CRISPR-Cas may be obtained from Addgene or the like and used; a DNA encoding CRISPR-Cas may be obtained by PCR using the plasmid as a template, or the DNA may be artificially prepared using an artificial gene synthesis technique known to those skilled in the art. The method of obtaining the DNA is not limited. A DNA encoding Cas nickase may be obtained by introducing a mutation to an active amino acid residue of a nuclease domain of CRISPR-Cas by a known molecular biological technique, or may be obtained by cloning from a plasmid or the like containing a CRISPR-Cas gene to which a mutation was introduced in advance. Further, in order to increase the expression efficiency of the CRISPR-Cas in the host, codon alteration may be carried out.

The CRISPR-Cas may be introduced into the cell as mRNA, protein, or DNA. The guide RNA may be introduced into the cell as RNA or DNA. In cases of introduction using a vector, examples of the vector include vectors capable of replicating in eukaryotic cells, vectors capable of maintaining an episome, and vectors that can be incorporated into the host cell genome. Examples of virus vectors therefor include adenovirus vectors, retrovirus vectors, lentivirus vectors, Sendai virus vectors, and adeno-associated virus vectors. Examples of transposon vectors therefor include piggyBac vectors, piggyBat vectors, Sleeping Beauty vectors, TolII vectors, and LINE vectors. For treatment, introduction using a vector showing constant expression is not preferred because of an increased risk of side effects. Since treatment requires induction of DNA cleavage only immediately after the administration, introduction as Cas9 mRNA/gRNA or Cas9 protein/gRNA, introduction as an episomal vector, or the like is preferred.

The vector may contain a selection marker. The "selection marker" means a genetic element that provides a selectable phenotype to the cell into which the selection marker is introduced. The selection marker is generally a gene whose gene product gives resistance to an agent which inhibits growth of cells or which kills cells. Specific examples of the selection marker include the Puro resistance gene, Neo resistance gene, Hyg resistance gene, Bls gene, hisD gene, Gpt gene, and Ble gene. Examples of drugs useful for selecting the presence of selection markers include puromycin for the Puro resistance gene, G418 for the Neo resistance gene, hygromycin for the Hyg resistance gene, blasticidin for the Bls gene, histidinol for hisD, xanthine for Gpt, and bleomycin for Ble.

<Guide RNA>

A guide RNA (gRNA or sgRNA) is a complex containing tracrRNA and crRNA, or tracrRNA and crRNA artificially linked to each other, in the CRISPR-Cas9 method. [Jinek M et al., Science. 2012 Aug. 17; 337(6096): 816-21.] In the present invention, the guide RNA means a product prepared by linking a spacer sequence having a sequence corresponding to the gene of interest to a scaffold sequence.

As the scaffold sequence of the guide RNA of SpCas9, a known sequence, for example, the sequence of 5'-GTTT-TAGAGCTAGAAATAGCAAGT-TAAAATAAGGCTAGTCCGTTATCAA CTT-GAAAAAGTGGCACCGAGTCGGTGCTTTTTTT-3' (SEQ ID NO:3) can be used. Alternatively, an altered scaffold sequence (Chen B et al., Cell, 2013 Dec. 19; 155(7): 1479-91) 5'-GTTTTAGAGCTATGCTGGAAACAGCAT-AGCAAGTTAAAATAAGGCTAGT CCGTTATCAACTT-GAAAAAGTGGCACCGAGTCGGTGCTTTTTTTT-3' (SEQ ID NO:4) may be used.

The guide RNA does not require tracrRNA in CRISPR-Cpf1.

As the scaffold sequence of the guide RNA of AsCpf1, a known sequence, for example, the sequence of 5'-GTAAT- TTCTACTCTTGTAGAT-3' (SEQ ID NO:5) or 5'-GGGTAATTTCTACTCTTGTAGAT-3' (SEQ ID NO:6) can be used. The DNA may be, for example, artificially prepared using an artificial gene synthesis technique known to those skilled in the art. The method of obtaining the DNA is not limited.

In the method of the present invention, the spacer sequence of the guide RNA is arranged such that the site of cleavage by the CRISPR-Cas is positioned within 80 bases, preferably within 50 bases, more preferably within 30 bases, from the splice acceptor site immediately before the target exon or the splice donor site immediately after the target exon. It may also be designed for the exonic splicing enhancer (ESE) sequence portion.

With such arrangement, cleavage occurs at a position near the splice acceptor site or the donor site of the target exon, and the splice acceptor site or the donor site is disrupted in the repair process, resulting occurrence of skipping of the target exon when the splicing reaction occurs in the process of maturation of pre-mRNA into mRNA.

The splice acceptor site is defined as the two bases immediately before the target exon, and its examples include the AG sequence.

The splice donor site is defined as the two bases immediately after the target exon, and its examples include the GT sequence.

The exonic splicing enhancer (ESE) sequence is defined as a binding site of SR protein (SRSF1 to 12 genes) present in the target exon. The binding site of SR protein can be obtained by searching databases, and examples of such databases include RESCUE-ESE [Fairbrother W G et al., Science, 2002] and ESEfinder [Cartegni L. et al., NAR, 2003].

The spacer sequence of Type II Cas9 can be designed as RNA having a continuous base sequence of 15 to 30 bases whose 3'-end corresponding to the base immediately before the PAM sequence (for example, NGG in the case of *S. pyogenes* Cas9, or NNGRRT in the case of *Staphylococcus aureus* Cas9) in the sequence of the sense strand or the antisense strand of the gene of interest (for example, NNNNNNNNNNNNNNNNNNNNGG (SEQ ID NO:7)). (The N's represent the spacer sequence.)

However, since the cleavage occurs even without 100% matching of the sequence, a mismatch(es) of one or two bases is/are acceptable (especially in the 5'-side). For a transcription start site from the human H1 PolIII promoter, the 5'-end of the spacer sequence is preferably not C or T. In cases where the corresponding base in the genome is C or T, it is preferably converted to G.

The spacer sequence of the guide RNA of type V Cfp1 can be designed as RNA having a continuous base sequence of 15 to 30 bases whose 5'-end corresponds to the base immediately after the PAM sequence (for example, TTTV in the case of *Acidaminococcus* sp. Cpf1) (for example, TTTTVNNNNNNNNNNNNNNNNNNNN (SEQ ID NO:8)). In the case of Cpf1, tracrRNA is not required.

Regarding the site of DNA cleavage by *S. pyogenes* Cas9, the cleavage occurs between the third base and the fourth base as counted in the 3'→5' direction from the 3'-end base of the spacer sequence, which is regarded as 1. Accordingly, "the cleavage site is positioned within 80 bases from the acceptor site or donor site of the target exon" means that the number of bases present between the bases at the acceptor site or the donor site (for example, GT or AG (in the case of the antisense strand, AC or CT)) and the fourth base as counted in the 3'→5' direction from the base corresponding to the 3'-end base of the spacer sequence is not more than 80 bases.

Regarding the site of DNA cleavage by AsCpf1, the cleavage occurs at the 19th sense-strand base and the 23rd antisense-strand base as counted in the 5'-3' direction from the 5'-end base of the spacer sequence, which is regarded as 1.

Figure 3:
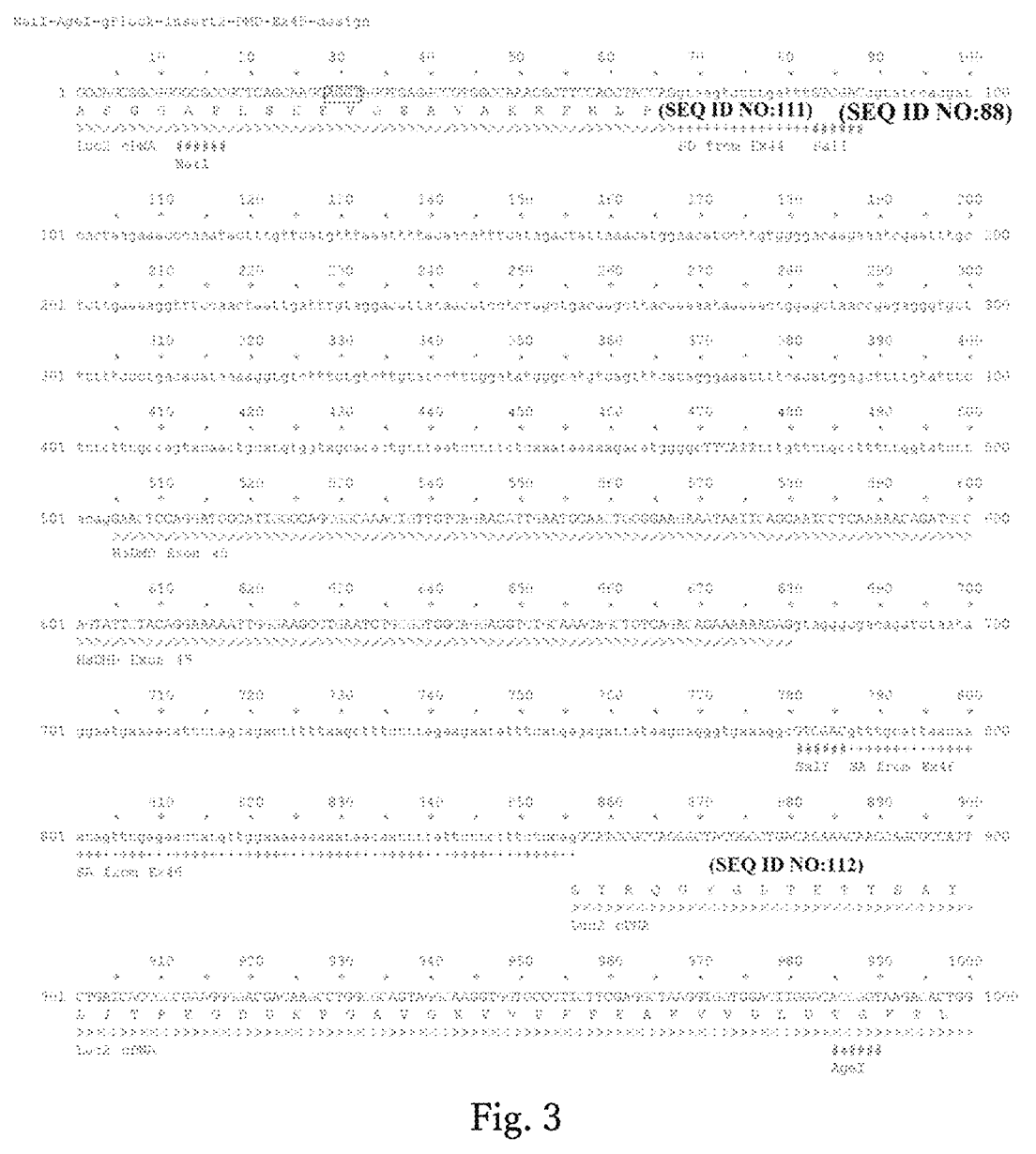

A description is given with reference to FIG. 3.

Using exon 45 of the human dystrophin (hDMD) gene as a target, the acceptor site immediately before the exon 45 is disrupted to carry out skipping of the exon 45.

In this process, in Sp-sgRNA-DMD1, a spacer sequence corresponding to the 20 bases immediately before the PAM sequence (AGG) (tggtatcttacagGAAC/TCC) (SEQ ID NO:9) is designed. In this case, there are four bases between the acceptor sequence (ag) and the cleavage site (C/T).

Similarly, in Sp-sgRNA-DMD2, a spacer sequence corresponding to the 20 bases immediately before the PAM sequence (TGG) (atcttacagGAACTCCA/GGA) (SEQ ID NO:10) is designed. In this case, there are eight bases between the acceptor sequence (ag) and the cleavage site (A/G).

Similarly, in Sp-sgRNA-DMD3, a spacer sequence corresponding to the 20 bases immediately before the PAM sequence (TGG) (cagGAACTCCAGGATGG/CAT) (SEQ ID NO:11) is designed. In this case, there are 14 bases between the acceptor sequence (ag) and the cleavage site (G/C).

Similarly, in Sp-sgRNA-DMD4, a spacer sequence corresponding to the 20 bases immediately before the PAM sequence (CGG) (TCCAGGATGGCATTGGG/CAG) (SEQ ID NO:12) is designed. In this case, there are 21 bases between the acceptor sequence (ag) and the cleavage site (G/C).

Sp-sgRNA-DMD5 is arranged for the antisense strand, and a spacer sequence corresponding to the 20 bases immediately before the PAM sequence (AGG) (GTTCctgtaagatacca/aaa) (SEQ ID NO:13) is designed.

In this case, there are 11 bases between the acceptor sequence (ct) and the cleavage site (a/a).

In each sequence ID number, T is read as U when an RNA sequence is meant.

By adding a scaffold sequence to the above spacer sequence, a guide RNA can be obtained. Plasmids which contains a scaffold sequence therein, and with which a desired guide RNA can be expressed by inserting a DNA sequence corresponding to an arbitrary spacer sequence, are commercially available (for example, Addgene plasmid 41824), and they can be simply used for introduction of a guide RNA into cells.

Two or more kinds of guide RNAs may be used. In such a case, two or more kinds of guide RNAs satisfying the condition "the site of cleavage by the CRISPR-Cas is positioned within 80 bases from the splice acceptor site immediately before the target exon or the splice donor site immediately after the target exon" may be used for one site to be disrupted (target exon). By using two or more different kinds of guide RNAs for the same site to be disrupted, and causing DNA double-strand breaks simultaneously at two or more sites, exon skipping can be caused with a very high efficiency. The two or more kinds of guide RNAs may be arranged either for one of the sense strand and the antisense strand, or for both of these.

In cases where D10A Cas9 nickase is used, and two kinds of guide RNAs for cleaving the sense strand and the antisense strand, respectively, are used, the two kinds of guide RNAs are designed such that they satisfy the requirement that the cleavage site of at least one of them is positioned within 80 bases from the acceptor site or the donor site before or after the target exon. In this case, the distance between the guide RNA-binding site (spacer sequence) in the sense strand and the guide RNA-binding site (spacer sequence) in the antisense strand is preferably −10 to 200 bases, more preferably 0 to 100 bases. The acceptor site or the donor site is preferably located between the cleavage site in the sense strand and the cleavage site in the antisense strand. The spacer sequence of the guide RNA for cleavage of the sense strand and the spacer sequence of the guide RNA for cleavage of the antisense strand may overlap with each other, but they preferably do not overlap with each other.

The gene of interest having the target exon is not limited. It is preferably a mammalian gene, more preferably a human gene, for example, a disease-associated gene.

One example of the gene is the dystrophin gene, which is a causative gene of Duchenne muscular dystrophy. Since it is known that the phenotype of the mutant gene can be masked by skipping of exon 45, exon 45 of the human dystrophin gene can be suitably used as a target of exon skipping.

The gene of interest may also be an artificially synthesized gene containing an exon and an intron.

Specific examples of the spacer sequence contained in the guide RNA that can be used in the method of the present invention include the base sequence of bases from 17 to 36 in the base sequence of any of SEQ ID NOs:17 to 42, the base sequence of bases from 17 to 39 in the base sequence of any of SEQ ID NOs:44 to 45, and the base sequence of bases from 24 to 43 in the base sequence of any of SEQ ID NOs:50 to 53. Their complementary sequences may also be used.

Among these, when two kinds of guide RNAs are used in combination, preferred examples of the combination of the spacer sequences include the combinations of sgRNA-DMD1 (the base sequence of bases from 17 to 36 in SEQ ID NO:17), sgRNA-DMD2 (the base sequence of bases from 17 to 36 in SEQ ID NO:18), sgRNA-DMD4 (the base sequence of bases from 17 to 36 in SEQ ID NO:20), sgRNA-DMD8 (the base sequence of bases from 17 to 36 in SEQ ID NO:24), or sgRNA-DMD9 (the base sequence of bases from 17 to 36 in SEQ ID NO:25) with sgRNA-DMD23 (the base sequence of bases from 17 to 36 in SEQ ID NO:39).

Further, among these, preferred examples of the combination of the spacer sequences for use in the double nicking method include sgRNA-DMD4 (the base sequence of bases from 17 to 36 in SEQ ID NO:20) and sgRNA-DMD5 (the base sequence of bases from 17 to 36 in SEQ ID NO:21).

Transfection of cells with DNA, RNA, or vectors expressing these can be carried out by using known arbitrary means, and commercially available transfection reagents may be used. For example, Lipofectamine 2000 (Thermo Fisher), StemFect (STEMGEN), FuGENE 6/HD (Promega), jetPRIME Kit (Polyplus-transfection), DreamFect (OZ Biosciences), GenePorter 3000 (OZ Biosciences), or Calcium Phosphate Transfection Kit (OZ Biosciences) can be used. Electroporation may be also used. For example, NEPA21 (Nepa Gene), 4D-Nucleofector (Lonza), Neon (Thermo Fisher), Gene Pulser Xcell (BioRad), or ECM839 (BTX Harvard Apparatus) can be used. Regarding the transfection of cells, a complex may be formed with CRISPR-Cas protein and gRNA in advance, and the cells may then be transfected with the complex. Further, microinjection or electroporation may be carried out for introduction of the DNA or RNA into fertilized eggs.

The cells are preferably a mammalian cells, more preferably human cells. The cells may be primary cultured cells isolated from an established cell line or from a mammalian tissue, or may be mesenchymal cells or pluripotent stem cells such as induced pluripotent stem (iPS) cells. For example, in cases where the dystrophin gene is to be targeted, skeletal muscle cells, mesenchymal cells, or iPS cells derived from a DMD patient may be established, and then guide RNA and CRISPR-Cas, or a guide RNA pair and Cas nickase, for induction of exon skipping of the present invention may be simultaneously introduced into the cells, to induce exon skipping of the dystrophin gene, thereby enabling recovery of the dystrophin protein. By transplanting such repaired cells or an induced product therefrom to a patient, atrophic muscle cells can be complemented.

Further, in another mode, guide RNA and CRISPR-Cas, or a guide RNA pair and Cas nickase, for induction of exon skipping of the present invention are simultaneously introduced into a muscular tissue of a DMD patient, to induce exon skipping of the dystrophin gene, thereby enabling recovery of the dystrophin protein in the body of the patient.

<Method of Evaluation of Exon Skipping>

The present invention also provides a method of evaluating exon skipping using CRISPR-Cas and guide RNA and the like, comprising use of a marker gene containing a sequence which is inserted in a coding region and which contains a first intron, an exon to be analyzed, and a second intron, wherein the marker gene is designed such that the marker gene functions when the exon to be analyzed is skipped (by the action of the guide RNA and the CRISPR-Cas arranged near the exon to be analyzed).

Exon skipping can be induced also in antisense nucleic acid or the like, and the subject to be evaluated is not limited to genome editing.

Examples of the marker gene include, but are not limited to, genes of enzymes such as luciferase or LacZ; genes encoding a fluorescent protein such as GFP, Ds-Red, or mCherry; and drug resistance genes such as the Puro resistance gene, Neo resistance gene, Hyg resistance gene, Bls gene, hisD gene, Gpt gene, and Ble gene. In cases where cDNA of the marker gene contains a sequence which is the same as or similar to the splicing donor or acceptor sequence, the corresponding site is preferably altered such that splicing in the marker does not occur, for the purpose of specifically evaluating splicing in the inserted sequence.

The position to which the sequence containing the first intron (containing a donor site and an acceptor site), the exon to be analyzed, and the second intron (containing a donor site and an acceptor site) is inserted is a position where the marker gene is prevented from functioning (where the activity of the marker protein or the phenotype based on the marker gene disappears) when the exon is inserted. The fact that the exon insertion prevents the marker gene from functioning may be confirmed in advance. As the sequence of the insertion site, the "@" portion in the sequence of CAG@G or AAG@G is more preferably selected since, by this, the splice donor sequence of the first intron and the splice acceptor sequence of the second intron become the consensus (most frequent) sequences of the human splice acceptor (MAG|GURAG) and the human splice acceptor sequence (NCAG|G).

In the method of the present invention, in cases where the splicing normally occurs, the marker gene is expressed as a fusion protein (which lost the original activity) containing the exon inserted therein, or the marker gene does not function since the insertion of the exon prevents normal expression.

On the other hand, in cases where the exon is skipped by genome editing, the marker gene is expressed as a normal type, so that the activity of the marker protein or the phenotype based on the marker gene is found.

Thus, whether or not skipping of the exon occurred can be analyzed based on the presence or absence of the function of the marker gene. This enables simple evaluation of exon skipping, and is also useful for screening for compounds that promote exon skipping.

Whether or not exon skipping has occurred in a cell into which the altered marker gene is introduced can be investigated by introducing guide RNA corresponding to the inserted sequence together with CRISPR-Cas, and analyzing the phenotype of the cell corresponding to the marker gene. Incorporation of the altered marker gene into the chromosome is preferably carried out using a transposon vector or a virus vector. Examples of the transposon vector include piggyBac vectors, piggyBat vectors, Sleeping Beauty vectors, TolII vectors, and LINE vectors. Examples of the virus vector include retrovirus vectors, lentivirus vectors, adenovirus vectors, Sendai virus vectors, and adeno-associated virus vectors.

Examples of the type of the exon include, but are not limited to, exon 45 of the dystrophin gene as described above.

EXAMPLES

The present invention is described below concretely by way of Examples. However, the present invention is not limited to the following modes.
<Methods>
<Unique k-Mer Database> in Relation to FIG. 2

Using a Perl script, base sequences of 10 to 16-mer (k-mer) with all combinations were generated. Using the Bowtie program (Langmead et al., 2009), the k-mer sequences generated were mapped on human genome hg19 without accepting a mismatch. Subsequently, k-mer sequences mapped only once on human genome hg19 were extracted, and a unique k-mer database was constructed (Li H L et al., Stem Cell Reports, 2015). Using the ngs.plot.r program (Shen L et al., BMC Genomics, 2014), which runs with the R language, the distribution of unique k-mers in 200 bp before and after all human exons were investigated and plotted.
<Construction of SpCas9 cDNA Expression Vectors>

DNA synthesis (GenScript) was carried out to prepare the pUC57-SphcCas9 vector, which has a Cas9 cDNA derived from *Streptococcus pyogenes* optimized for the human codon frequencies inserted therein, the Cas9 cDNA having an SV40 large T antigen-derived nuclear localization signal peptide (PKKKRKV) (SEQ ID NO:217) at the C-terminus. This was cleaved with SalI-XbaI restriction enzymes, and then ligated to the SalI-XbaI site of pENTR2B (A10463, Thermo Fisher) to construct the pENTR-SphcCas9 vector. Subsequently, the SphcCas9 cDNA portion of the pENTR-SphcCas9 vector was inserted into the pHL-EF1α-GW-iC-A vector, the pHL-EF1α-GW-iP-A vector, and the pHL-EF1α-GW-A vector by the Gateway LR clonase reaction, to construct the pHL-EF1α-SphcCas9-iC-A vector (SpCas9-IRES-mCheery-polyA), the pHL-EF1α-SphcCas9-iP-A vector (SpCas9-IRES-PuroR-polyA) (Addgene, 60599), and the pHL-EF1α-SphcCas9-A vector (SpCas9-polyA). The EF1α promoter is more suitable than virus-derived promoters (the CMV promoter and the like) since a higher expression level can be obtained in pluripotent stem cells.

Further, for preparation of the D10A mutant of SpCas9 (nickase), the DNA sequence SphcCas9-D10A (NcoI-SbfI), in which the GaC codon (Asp, D) was converted to the GcC codon (Ala, A), was synthesized by gBlock (IDT).

The SphcCas9-D10A(NcoI-SbfI) sequence was cleaved with the NcoI-SbfI restriction enzymes, and then inserted into the NcoI-SbfI site of the pENTR-SphcCas9 vector using the In-Fusion reaction, to construct the pENTR-SphcCas9-D10A vector. Subsequently, the SphcCas9-D10A cDNA portion of the pENTR-SphcCas9-D10A was inserted into the pHL-EF1α-GW-iC-A vector and the pHL-EF1α-GW-iP-A vector by the Gateway LR clonase reaction, to construct the pHL-EF1α-SphcCas9-D10A4C-A vector (SpCas9-IRES-mCheery-polyA) and the pHL-EF1α-SphcCas9-D10A4P-A vector (SpCas9-IRES-PuroR-polyA).

SphcCas9-D10A(NcoI-SbfI)

(SEQ ID NO: 14)

5'-ATTCAGTCGA<u>CCATGG</u>ATAAGAAATACAGCATTGGACTG<u>Gc</u>CATTGG

GACAAACTCCGTGGGATGGGCCGTGATTACAGACGAATACAAAGTGCCTT

CAAAGAAGTTCAAGGTGCTGGGCAACACCGATAGACACAGCATCAAGAAA

AATCTGATTGGAGCCCTGCTGTTCGACTCCGGCGAGACAGCTGAAGCAAC

TCGGCTGAAAAGAACTGCTCGGAGAAGGTATACCCGCCGAAAGAATAGGA

TCTGCTA<u>CCTGCAGG</u>AGATTTTCAGCAA-3'

<Construction of SpCas9 gRNA Expression Vectors>

For cloning of gRNA of SpCas9 into an expression vector, 10 pmol each of the following arbitrary Sp-sgRNA-XXX-fwd primer (one of SEQ ID NOs:17 to 42) and the Sp-sgRNA-Universal-rev primer were mixed together, and thermal cycling reaction was performed using KOD Plus Neo DNA polymerase (Toyobo) (heat denaturation at 98° C.: 2 min followed by {94° C.: 10 sec, 55° C.: 10 sec, 68° C.: 10 sec}×35 cycles, further followed by incubation at 4° C.). The resulting PCR product was subjected to electrophoresis in 2% agarose gel, and a DNA band with a size of about 135 bp was excised and purified. The purified PCR product was inserted, using the In-Fusion reaction (Takara-Clontech), into the pHL-H1-ccdB-mEF1a-RiH vector (Addgene 60601) cleaved with BamHI-EcoRI, to construct a pHL-H1-[SpCas9-gRNA]-mEF1a-RiH vector which expresses an arbitrary gRNA.

PCR Product Sequence (135 bp)

(SEQ ID NO: 15)

GAGACCACTTGGATCCRNNNNNNNNNNNNNNNNNNNNGTTTTAGAGCTA

GAAATAGCAAGTTAAAATAAGGCTAGTCCGTTATCAACTTGAAAAAGT

GGCACCGAGTCGGTGCTTTTTTTGAATTCAAACCCGGGC

Sp-sgRNA-XXX-fwd (SEQ ID NO: 16)

GAGACCACTTGGATCCRNNNNNNNNNNNNNNNNNNNNGTTTTAGAGCTA

GAAATAGCA

Sp-sgRNA-DMD1-fwd (SEQ ID NO: 17)

GAGACCACTTGGATCCGggtatcttacaggaactccGTTTTAGAGCTA

GAAATAGCA

Sp-sgRNA-DMD2-fwd
(SEQ ID NO: 18)
GAGACCACTTGGATCCGtcttacaggaactccaggaGTTTTAGAGCTA
GAAATAGCA Sp-sgRNA-DMD3-fwd
(SEQ ID NO: 19)
GAGACCACTTGGATCCGaggaactccaggatggcatGTTTTAGAGCTA
GAAATAGCA Sp-sgRNA-DMD4-fwd
(SEQ ID NO: 20)
GAGACCACTTGGATCCGCCAGGATGGCATTGGGCAGGTTTTAGAGCTA
GAAATAGCA Sp-sgRNA-DMD5-fwd
(SEQ ID NO: 21)
GAGACCACTTGGATCCGTTCCTGTAAGATACCAAAAGTTTTAGAGCTA
GAAATAGCA Sp-sgRNA-DMD6-fwd
(SEQ ID NO: 22)
GAGACCACTTGGATCCGcaTTTTTGTTTTGCCTTTTGTTTTAGAGCTA
GAAATAGCA Sp-sgRNA-DMD7-fwd
(SEQ ID NO: 23)
GAGACCACTTGGATCCGTGCCTTTTTGGTATCTTACGTTTTAGAGCTA
GAAATAGCA Sp-sgRNA-DMD8-fwd
(SEQ ID NO: 24)
GAGACCACTTGGATCCAGGAACTCCAGGATGGCATTGTTTTAGAGCTA
GAAATAGCA Sp-sgRNA-DMD9-fwd
(SEQ ID NO: 25)
GAGACCACTTGGATCCGCCGCTGCCCAATGCCATCCGTTTTAGAGCTA
GAAATAGCA Sp-sgRNA-DMD10-fwd
(SEQ ID NO: 26)
GAGACCACTTGGATCCGTCAGAACATTGAATGCAACGTTTTAGAGCTA
GAAATAGCA Sp-sgRNA-DMD11-fwd
(SEQ ID NO: 27)
GAGACCACTTGGATCCGCAGAACATTGAATGCAACTGTTTTAGAGCTA
GAAATAGCA Sp-sgRNA-DMD12-fwd
(SEQ ID NO: 28)
GAGACCACTTGGATCCGAGAACATTGAATGCAACTGGTTTTAGAGCTA
GAAATAGCA Sp-sgRNA-DMD13-fwd
(SEQ ID NO: 29)
GAGACCACTTGGATCCAATACTGGCATCTGTTTTGGTTTTAGAGCTA
GAAATAGCA Sp-sgRNA-DMD14-fwd
(SEQ ID NO: 30)
GAGACCACTTGGATCCAACAGATGCCAGTATTCTACGTTTTAGAGCTA
GAAATAGCA Sp-sgRNA-DMD15-fwd
(SEQ ID NO: 31)
GAGACCACTTGGATCCGAATTTTTCCTGTAGAATACGTTTTAGAGCTA
GAAATAGCA Sp-sgRNA-DMD16-fwd
(SEQ ID NO: 32)
GAGACCACTTGGATCCGAGTATTCTACAGGAAAAATGTTTTAGAGCTA
GAAATAGCA Sp-sgRNA-DMD17-fwd
(SEQ ID NO: 33)
GAGACCACTTGGATCCAGTATTCTACAGGAAAAATTGTTTTAGAGCTA
GAAATAGCA Sp-sgRNA-DMD18-fwd
(SEQ ID NO: 34)
GAGACCACTTGGATCCAATTGGGAAGCCTGAATCTGGTTTTAGAGCTA
GAAATAGCA Sp-sgRNA-DMD19-fwd
(SEQ ID NO: 35)
GAGACCACTTGGATCCGGGGAAGCCTGAATCTGCGGGTTTTAGAGCTA
GAAATAGCA Sp-sgRNA-DMD20-fwd
(SEQ ID NO: 36)
GAGACCACTTGGATCCAAGCCTGAATCTGCGGTGGCGTTTTAGAGCTA
GAAATAGCA Sp-sgRNA-DMD21-fwd
(SEQ ID NO: 37)
GAGACCACTTGGATCCGCTGAATCTGCGGTGGCAGGGTTTTAGAGCTA
GAAATAGCA Sp-sgRNA-DMD22-fwd
(SEQ ID NO: 38)
GAGACCACTTGGATCCGCTCCTGCCACCGCAGATTCGTTTTAGAGCTA
GAAATAGCA Sp-sgRNA-DMD23-fwd
(SEQ ID NO: 39)
GAGACCACTTGGATCCAGCTGTCAGACAGAAAAAAGGTTTTAGAGCTA
GAAATAGCA Sp-sgRNA-DMD24-fwd
(SEQ ID NO: 40)
GAGACCACTTGGATCCGTCAGACAGAAAAAAGAGGTGTTTTAGAGCTA
GAAATAGCA Sp-sgRNA-DMD25-fwd
(SEQ ID NO: 41)
GAGACCACTTGGATCCGCAGACAGAAAAAAGAGGTAGTTTTAGAGCTA
GAAATAGCA Sp-sgRNA-DMD26-fwd
(SEQ ID NO: 42)
GAGACCACTTGGATCCGGTAGGGCGACAGATCTAATGTTTTAGAGCTA
GAAATAGCA Sp-sgRNA-Universal-rev
(SEQ ID NO: 43)
GCCCGGGTTTGAATTCAAAAAAAGCACCGACTCGGTGCCACTTTTTCA
AGTTGATAACGGACTAGCCTTATTTTAACTTGCTATTTCTAGCTCTAA <Construction of SaCas9 cDNA Expression Vectors> in Relation to FIGS. 13a to 13d DNA synthesis (GenScript) was carried out to prepare the pUC-Kan-SahcCas9 vector, which has a Cas9 cDNA derived from *Staphylococcus aureus* optimized for the human codon frequencies inserted between the Gateway attL1 site and attL2 site, the Cas9 cDNA having an SV40 large T NLS at the N-terminus, and a nucleoplasmin NLS and a 3×HA tag at the C-terminus. Subsequently, the SaCas9 cDNA portion of the pUC-Kan-SahcCas9 vector was inserted into the pHL-EF1α-GW-A and pHL-EF1α-GW-iP-A vectors by the Gateway LR clonase reaction, to construct the HL-EF1α-SaCas9-A and HL-EF1α-SaCas9-iC-A vectors, respectively.

<Construction of SaCas9 gRNA Expression Vectors>

For cloning of gRNAs of SaCas9 into an expression vector, 10 pmol each of the following arbitrary sgRNA-DMD-SA-X-fwd primer (one of SEQ ID NOs:44 to 45) and the SA1-gRNA-Universal-Rev primer were mixed together, and thermal cycling reaction was performed using KOD Plus Neo DNA polymerase (Toyobo) (heat denaturation at 98° C.: 2 min followed by {94° C.: 10 sec, 55° C.: 10 sec, 68° C.: 10 sec}×35 cycles, further followed by incubation at 4° C.). The resulting PCR product was subjected to electrophoresis in 2% agarose gel, and a DNA band with a size of about 135 bp was excised and purified. The purified PCR product was inserted, using the In-Fusion reaction (Takara-Clontech), into the pHL-H1-ccdB-mEF1a-RiH vector (Addgene 60601) cleaved with BamHI-EcoRI, to construct a pHL-H1-[SaCas9-gRNA]-mEF1a-RiH vector which expresses the arbitrary gRNA.

sgRNA-DMD-SA-5
(SEQ ID NO: 44)
5'-GAGACCACTTGGATCCATTACAGGAACTCCAGGATGGCAGTTTTA

GTACTCTGGAAACAGAAT-3' sgRNA-DMD-SA-8
(SEQ ID NO: 45)
5'-GAGACCACTTGGATCCATTGCCGCTGCCCAATGCCATCCGTTTTAG

TACTCTGGAAACAGAAT-3'

SA1-gRNA-Universal-Rev
(SEQ ID NO: 46)
5'-GCCCGGGTTTGAATTCAAAAAAATCTCGCCAACAAGTTGACGAGAT

AAACACGGCATTTTGCCTTGTTTTAGTAGATTCTGTTTCCAGAGTACT

AA-3'

<Construction of AsCpf1 cDNA Expression Vectors> in Relation to FIGS. 13a to 13d DNA synthesis (GenScript) was carried out to prepare the pUC57-hcAsCpf1 vector, which has a Cpf1 cDNA derived from *Acidaminococcus* sp. BV3L6 optimized for the human codon frequencies is inserted between the Gateway attL1 site and attL2 site, the Cpf1 cDNA having a nucleoplasmin NLS (KRPAATKKAGQAKKKK) (SEQ ID NO:218) and a 3×HA tag (YPYDVPDYA YPYDVPDYA YPYDVPDYA) (SEQ ID NO:219) sequence at the C-terminus. Subsequently, the hcAsCpf1 cDNA portion of the pENTR-hcAsCpf1 vector was inserted into the pHL-EF1α-GW-A and pHL-EF1α-GW-iP-A vectors by the Gateway LR clonase reaction, to construct the HL-EF1α-hcAsCpf1-A and HL-EF1α-hcAsCpf1-iC-A vectors, respectively.

<Construction of AsCpf1 gRNA Expression Vectors>

For cloning of gRNAs of AsCpf1 into an expression vector, 10 pmol each of the following arbitrary AsCpf1-gRNA-XXX-rev primer (one of SEQ ID NOs:50 to 53) and the AsCpf1-gRNA-Universal-GGG-fwd primer (or the AsCpf1-gRNA-Universal-G-fwd primer) were mixed together, and thermal cycling reaction was performed using KOD Plus Neo DNA polymerase (Toyobo) (heat denaturation at 98° C.: 2 min followed by {94° C.: 10 sec, 55° C.: 10 sec, 68° C.: 10 sec}×35 cycles, further followed by incubation at 4° C.). The resulting PCR product was subjected to electrophoresis in 2% agarose gel, and a DNA band with a size of about 80 bp was excised and purified. The purified PCR product was inserted, using the In-Fusion reaction (Takara-Clontech), into the pHL-H1-ccdB-mEF1a-RiH vector cleaved with BamHI-EcoRI, to construct a pHL-H1-[AsCpf1-gRNA]-mEF1a-RiH vector which expresses the AsCpf1 gRNA.

AsCpf1-gRNA-Universal-GGG-fwd (GGG at TSS)
(SEQ ID NO: 47)
5'-GAGACCACTTGGATCCGGGTAATTTCTACTCTTGTAGAT-3'

AsCpf1-gRNA-Universal-G-fwd (G at TSS)
(SEQ ID NO: 48)
5'-GAGACCACTTGGATCCGTAATTTCTACTCTTGTAGAT-3'

AsCpf1-gRNA-XXX-rev
(SEQ ID NO: 49)
5'-GCCCGGGTTTGAATTCAAAAAAANNNNNNNNNNNNNNNNNNN

NATCTACAAGAGTAGAAATTA-3'

AsCpf1-gRNA-DMD1-rev
(SEQ ID NO: 50)
5'-GCCCGGGTTTGAATTCAAAAAAAGGAGTTCCTGTAAGATACC

AATCTACAAGAGTAGAAATTA-3'

AsCpf1-gRNA-DMD2-rev
(SEQ ID NO: 51)
5'-GCCCGGGTTTGAATTCAAAAAAATGGAGTTCCTGTAAGATAC

CATCTACAAGAGTAGAAATTA-3'

AsCpf1-gRNA-DMD3-rev
(SEQ ID NO: 52)
5'-GCCCGGGTTTGAATTCAAAAAAACTGGAGTTCCTGTAAGATA

CATCTACAAGAGTAGAAATTA-3'

AsCpf1-gRNA-DMD4-rev
(SEQ ID NO: 53)
5'-GCCCGGGTTTGAATTCAAAAAAAGGATGGCATTGGGCAGCG

GATCTACAAGAGTAGAAATTA-3'

Figure 10:
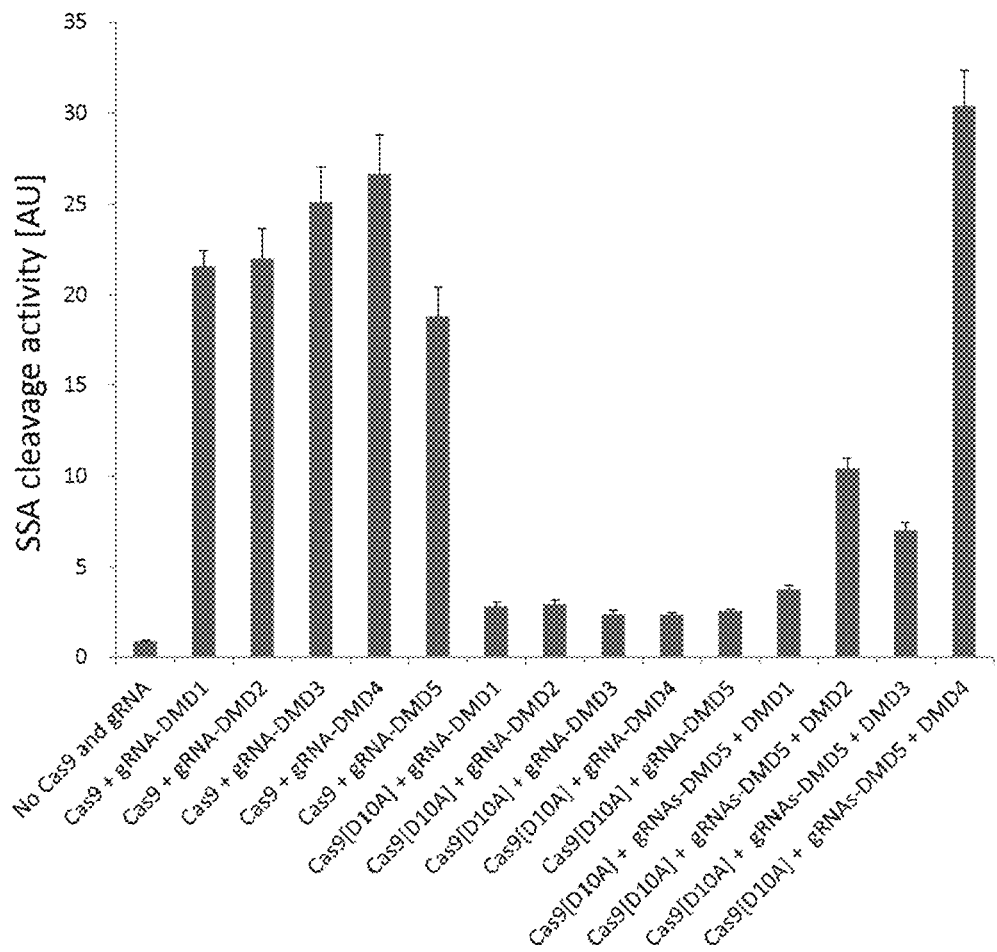
FIG. 10 shows the target DNA cleavage activities obtained using CRISPR-SpCas9 and CRISPR-SpCas9 (D10A) in human 293T cells as measured by an SSA assay. In the cases of CRISPR-SpCas9, the cleavage activity was found with any of the guide RNAs 1 to 5. On the other hand, in the cases where the nickase-modified SpCas9(D10A) was used, no cleavage activity, as expected, was found when only a single guide RNA was used. A high DNA cleavage activity could be found in the case where the guide RNA 5 for the sense strand and the guide RNA 4 for the antisense strand were used in combination.

<Construction of SSA Vector> in Relation to FIG. 10

The SSA-DMD-all-ss oligo DNA and the SSA-DMD-all-as oligo DNA, which have the target sequences of Sp-gRNA-DMD1 to 5, were annealed with each other, and then ligated into the BsaI site present in firefly Luc2 cDNA of the pGL4-SSA vector (Addgene 42962, Ochiai et al., Genes Cells, 2010), to construct the pGL4-SSA-DMD-all vector. In the pGL4-SSA-DMD-all vector, the firefly Luc2 cDNA is divided, and does not show Luc activity. However, when cleavage of the target DNA portion in the pGL4-SSA vector is induced by guide RNA, the DNA cleavage is repaired by the SSA (single strand annealing) pathway, resulting recovery of the firefly Luc2 cDNA.

```
SSA-DMD-all-ss
                                       (SEQ ID NO: 54)
5'-gtcgTGCCTTTTTGGTATCTTACAG

GAACTCCAGGATGGCATTGGGCAGCG

GCAAACTGTTGTCAGAACATggt-3'

SSA-DMD-all-as
                                       (SEQ ID NO: 55)
5'-cggtaccATGTTCTGACAACAGTT

TGCCGCTGCCCAATGCCATCCTGGAGT

TCCTGTAAGATACCAAAAAGGCA-3'
```

Figure 13B:
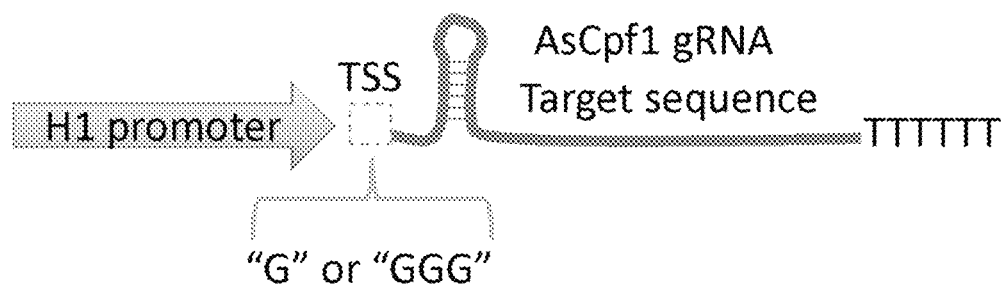
FIG. 13b shows a schematic view of an AsCpf1 gRNA expression cassette. It is known that G (or A) is desirable as the transcription start site (TSS) of the H1 promoter. It was thus expected that, by increasing the number of G's from one base to three bases, the expression level of the gRNA may be increased, resulting in an increased target DNA cleavage efficiency.
Figure 13C:
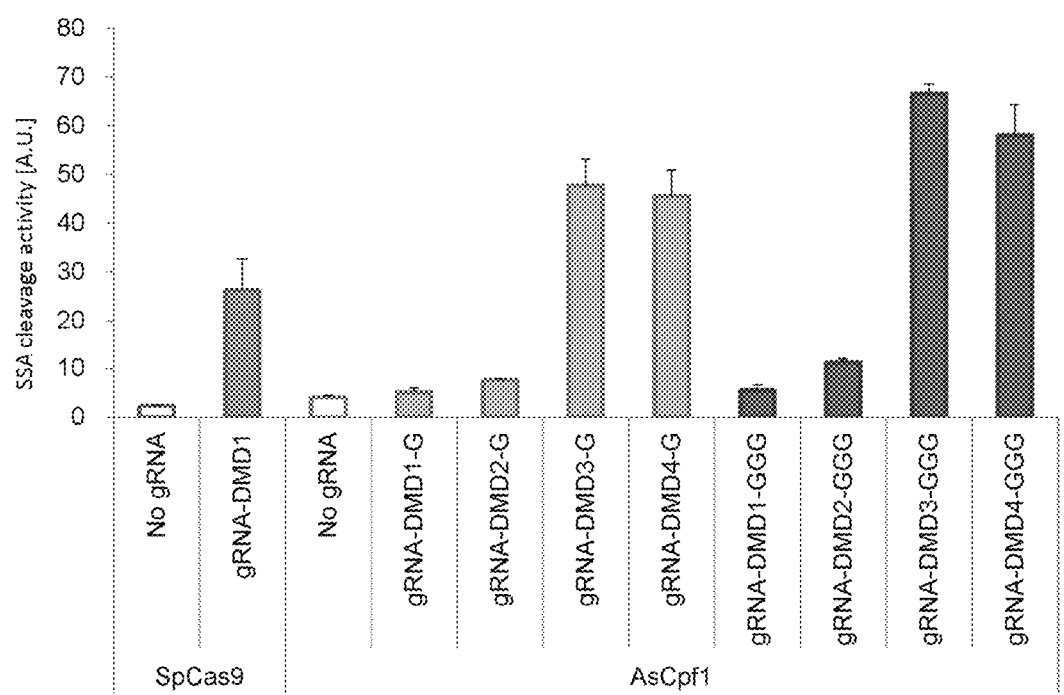
FIG. 13c shows the results obtained by introducing AsCpf1 and gRNA into 293T cells, and then measuring the target DNA cleavage activity by an SSA assay. First, by increasing the number of G's at the transcription start site (TSS) from one base to three bases, an increased cleavage activity could be found. Further, AsCpf1-gRNA-DMD1 and AsCpf1-gRNA-DMD2, which have TTTT as the PAM sequence, had very low cleavage activities, but AsCpf1-gRNA-DMD3 and AsCpf1-gRNA-DMD4, which have TTTG (TTTV) as the PAM, showed cleavage activities equivalent to or higher than that of SpCas9-gRNA-DMD1.
Figure 13D:
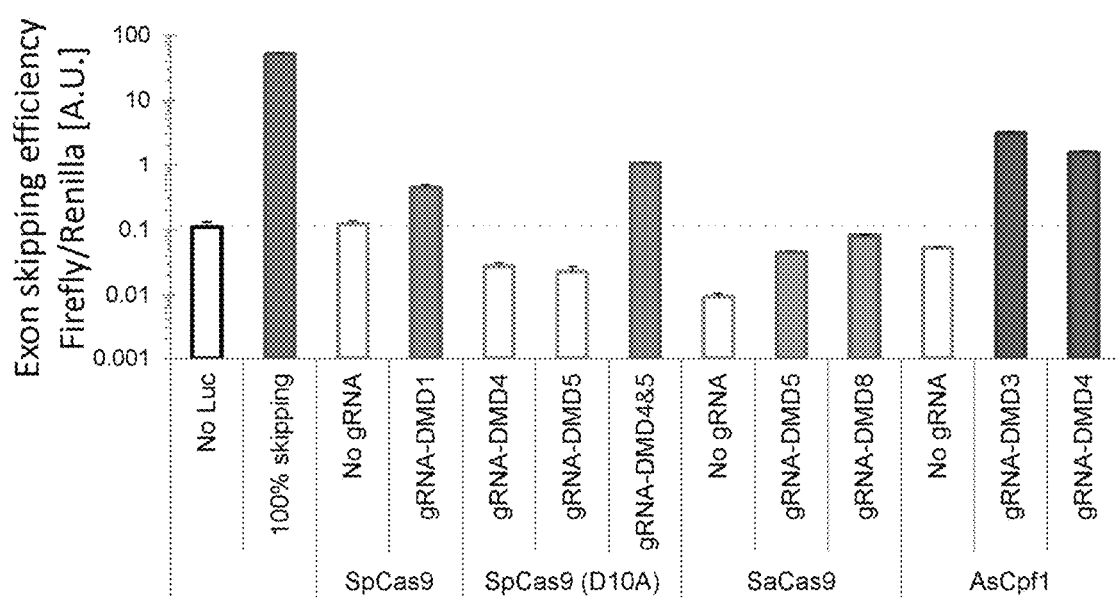
FIG. 13d shows the exon skipping efficiencies measured using Luc2 (G967A)+hEx45 (0.7 kb) as an exon skipping reporter in 293T cells, which measurement was carried out for cases where the double nicking method, SaCas9/gRNA, or AsCpf1/gRNA was used. As a result, in the case where sgRNA-DMD4 and sgRNA-DMD5 were used as a pair in the SpCas9(D10A) double nicking method, a higher exon skipping activity was induced compared to SpCas9/sgRNA-DMD1. Further, also in the cases where sgRNA-DMD3 or sgRNA-DMD4 of AsCpf1 was used, high exon skipping efficiencies could be induced.

<Target DNA Cleavage Activity by SSA Assay> FIG. 10, FIG. 13c

A mixture of 100 ng of the pGL4-SSA-DMD-All vector, 20 ng of the phRL-TK vector, which expresses Renilla Luc, 200 ng of the pHL-EF1a vector, which expresses CRISPR-Cas, and 200 ng of the pHL-H1-sgRNA-mEF1a-RiH vector, which expresses sgRNA, was prepared, and then diluted with 25 μl of Opti-MEM. With 25 μl of Opti-MEM, 0.7 μl of Lipofectamine 2000 was diluted, and the resulting dilution was incubated at room temperature for 3 to 5 minutes, followed by mixing the dilution with the above DNA solution, and then incubating the resulting mixture at room temperature for additional 20 minutes. The cell number of 293T cells suspended by trypsin-EDTA treatment was counted, and then the cells were diluted to 60,000 cells/100 μl with a medium, followed by plating the cells on a 96-well plate containing the above DNA-Lipofectamine complex at 100 μl/well. After culturing the cells for 48 hours with 5% $CO_2$ at 37° C., the 96-well plate was allowed to cool to room temperature, and then Dual-Glo Reagent was added thereto, followed by incubation at room temperature for 30 minutes to lyse the cells to cause the luciferase reaction. To a white 96-well plate, 100 μl of the supernatant was transferred, and the luminescence intensities of Firefly and Renilla were measured using Centro LB960 (Berthold Technologies). Since firefly Luc emits light only when DNA cleavage is induced by CRISPR, the luminescence value of firefly was normalized against the luminescence value of Renilla to measure the DNA cleavage efficiency.

<Cell Culture>

293T cells were cultured in DMEM medium supplemented with 5 to 10% FBS.

DMD-iPS cells (clone ID: CiRA00111) were cultured, on SNL feeder cells whose growth was inhibited by mitomycin C treatment, using Knockout SR medium {prepared by adding 50 mL of Knockout SR (Thermo Fisher, 10828028), 2.5 mL of L-glutamine (Thermo Fisher, 25030081), 2.5 mL of non-essential amino acid mixture (Thermo Fisher, 11140050), 0.5 mL of 2-mercaptoethanol (Thermo Fisher, 21985023), 1.25 mL of penicillin-streptomycin (Thermo Fisher, 15140122), and 8 ng/ml human basic FGF (Wako, 6404541) to 200 mL of DMEM/F12 medium (Thermo Fisher, 10565018)}. Alternatively, using StemFit AK03N (Ajinomoto) medium, the cells may be cultured on iMatrix-511 (Nippi, 892014) without the use of feeder cells.

Figure 11:
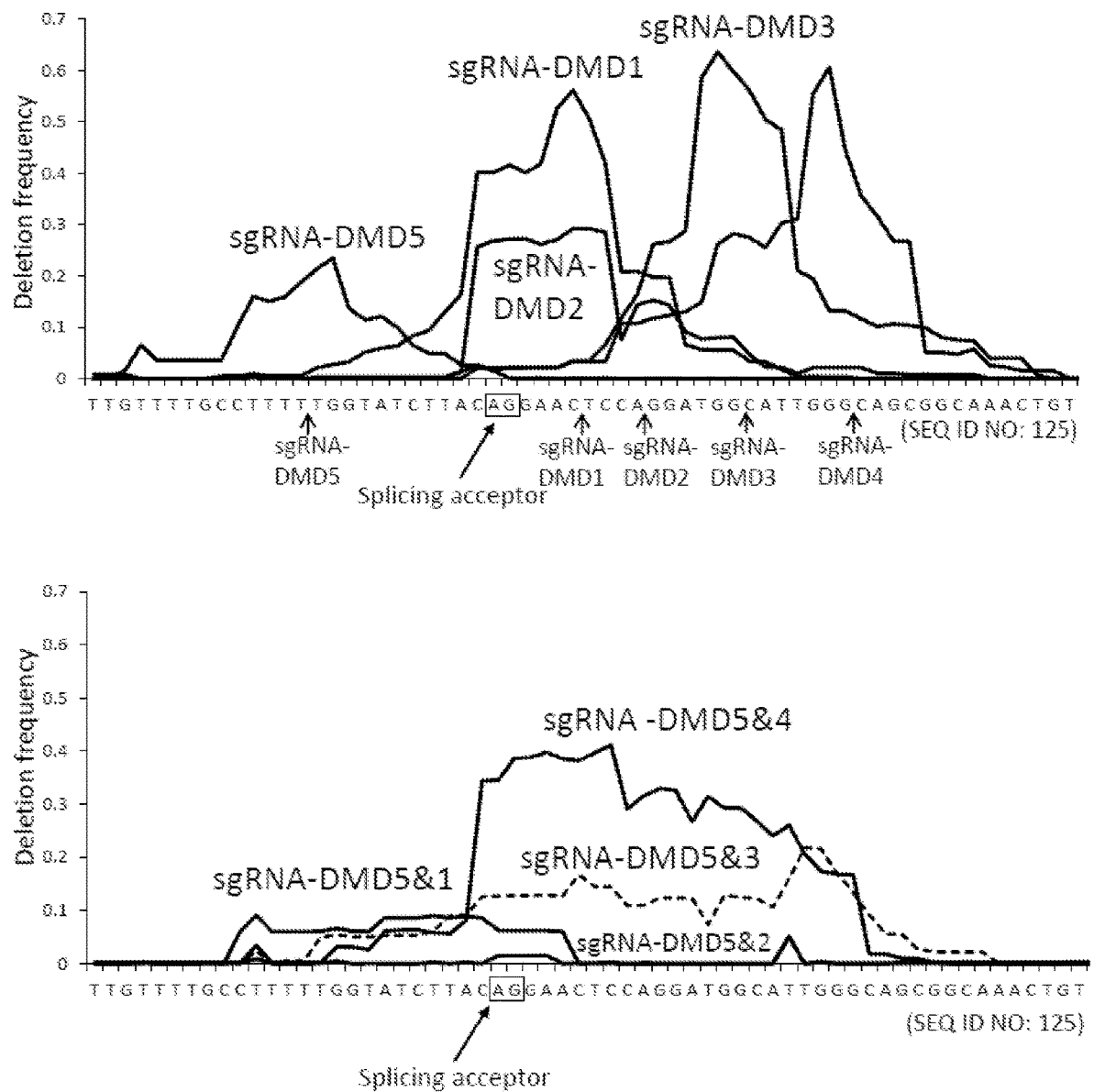
FIG. 11 shows cleavage patterns as analyzed by cleaved-sequence analysis. Plasmid DNAs expressing CRISPR-Cas9 and its guide RNA were introduced into DMD-iPS cells by electroporation, and genomic DNA was extracted. Thereafter, the genomic DNA cleavage pattern was analyzed using a MiSeq sequencer. The results are shown as line charts drawn by stacking positions having a base deletion.

<Analysis of Genome DNA Cleavage Pattern in DMD-iPS Cells> FIG. 11

For iPS cells established from a DMD patient who lacks exon 44, 10 μM Y-27632 (Sigma) was added to the medium not less than one hour before transfection. Immediately before electroporation, the iPS cells were detached with CTK solution, and then dispersed using 0.25% trypsin-EDTA, followed by counting the cells for providing $1 \times 10^6$ cells for each condition. To these cells, electroporation of 5 μg of the pHL-EF1α-SphcCas9-iP-A vector (Addgene, 60599) and 5 μg of the pHL-H1-[Sp-gRNA]-mEF1α-RiH vector was carried out using a NEPA21 electroporator (Nepa Gene) with a poration pulse voltage of 125 V, a pulse width of 5 milliseconds, and a number of pulses of 2. In the cases where double-nicking was carried out, electroporation was carried out with 5 μg of the pHL-EF1α-SphcCas9-D10A4P-A vector and a total of 10 that is, 5 μg each, of two kinds of pHL-H1-[Sp-gRNA]-mEF1α-RiH vectors. The iPS cells subjected to the electroporation were cultured for not less than several days, and genome DNA was extracted therefrom, followed by performing primary PCR amplification using the DMD-MiSeq-Rd1-fwd-X and DMD-MiSeq-Rd2-rev-X primers, and then performing secondary PCR amplification using the Multiplex P5 fwd primer and the Multiplex P7 rev primer. The resulting PCR product was excised from the gel, and then purified, followed by quantification using a Qubit 2.0 Fluorometer (Thermo Fisher) and a KAPA Library Quantification Kit for Illumina (KAPA Biosystems). The samples were mixed to the same amount, and the DNA concentration was adjusted to 2 nM, followed by performing alkali denaturation of the DNA by treatment with 0.2 N NaOH for 5 minutes. Each denatured DNA sample was diluted to 12 pM, and then 4 pM PhiX spike-in DNA was added thereto, followed by performing MiSeq sequencing reaction using a MiSeq Reagent Kit v2 for 2×150 bp (Illumina). From the FASTQ sequence file generated as a result of the sequencing, low-quality reads were removed by using the fastq_quality_filter program in the FASTX-Toolkit. After removing the PhiX sequence used as the spike-in, the fastx_barcode_splitter program was used to divide the samples according to the barcode sequences. The sequences of the samples were mapped using the BWA program, and the insertion/deletion patterns of the sequences were extracted from the MD tag information in the CIGAR code.

```
DMD-MiSeq-Rd1-fwd-X (N represents the barcode
sequence corresponding to each sample.
See below.)
                                       (SEQ ID NO: 56)
5'-CTCTTTCCCTACACGACGCTCTTCCGATCTNNNNNAATAAAAA

GACATGGGCTTCA-3'

DMD-MiSeq-Rd2-rev-X (N represents the barcode
sequence corresponding to each sample.
See below.)
                                       (SEQ ID NO: 57)
5'-CTGGAGTTCAGACGTGTGCTCTTCCGATCTNNNNCTGGCATCT

GTTTTTGAGGA-3'

Multiplex P5 fwd
                                       (SEQ ID NO: 58)
5'-AATGATACGGCGACCACCGAGATCTACACTCTTTCCCTACACG

ACGCTC-3'

Multiplex P7 rev
                                       (SEQ ID NO: 59)
5'-CAAGCAGAAGACGGCATACGAGATGTGACTGGAGTTCAGACGT

GTGCTC-3'
```

Specific sequences containing the barcode for the X

DMD-MiSeq-Rd1-fwd1-AGTC
(SEQ ID NO: 60)
5'-CTCTTTCCCTACACGACGCTCTTC
CGATCTagtcAATAAAAAGACATGGG
GCTTCA-3'

DMD-MiSeq-Rd1-fwd2-GTCA
(SEQ ID NO: 61)
5'-CTCTTTCCCTACACGACGCTCTTC
CGATCTgtcaAATAAAAAGACATGGG
GCTTCA-3'

DMD-MiSeq-Rd1-fwd3-TCAG
(SEQ ID NO: 62)
5'-CTCTTTCCCTACACGACGCTCTTC
CGATCTtcagAATAAAAAGACATGGG
GCTTCA-3'

DMD-MiSeq-Rd1-fwd4-CAGT
(SEQ ID NO: 63)
5'-CTCTTTCCCTACACGACGCTCTTC
CGATCTcagtAATAAAAAGACATGGG
GCTTCA-3'

DMD-MiSeq-Rd1-fwd5-ATGC
(SEQ ID NO: 64)
5'-CTCTTTCCCTACACGACGCTCTTC
CGATCTatgcAATAAAAAGACATGGG
GCTTCA-3'

DMD-MiSeq-Rd1-fwd6-TGCA
(SEQ ID NO: 65)
5'-CTCTTTCCCTACACGACGCTCTTC
CGATCTtgcaAATAAAAAGACATGGG
GCTTCA-3'

DMD-MiSeq-Rd1-fwd7-GCAT
(SEQ ID NO: 66)
5'-CTCTTTCCCTACACGACGCTCTTC
CGATCTgcatAATAAAAAGACATGGG
GCTTCA-3'

DMD-MiSeq-Rd1-fwd8-CATG
(SEQ ID NO: 67)
5'-CTCTTTCCCTACACGACGCTCTTC
CGATCTcatgAATAAAAAGACATGGG
GCTTCA-3'

DMD-MiSeq-Rd1-fwd9-AACG
(SEQ ID NO: 68)
5'-CTCTTTCCCTACACGACGCTCTTC
CGATCTaacgAATAAAAAGACATGGG
GCTTCA-3'

DMD-MiSeq-Rd1-fwd10-ACGA
(SEQ ID NO: 69)
5'-CTCTTTCCCTACACGACGCTCTT
CCGATCTacgaAATAAAAAGACATGGG
GCTTCA-3'

DMD-MiSeq-Rd1-fwd11-CGAA
(SEQ ID NO: 70)
5'-CTCTTTCCCTACACGACGCTCTT
CCGATCTcgaaAATAAAAAGACATGGG
GCTTCA-3'

DMD-MiSeq-Rd1-fwd12-GAAC
(SEQ ID NO: 71)
5'-CTCTTTCCCTACACGACGCTCTT
CCGATCTgaacAATAAAAAGACATGGG
GCTTCA-3'

DMD-MiSeq-Rd1-fwd13-TACC
(SEQ ID NO: 72)
5'-CTCTTTCCCTACACGACGCTCTTC
CGATCTtaccAATAAAAAGACATGGG
GCTTCA-3'

DMD-MiSeq-Rd1-fwd14-ACCT
(SEQ ID NO: 73)
5'-CTCTTTCCCTACACGACGCTCTTC
CGATCTacctAATAAAAAGACATGGG
GCTTCA-3'

DMD-MiSeq-Rd2-rev1-AGTC
(SEQ ID NO: 74)
5'-CTGGAGTTCAGACGTGTGCTCTTC
CGATCTagtcCTGGCATCTGTTTTTGA
GGA-3'

DMD-MiSeq-Rd2-rev2-GTCA
(SEQ ID NO: 75)
5'-CTGGAGTTCAGACGTGTGCTCTTC
CGATCTgtcaCTGGCATCTGTTTTTGA
GGA-3'

DMD-MiSeq-Rd2-rev3-TCAG
(SEQ ID NO: 76)
5'-CTGGAGTTCAGACGTGTGCTCTTC
CGATCTtcagCTGGCATCTGTTTTTGA
GGA-3'

DMD-MiSeq-Rd2-rev4-CAGT
(SEQ ID NO: 77)
5'-CTGGAGTTCAGACGTGTGCTCTTC
CGATCTcagtCTGGCATCTGTTTTTGA
GGA-3'

DMD-MiSeq-Rd2-rev5-ATGC
(SEQ ID NO: 78)
5'-CTGGAGTTCAGACGTGTGCTCTTCC
GATCTatgcCTGGCATCTGTTTTTGA
GGA-3'

DMD-MiSeq-Rd2-rev6-TGCA
(SEQ ID NO: 79)
5'-CTGGAGTTCAGACGTGTGCTCTTCC
GATCTtgcaCTGGCATCTGTTTTTGA
GGA-3'

```
DMD-MiSeq-Rd2-rev7-GCAT
                                          (SEQ ID NO: 80)
5'-CTGGAGTTCAGACGTGTGCTCTTCC GATCTgcatCTGGCATCTGTTTTTGA

GGA-3'

DMD-MiSeq-Rd2-rev8-CATG
                                          (SEQ ID NO: 81)
5'-CTGGAGTTCAGACGTGTGCTCTTCC GATCTcatgCTGGCATCTGTTTTTGA

GGA-3'

DMD-MiSeq-Rd2-rev9-AACG
                                          (SEQ ID NO: 82)
5'-CTGGAGTTCAGACGTGTGCTCTTCC GATCTaacgCTGGCATCTGTTTTTG

AGGA-3'

DMD-MiSeq-Rd2-rev10-ACGA
                                          (SEQ ID NO: 83)
5'-CTGGAGTTCAGACGTGTGCTCTTC CGATCTacgaCTGGCATCTGTTTTTG

AGGA-3'

DMD-MiSeq-Rd2-rev11-CGAA
                                          (SEQ ID NO: 84)
5'-CTGGAGTTCAGACGTGTGCTCTTC CGATCTcgaaCTGGCATCTGTTTTTG

AGGA-3'

DMD-MiSeq-Rd2-rev12-GAAC
                                          (SEQ ID NO: 85)
5'-CTGGAGTTCAGACGTGTGCTCTTC CGATCTgaacCTGGCATCTGTTTTTG

AGGA-3'

DMD-MiSeq-Rd2-rev13-TACC
                                          (SEQ ID NO: 86)
5'-CTGGAGTTCAGACGTGTGCTCTTC CGATCTtaccCTGGCATCTGTTTTTGA

GGA-3'

DMD-MiSeq-Rd2-rev14-ACCT
                                          (SEQ ID NO: 87)
5'-CTGGAGTTCAGACGTGTGCTCTTC CGATCTacctCTGGCATCTGTTTTTGA

GGA-3'
```

<Construction of Exon Skipping Detection Vector Using Luc Reporter>

Luc2 cDNA was amplified by PCR from pGL4-CMV-luc2 (Promega), and then cloned into the pENTR-D-TOPO vector (Thermo Fisher Scientific Inc.), to construct the pENTR-D-TOPO-Luc2 vector. The pENTR-D-TOPO-Luc2 was cleaved with NarI and AgeI, and then the following intron sequence synthesized by gBlock (IDT) and the DMD exon 45 sequence were inserted thereto, to construct the pENTR-D-TOPO-Luc2-DMD-intron-Ex45[+] vector. Subsequently, the gBlock sequence was cleaved at the two SalI sites present in both sides of hEx45, and then the vector side was re-ligated to construct the pENTR-D-TOPO-Luc2-DMD-intron-Ex45[−] vector.

```
NadI-AgeI-DMD-Ex45-gBlock (Sequence of FIG. 6)
                                          (SEQ ID NO: 88)
GCCAGCGGCGGGGCGCCGCTCAGCAAGGAGGTAGGTGAGGCCGTGGCCA

AACGCTTCCACCTACCAGGTAAGTCTTTGATTTGTCGACCGTATCCACG

ATCACTAAGAAACCCAAATACTTTGTTCATGTTTAAATTTTACAACATT

TCATAGACTATTAAACATGGAACATCCTTGTGGGGACAAGAAATCGAAT

TTGCTCTTGAAAAGGTTTCCAACTAATTGATTTGTAGGACATTATAACA

TCCTCTAGCTGACAAGCTTACAAAAATAAAAACTGGAGCTAACCGAGAG

GGTGCTTTTTCCCTGACACATAAAAGGTGTCTTTCTGTCTTGTATCCT

TTGGATATGGGCATGTCAGTTTCATAGGGAAATTTTCACATGGAGCTTT

TGTATTTCTTTCTTTGCCAGTACAACTGCATGTGGTAGCACACTGTTTA

ATCTTTTCTCAAATAAAAAGACATGGGGCTTCATTTTTGTTTTGCCTTT

TTGGTATCTTACAGGAACTCCAGGATGGCATTGGGCAGCGGCAAACTGT

TGTCAGAACATTGAATGCAACTGGGGAAGAAATAATTCAGCAATCCTCA

AAAACAGATGCCAGTATTCTACAGGAAAAATTGGGAAGCCTGAATCTGC

GGTGGCAGGAGGTCTGCAAACAGCTGTCAGACAGAAAAAAGAGGTAGGG

CGACAGATCTAATAGGAATGAAAACATTTTAGCAGACTTTTTAAGCTTT

CTTTAGAAGAATATTTCATGAGAGATTATAAGCAGGGTGAAAGGCGTCG

ACGTTTGCATTAACAAATAGTTTGAGAACTATGTTGGAAAAAAAAATAA

CAATTTTATTCTTCTTTCTCCAGGCATCCGCCAGGGCTACGGCCTGACA

GAAACAACCAGCGCCATTCTGATCACCCCCGAAGGGGACGACAAGCCTG

GCGCAGTAGGCAAGGTGGTGCCCTTCTTCGAGGCTAAGGTGGTGGACTT

GGACACCGGTAAGACACTGG
```

The piggyBac 5'TR (Terminal repeat) and 3'TR sequences derived from *Trichoplusia ni* were synthesized (IDT) as three separate gBlocks sequences (gBlock11 to 13-PV-3'TR-5'TR), and the three fragments were linked to each other by PCR, followed by insertion into the AatII-PvuII site in the pUC 19 vector by the In-Fusion reaction, to construct the pPV-synthesized vector.

```
gBlock11-PV-3'TR-5'TR
                                          (SEQ ID NO: 89)
GAAAAGTGCCACCTGACGTCATCTGTTAACATTATACGCGTTTAACCCTA

GAAAGATAATCATATTGTGACGTACGTTAAAGATAATCATGCGTAAAATT

GACGCATGTGTTTTATCGGTCTGTATATCGAGGTTTATTTATTAATTTGAA

TAGATATTAAGTTTTATTATATTTACACTTACATACTAATAATAAATTCAA

CAAACAATTTATTTATGTTTATTTATTTATTAAAAAAAAACAAAAACTCA

AAATTTCTTCTATAAAGTAACAAAACTTTTAAACATTCTCTCTTTTACAAA

AATAAACTTATTTTGTACTTTAAAAACAGTCATGTTGTATTATAAAATAA

GTAATTAGCTTAACCTATACATAATAGAAACAAATTATACTTA gBlock12-PV-3'TR-5'TR
                                          (SEQ ID NO: 90)
CCTATACATAATAGAAACAAATTATACTTATTAGTCAGTCAGAAACAACT

TTGGCACATATCAATATTATGCTCTGCTAGCGATATCTGTAAAACGACGG

CCAGTTCTAGACTTAAGCTTCATGGTCATAGCTGTTTCCTGCTCGAGTTAA
```

```
TTAACCAACAAGCTCGTCATCGCTTTGCAGAAGAGCAGAGAGGATATGCT

CATCGTCTAAAGAACTACCCATTTTATTATATATTAGTCACGATATCTATA

ACAAGAAAATATATATAATAAGTTATCACGTAAGTAGAACATGAAAT

AACAATA gBlock13-PV-3'TR-5'TR
                                              (SEQ ID NO: 91)
ATCACGTAAGTAGAACATGAAATAACAATATAATTATCGTATGAGTTAAA

TCTTAAAAGTCACGTAAAAGATAATCATGCGTCATTTTGACTCACGCGGT

CGTTATAGTTCAAAATCAGTGACACTTACCGCATTGACAAGCACGCCTCA

CGGGAGCTCCAAGCGGCGACTGAGATGTCCTAAATGCACAGCGACGGAT

TCGCGCTATTTAGAAAGAGAGAGCAATATTTCAAGAATGCATGCGTCAAT

TTTACGCAGACTATCTTTCTAGGGTTAATACGTATAATACATATGATTCAG

CTGCATTAATGAATC
```

The PB-EF1a-GW-iP vector (Masui H et al., PLOS ONE, 2014 Aug. 15; 9(8): e104957.) was cleaved with NheI-PacI, and then ligated to the NheI-PacI site of pPV-synthesized, to construct the pPV-EF1a-GW-iP vector. Subsequently, a rabbit-derived hemoglobin poly A signal was amplified from the pCXLE-EGFP vector (Okita K et al., Nat Methods, 2011 May; 8(5): 409-12.) using the pHL-PacI-rHBB-pA-IF-fw primer (5'-GTATACCTCGAGTTAAATTCACTCCTCAGGTGC-3' (SEQ ID NO:92)) and the pPV-PacI-rHBB-pA-IF-rev primer (5'-CGAGCTTGTTGGTTAATTAAGTCGAGGGATCTCCATAA-3' (SEQ ID NO:93)), and then inserted into the PacI site of the pPV-EF1a-GW-iP vector using the In-Fusion reaction, to construct the pPV-EF1a-GW-iP-A vector. By the Gateway LR reaction using the pPV-EF1a-GW-iP-A vector and pENTR-D-TOPO-Luc2-DMD-intron-Ex45 [+], the pPV-EF1a-Luc2-hDMD-Ex45[+]-iP-A vector was constructed. Further, by the Gateway LR reaction using the pPV-EF1a-GW-iP-A vector and pENTR-D-TOPO-Luc2-DMD-intron-Ex45[−], the pPV-EF1a-Luc2-hDMD-Ex45-[−]-iP-A vector was constructed.

<Introduction of Luc2 V323I (G867A) Mutation>

Using the piggyBac vector pPV-EF1a-Luc2-hDMD-Ex45 [−] vector as a template, PCR was carried out separately using, as primers, the combination of Luc2-NcoI-IF-Fwd and Luc2-V323I-fwd, and the combination of Luc2-V323I-rev and Luc2-SalI-IF-Rev. The two amplified fragments were mixed together, and the primers at both ends (Luc2-NcoI-IF-Fwd and Luc2-SalI-IF-Rev) were used to prepare a fragment having a mutation, followed by inserting the fragment into the NcoI-SalI cleavage site of the pPV-EF1a-Luc2-hDMD-Ex45[−] vector by the In-Fusion reaction, to construct the pPV-EF1a-Luc2(V323I)-hDMD-Ex45[−] vector.

```
        Luc2-NcoI-IF-Fwd
                                      (SEQ ID NO: 94)
        GCCCCCTTCACCATGGAAG

Luc2-V323I-fwd
                                      (SEQ ID NO: 95)
        CAGCAAGGAGATAGGTGAGG Luc2-V323I-rev
                                      (SEQ ID NO: 96)
        CCTCACCTATCTCCTTGCTG Luc2-SalI-IF-Rev
                                      (SEQ ID NO: 97)
        TAATGCAAACGTCGACAAATCAAAGAC
```

<Insertion of 1-kb, 2-kb, 4-kb, or 0.7-kb hDMD Exon 45, and Intron Sequences in Vicinity Thereof>

PCR amplification was carried out using pPV-EF1a-Luc2-hDMD-Ex45[+]-iP-A as a template, and using the DMD-Ex45-SalI-IF-F and DMD-Ex45-SalI-IF-R primers. The resulting product was inserted into the SalI cleavage site of the pPV-EF1α-Luc2(V323I)-hDMD-Ex45[−] vector by the In-Fusion reaction, to construct the pPV-EF1a-Luc2(V323I)-hDMD-Ex45 [+] (0.7 kb) vector.

```
        DMD-Ex45-SalI-IF-F
                                      (SEQ ID NO: 98)
        tattgatttGTCGACcgtatc DMD-Ex45-SalI-IF-R
                                      (SEQ ID NO: 99)
        taatgcaaacGTCGACgcc
```

Using, as a template, human genomic DNA prepared from 1383D2 cells, and using the following primers (HDMD-SR-XkbFrag-fwd & rev), exon 45 and the introns in the vicinity thereof were amplified. The resulting product was inserted into the SalI cleavage site of the pPV-EF1a-Luc2(V323I)-hDMD-Ex45[−] vector by the In-Fusion reaction, to construct the pPV-EF1a-Luc2(V323I)-hDMD-Ex45[+] (1 kb), pPV-EF1a-Luc2(V323I)-hDMD-Ex45[+] (2 kb), and pPV-EF1a-Luc2(V323I)-hDMD-Ex45[+] (4 kb) vectors.

```
        HDMD-SR-1kbFrag-fwd
                                      (SEQ ID NO: 100)
        tattgatttGTCGAGGGATATCTTGATGGGATGCTCC HDMD-SR-1kbFrag-rev
                                      (SEQ ID NO: 101)
        taatgcaaacGTCGAAAACCACTAACTAGCCACAAGT HDMD-SR-2kbFrag-fwd
                                      (SEQ ID NO: 102)
        tattgatttGTCGAATTGTGAGGCACCGTGTCAC HDMD-SR-2kbFrag-rev
                                      (SEQ ID NO: 103)
        taatgcaaacGTCGACTCTTTGGCTCAAGTTCCCCT HDMD-SR-4kbFrag-fwd
                                      (SEQ ID NO: 104)
        tattgatttGTCGAGCTGCAGCATTAGTTTATAGCA HDMD-SR-4kbFrag-rev
                                      (SEQ ID NO: 105)
        taatgcaaacGTCGAAACTTTGGCAAGGGGTGTGT
```

The sequences of the exon skipping reporter cDNA portion constructed are shown below.

```
Luc2(V323I)-hDMD-Ex45[-]
                                              (SEQ ID NO: 106)
ATGGAAGATGCCAAAAACATTAAGAAGGGCCCAGCGCCATTCTACCCAC

TCGAAGACGGGACCGCCGGCGAGCAGCTGCACAAAGCCATGAAGCGCTA

CGCCCTGGTGCCCGGCACCATCGCCTTTACCGACGCACATATCGAGGTGG

ACATTACCTACGCCGAGTACTTCGAGATGAGCGTTCGGCTGGCAGAAGCT

ATGAAGCGCTATGGGCTGAATACAAACCATCGGATCGTGGTGTGCAGCG

AGAATAGCTTGCAGTTCTTCATGCCCGTGTTGGGTGCCCTGTTCATCGGTG
```

TGGCTGTGGCCCCAGCTAACGACATCTACAACGAGCGCGAGCTGCTGAA
CAGCATGGGCATCAGCCAGCCCACCGTCGTATTCGTGAGCAAGAAAGGG
CTGCAAAAGATCCTCAACGTGCAAAAGAAGCTACCGATCATACAAAAGA
TCATCATCATGGATAGCAAGACCGACTACCAGGGCTTCCAAAGCATGTAC
ACCTTCGTGACTTCCCATTTGCCACCCGGCTTCAACGAGTACGACTTCGT
GCCCGAGAGCTTCGACCGGGACAAAACCATCGCCCTGATCATGAACAGT
AGTGGCAGTACCGGATTGCCCAAGGGCGTAGCCCTACCGCACCGCACCG
CTTGTGTCCGATTCAGTCATGCCCGCGACCCCATCTTCGGCAACCAGATC
ATCCCCGACACCGCTATCCTCAGCGTGGTGCCATTTCACCACGGCTTCGG
CATGTTCACCACGCTGGGCTACTTGATCTGCGGCTTTCGGGTCGTGCTCAT
GTACCGCTTCGAGGAGGAGCTATTCTTGCGCAGCTTGCAAGACTATAAGA
TTCAATCTGCCCTGCTGGTGCCCACACTATTTAGCTTCTTCGCTAAGAGCA
CTCTCATCGACAAGTACGACCTAAGCAACTTGCACGAGATCGCCAGCGG
CGGGGCGCCGCTCAGCAAGGAGaTAGGTGAGGCCGTGGCCAAACGCTTC
CACCTACCAGgtaagtattgatttGTCGACgtttgcattaacaaatagtt
tgagaactatgttggaaaaaaaaataacaattttattatattctccagGC
ATCCGCCAGGGCTACGGCCTGACAGAAACAACC
AGCGCCATTCTGATCACCCCCGAAGGGGACGACAAGCCTGGCGCAGTAG
GCAAGGTGGTGCCCTTCTTCGAGGCTAAGGTGGTGGACTTGGACACCGGT
AAGACACTGGGTGTGAACCAGCGCGGCGAGCTGTGCGTCCGTGGCCCCA
TGATCATGAGCGGCTACGTTAACAACCCCGAGGCTACAAACGCTCTCATC
GACAAGGACGGCTGGCTGCACAGCGGCGACATCGCCTACTGGGACGAGG
ACGAGCACTTCTTCATCGTGGACCGGCTGAAGAGCCTGATCAAATACAAG
GGCTACCAGGTAGCCCCAGCCGAACTGGAGAGCATCCTGCTGCAACACC
CCAACATCTTCGACGCCGGGGTCGCCGGCCTGCCCGACGACGATGCCGG
CGAGCTGCCCGCCGCAGTCGTCGTGCTGGAACACGGTAAAACCATGACC
GAGAAGGAGATCGTGGACTATGTGGCCAGCCAGGTTACAACCGCCAAGA
AGCTGCGCGGTGGTGTTGTGTTCGTGGACGAGGTGCCTAAAGGACTGACC
GGCAAGTTGGACGCCCGCAAGATCCGCGAGATTCTCATTAAGGCCAAGA
AGGGCGGCAAGATCGCCGTGTAA Luc2(V323I)-hDMD-Ex45[+]
(SEQ ID NO: 107)
ATGGAAGATGCCAAAAACATTAAGAAGGGCCCAGCGCCATTCTACCCAC
TCGAAGACGGGACCGCCGGCGAGCAGCTGCACAAAGCCATGAAGCGCTA
CGCCCTGGTGCCCGGCACCATCGCCTTTACCGACGCACATATCGAGGTGG
ACATTACCTACGCCGAGTACTTCGAGATGAGCGTTCGGCTGGCAGAAGCT
ATGAAGCGCTATGGGCTGAATACAAACCATCGGATCGTGGTGTGCAGCG
AGAATAGCTTGCAGTTCTTCATGCCCGTGTTGGGTGCCCTGTTCATCGGTG
TGGCTGTGGCCCCAGCTAACGACATCTACAACGAGCGCGAGCTGCTGAA
CAGCATGGGCATCAGCCAGCCCACCGTCGTATTCGTGAGCAAGAAAGGG
CTGCAAAAGATCCTCAACGTGCAAAAGAAGCTACCGATCATACAAAAGA
TCATCATCATGGATAGCAAGACCGACTACCAGGGCTTCCAAAGCATGTAC
ACCTTCGTGACTTCCCATTTGCCACCCGGCTTCAACGAGTACGACTTCGT
GCCCGAGAGCTTCGACCGGGACAAAACCATCGCCCTGATCATGAACAGT
AGTGGCAGTACCGGATTGCCCAAGGGCGTAGCCCTACCGCACCGCACCG
CTTGTGTCCGATTCAGTCATGCCCGCGACCCCATCTTCGGCAACCAGATC
ATCCCCGACACCGCTATCCTCAGCGTGGTGCCATTTCACCACGGCTTCGG
CATGTTCACCACGCTGGGCTACTTGATCTGCGGCTTTCGGGTCGTGCTCAT
GTACCGCTTCGAGGAGGAGCTATTCTTGCGCAGCTTGCAAGACTATAAGA
TTCAATCTGCCCTGCTGGTGCCCACACTATTTAGCTTCTTCGCTAAGAGCA
CTCTCATCGACAAGTACGACCTAAGCAACTTGCACGAGATCGCCAGCGG
CGGGGCGCCGCTCAGCAAGGAGaTAGGTGAGGCCGTGGCCAAACGCTTC
CACCTACCAGgtaagtctttgatttGTCGACcgtatccacgatcactaaga
aacccaaatactttgttcatgttttaaattttacaacatttcatagactatt
aaacatggaacatccttgtggggacaagaaatcgaatttgctcttgaaaag
gtttccaactaattgatttgtaggacattataacatcctctagctgacaag
cttacaaaaataaaaactggagctaaccgagagggtgctttttttccctgac
acataaaaggtgtattctgtatgtatcattggatatgggcatgtcagtttc
atagggaaattttcacatggagcttttgtatttattattgccagtacaact
gcatgtggtagcacactgtttaatctttttctcaaataaaaagacatggggc
TTCATTtttgttttgcctttttggtatcttacagGAACTCCAGGATGGCAT
TGGGCAGCGGCAAACTGTTGTCAGAACATTGAATGCAACTGGGGAAGAAAT
AATTCAGCAATCCTCAAAAACAGATGCCAGTATTCTACAGGAAAAATTGGG
AAGCCTGAATCTGCGGTGGCAGGAGGTCTGCAAACAGCTGTCAGACAGAAA
AAAGAGgtagggcgacagatctaataggaatgaaaacattttagcagactt
tttaagctttcttagaagaatatttcatgagagattataagcagggtgaa
aggcGTCGACgtttgcattaacaaatagtttgagaactatgttggaaaaaa
aaataacaattttattcttctttctccagGCATCCGCCAGGGCTACGGCCT
GACAGAAACAACCAGCGCCATTCTGATCACCCCCGAAGGGGACGACAAGCC
TGGCGCAGTAGGCAAGGTGGTGCCCTTCTTCGAGGCTAAGGTGGTGGACTT
GGACACCGGTAAGACACTGGGTGTGAACCAGCGCGGCGAGCTGTGCGTCCG
TGGCCCCATGATCATGAGCGGCTACGTTAACAACCCCGAGGCTACAAACGC
TCTCATCGACAAGGACGGCTGGCTGCACAGCGGCGACATCGCCTACTGGGA
CGAGGACGAGCACTTCTTCATCGTGGACCGGCTGAAGAGCCTGATCAAATA
CAAGGGCTACCAGGTAGCCCCAGCCGAACTGGAGAGCATCCTGCTGCAACA
CCCCAACATCTTCGACGCCGGGGTCGCCGGCCTGCCCGACGACGATGCCGG
CGAGCTGCCCGCCGCAGTCGTCGTGCTGGAACACGGTAAAACCATGACCGA
GAAGGAGATCGTGGACTATGTGGCCAGCCAGGTTACAACCGCCAAGAAGCT
GCGCGGTGGTGTTGTGTTCGTGGACGAGGTGCCTAAAGGACTGACCGGCAA
GTTGGACGCCCGCAAGATCCGCGAGATTCTCATTAAGGCCAAGAAGGGCGG
CAAGATCGCCGTGTAA Luc2(V323I)-hDMD-Ex45[+] (1 kb)
(SEQ ID NO: 108)
ATGGAAGATGCCAAAAACATTAAGAAGGGCCCAGCGCCATTCTACCCAC

TCGAAGACGGGACCGCCGGCGAGCAGCTGCACAAAGCCATGAAGCGCTA

CGCCCTGGTGCCCGGCACCATCGCCTTTACCGACGCACATATCGAGGTGG

ACATTACCTACGCCGAGTACTTCGAGATGAGCGTTCGGCTGGCAGAAGCT

ATGAAGCGCTATGGGCTGAATACAAACCATCGGATCGTGGTGTGCAGCG

AGAATAGCTTGCAGTTCTTCATGCCCGTGTTGGGTGCCCTGTTCATCGGTG

TGGCTGTGGCCCCAGCTAACGACATCTACAACGAGCGCGAGCTGCTGAA

CAGCATGGGCATCAGCCAGCCCACCGTCGTATTCGTGAGCAAGAAAGGG

CTGCAAAAGATCCTCAACGTGCAAAAGAAGCTACCGATCATACAAAAGA

TCATCATCATGGATAGCAAGACCGACTACCAGGGCTTCCAAAGCATGTAC

ACCTTCGTGACTTCCCATTTGCCACCCGGCTTCAACGAGTACGACTTCGT

GCCCGAGAGCTTCGACCGGGACAAAACCATCGCCCTGATCATGAACAGT

AGTGGCAGTACCGGATTGCCCAAGGGCGTAGCCCTACCGCACCGCACCG

CTTGTGTCCGATTCAGTCATGCCCGCGACCCCATCTTCGGCAACCAGATC

ATCCCCGACACCGCTATCCTCAGCGTGGTGCCATTTCACCACGGCTTCGG

CATGTTCACCACGCTGGGCTACTTGATCTGCGGCTTTCGGGTCGTGCTCAT

GTACCGCTTCGAGGAGGAGCTATTCTTGCGCAGCTTGCAAGACTATAAGA

TTCAATCTGCCCTGCTGGTGCCCACACTATTTAGCTTCTTCGCTAAGAGCA

CTCTCATCGACAAGTACGACCTAAGCAACTTGCACGAGATCGCCAGCGG

CGGGGCGCCGCTCAGCAAGGAGaTAGGTGAGGCCGTGGCCAAACGCTTC

CACCTACCAGgtaagtattgatttGTCGAAGCACGCATTTGGCTTTCTGTG

CCTTCAATACATTCCAAGGGAAATTTAAATGATGATTGAATTTGACAGTAA

CCTTTTTGAGGTTTTGTTTTCCCCATTAAACTTGTACCTCTTTGGCTCAAG

TTCCCCTTCAAGAATGTATTCACAAATGTGGTGAAACTAGAGGTAAGTGAC

ACTATCACTTTTTTTAGCTTCATAGTCATATTCATAGCTATTTTTAAAACT

AAGCAAAGATCTGTCTTTCCTACAAAACAATCATTTATAATTGCTTTCTAA

AATCTTCTTGAAAAACAACTGAGATTCAGCTTGTTGAAGTTAAAATATATT

GAAGATATTCACCTTTAAGCAATCATGGGTGATTTTTAAAGCAAACTTCAA

GTTTAAAATAGCAGAAAACCACTAACTAGCCACAAGTATATATTTTAGTAT

ATGAAAAAAGAAATAAAAAATTTCTTTACTGCTGTTGATTAATGGTTGA

TAGGTTCTTTAATGTTAGTGCCTTTCACCCTGCTTATAATCTCTCATGAAA

TATTCTTCTAAAGAAAGCTTAAAAAGTCTGCTAAAATGTTTTCATTCCTAT

TAGATCTGTCGCCCTACCTCTTTTTTCTGTCTGACAGCTGTTTGCAGACCT

CCTGCCACCGCAGATTCAGGCTTCCCAATTTTTCCTGTAGAATACTGGCA

TCTGTTTTTGAGGATTGCTGAATTATTTCTTCCCCAGTTGCATTCAATGTT

CTGACAACAGTTTGCCGCTGCCCAATGCCATCCTGGAGTTCCTGTAAGAT

ACCAAAAAGGCAAAACAAAAATGAAGCCCCATGTCTTTTTATTTGAGAA

AAGATTAAACAGTGTGCTACCACATGCAGTTGTACTGGCAAAGAAAGAA

ATACAAAAGCTCCATGTGAAAATTTCCCTATGAAACTGACATGCCCTCGA

Cgtttgcattaacaaatagtttgagaactatgttggaaaaaaaaataacaa ttttattcttattaccagGCATCCGCC

AGGGCTACGGCCTGACAGAAACAACCAGCGCCATTCTGATCACCCCCGA

AGGGGACGACAAGCCTGGCGCAGTAGGCAAGGTGGTGCCCTTCTTCGAG

GCTAAGGTGGTGGACTTGGACACCGGTAAGACACTGGGTGTGAACCAGC

GCGGCGAGCTGTGCGTCCGTGGCCCCATGATCATGAGCGGCTACGTTAAC

AACCCCGAGGCTACAAACGCTCTCATCGACAAGGACGGCTGGCTGCACA

GCGGCGACATCGCCTACTGGGACGAGGACGAGCACTTCTTCATCGTGGA

CCGGCTGAAGAGCCTGATCAAATACAAGGGCTACCAGGTAGCCCCAGCC

GAACTGGAGAGCATCCTGCTGCAACACCCCAACATCTTCGACGCCGGGG

TCGCCGGCCTGCCCGACGACGATGCCGGCGAGCTGCCCGCCGCAGTCGTC

GTGCTGGAACACGGTAAAACCATGACCGAGAAGGAGATCGTGGACTATG

TGGCCAGCCAGGTTACAACCGCCAAGAAGCTGCGCGGTGGTGTTGTGTTC

GTGGACGAGGTGCCTAAAGGACTGACCGGCAAGTTGGACGCCCGCAAGA

TCCGCGAGATTCTCATTAAGGCCAAGAAGGGCGGCAAGATCGCCGTGTA

A

Luc2(V323I)-hDMD-Ex45[+] 2 kb
(SEQ ID NO: 109)
ATGGAAGATGCCAAAAACATTAAGAAGGGCCCAGCGCCATTCTACCCAC

TCGAAGACGGGACCGCCGGCGAGCAGCTGCACAAAGCCATGAAGCGCTA

CGCCCTGGTGCCCGGCACCATCGCCTTTACCGACGCACATATCGAGGTGG

ACATTACCTACGCCGAGTACTTCGAGATGAGCGTTCGGCTGGCAGAAGCT

ATGAAGCGCTATGGGCTGAATACAAACCATCGGATCGTGGTGTGCAGCG

AGAATAGCTTGCAGTTCTTCATGCCCGTGTTGGGTGCCCTGTTCATCGGTG

TGGCTGTGGCCCCAGCTAACGACATCTACAACGAGCGCGAGCTGCTGAA

CAGCATGGGCATCAGCCAGCCCACCGTCGTATTCGTGAGCAAGAAAGGG

CTGCAAAAGATCCTCAACGTGCAAAAGAAGCTACCGATCATACAAAAGA

TCATCATCATGGATAGCAAGACCGACTACCAGGGCTTCCAAAGCATGTAC

ACCTTCGTGACTTCCCATTTGCCACCCGGCTTCAACGAGTACGACTTCGT

GCCCGAGAGCTTCGACCGGGACAAAACCATCGCCCTGATCATGAACAGT

AGTGGCAGTACCGGATTGCCCAAGGGCGTAGCCCTACCGCACCGCACCG

CTTGTGTCCGATTCAGTCATGCCCGCGACCCCATCTTCGGCAACCAGATC

ATCCCCGACACCGCTATCCTCAGCGTGGTGCCATTTCACCACGGCTTCGG

CATGTTCACCACGCTGGGCTACTTGATCTGCGGCTTTCGGGTCGTGCTCAT

GTACCGCTTCGAGGAGGAGCTATTCTTGCGCAGCTTGCAAGACTATAAGA

TTCAATCTGCCCTGCTGGTGCCCACACTATTTAGCTTCTTCGCTAAGAGCA

CTCTCATCGACAAGTACGACCTAAGCAACTTGCACGAGATCGCCAGCGG

CGGGGCGCCGCTCAGCAAGGAGaTAGGTGAGGCCGTGGCCAAACGCTTC

CACCTACCAGgtaagtattgatttGTCGATCTTTAACTTTGGCAAGGGGTG

TGTGTGTGTGTGTGTGTGTGTGTGTGTGTGTGTGTGTGTGTGTGTGTGT

GTGTTTAGGTCAACTAATGTGTTTATTTTGTACAAAATATGAATTGTATCT

ACTTTCTGAATAATGTAACATGAATAAAGAGGGAAAGAGGAGGTGGGCAAA

-continued

```
GACAACTGACATAATTCCAAAATCTTCTTTTTAATACATCTTAACGAAAGA
TATTCATCAATGAGTTGTTCTAGCTTCCTGAATATTAAAATCCACCTATTA
TGTGGATGATGGGTGGGATGCAAGAGCTTGGCAAAAGAACGAAGTTTTCA
TTGTTCATAACAATAGTCTCATTTGGTAAATAAAGGCCAAGTCTTCCTTTA
CGAAACAAGACACATTAACATCAACAACTGGAAGCATAATACAAAATCC
CATTTATAAACTCTCTAGGCTTTCCAACTGCAGCAGCACGCATTTGGCTTT
CTGTGCCTTCAATACATTCCAAGGGAAATTTAAATGATGATTGAATTTGA
CAGTAACCTTTTTGAGGTTTTGTTTTCCCCATTAAACTTGTACCTCTTTGG
CTCAAGTTCCCCTTCAAGAATGTATTCACAAATGTGGTGAAACTAGAGGT
AAGTGACACTATCACTTTTTTTAGCTTCATAGTCATATTCATAGCTATTTT
TAAAACTAAGCAAAGATCTGTCTTTCCTACAAAACAATCATTTATAATTG
CTTTCTAAAATCTTCTTGAAAAACAACTGAGATTCAGCTTGTTGAAGTTA
AAATATATTGAAGATATTCACCTTTAAGCAATCATGGGTGATTTTAAAG
CAAACTTCAAGTTTAAAATAGCAGAAAACCACTAACTAGCCACAAGTAT
ATATTTTAGTATATGAAAAAAGAAATAAAAAATTTCTTTACTGCTGTTG
ATTAATGGTTGATAGGTTCTTTAATGTTAGTGCCTTTCACCCTGCTTATAA
TCTCTCATGAAATATTCTTCTAAAGAAAGCTTAAAAAGTCTGCTAAAATG
TTTTCATTCCTATTAGATCTGTCGCCCTACCTCTTTTTTCTGTCTGACAGC
TGTTTGCAGACCTCCTGCCACCGCAGATTCAGGCTTCCCAATTTTTCCTGT
AGAATACTGGCATCTGTTTTTGAGGATTGCTGAATTATTTCTTCCCCAGTT
GCATTCAATGTTCTGACAACAGTTTGCCGCTGCCCAATGCCATCCTGGAGT
TCCTGTAAGATACCAAAAAGGCAAAACAAAAATGAAGCCCCATGTCTTTT
TATTTGAGAAAAGATTAAACAGTGTGCTACCACATGCAGTTGTACTGGCA
AAGAAAGAAATACAAAAGCTCCATGTGAAAATTTCCCTATGAAACTGAC
ATGCCCATATCCAAAGGATACAAGACAGAAAGACACCTTTTATGTGTCAG
GGAAAAAAGCACCCTCTCGGTTAGCTCCAGTTTTTATTTTTGTAAGCTTGT
CAGCTAGAGGATGTTATAATGTCCTACAAATCAATTAGTTGGAAACCTTT
TCAAGAGCAAATTCGATTTCTTGTCCCCACAAGGATGTTCCATGTTTAAT
AGTCTATGAAATGTTGTAAAATTTAAACATGAACAAAGTATTTGGGTTTC
TTAGTGATCGTGGATACGAGAGGTGAAAAAGAACAAACATAGGTTAGTC
ACAGTATTAAAAAAAAACTCTAGAGATATTTAAATAAAATTAATTGCTAT
ATTAGAAGAAAATTCATTTCAAATTCTGTCTGCGTCAATGTATTTTGCATT
AGAAGCCACAAAAAACTGAGAATTAATTGCTTTCAGGAGCATCCCATCA
AGATATCCCTAAGCTACAGTAATAAATTTTAAAATAATCTATAGTCACCA
GAGCATTTTATGATTGTCATCGACgtttgcattaacaaatagtttgagaa
ctatgttggaaaaaaaaataacaattttattatattctccagGCATCCGCC
AGGGCTACGGCCTGACAGAAACAACCAGCGCCATTCTGATCACCCCCGAAG
GGGACGACAAGCCTGGCGCAGTAGGCAAGGTGGTGCCCTTCTTCGAGGCTA
AGGTGGTGGACTTGGACACCGGTAAGACACTGGGTGTGAACCAGCGCGGCG
AGCTGTGCGTCCGTGGCCCCATGATCATGAGCGGCTACGTTAACAACCCCG
```

Luc2(V323I)-hDMD-Ex45[+] (4 kb)
(SEQ ID NO: 110)

```
AGGCTACAAACGCTCTCATCGACAAGGACGGCTGGCTGCACAGCGGCGACA
TCGCCTACTGGGACGAGGACGAGCACTTCTTCATCGTGGACCGGCTGAAGA
GCCTGATCAAATACAAGGGCTACCAGGTAGCCCCAGCCGAACTGGAGAGCA
TCCTGCTGCAACACCCCAACATCTTCGACGCCGGGGTCGCCGGCCTGCCCG
ACGACGATGCCGGCGAGCTGCCCGCCGCAGTCGTCGTGCTGGAACACGGTA
AAACCATGACCGAGAAGGAGATCGTGGACTATGTGGCCAGCCAGGTTACAA
CCGCCAAGAAGCTGCGCGGTGGTGTTGTGTTCGTGGACGAGGTGCCTAAAG
GACTGACCGGCAAGTTGGACGCCCGCAAGATCCGCGAGATTCTCATTAAGG
CCAAGAAGGGCGGCAAGATCGCCGTGTAA
ATGGAAGATGCCAAAAACATTAAGAAGGGCCCAGCGCCATTCTACCCAC
TCGAAGACGGGACCGCCGGCGAGCAGCTGCACAAAGCCATGAAGCGCTA
CGCCCTGGTGCCCGGCACCATCGCCTTTACCGACGCACATATCGAGGTGG
ACATTACCTACGCCGAGTACTTCGAGATGAGCGTTCGGCTGGCAGAAGCT
ATGAAGCGCTATGGGCTGAATACAAACCATCGGATCGTGGTGTGCAGCG
AGAATAGCTTGCAGTTCTTCATGCCCGTGTTGGGTGCCCTGTTCATCGGTG
TGGCTGTGGCCCCAGCTAACGACATCTACAACGAGCGCGAGCTGCTGAA
CAGCATGGGCATCAGCCAGCCCACCGTCGTATTCGTGAGCAAGAAAGGG
CTGCAAAAGATCCTCAACGTGCAAAAGAAGCTACCGATCATACAAAGA
TCATCATCATGGATAGCAAGACCGACTACCAGGGCTTCCAAAGCATGTAC
ACCTTCGTGACTTCCCATTTGCCACCCGGCTTCAACGAGTACGACTTCGT
GCCCGAGAGCTTCGACCGGGACAAAACCATCGCCCTGATCATGAACAGT
AGTGGCAGTACCGGATTGCCCAAGGGCGTAGCCCTACCGCACCGCACCG
CTTGTGTCCGATTCAGTCATGCCCGCGACCCCATCTTCGGCAACCAGATC
ATCCCCGACACCGCTATCCTCAGCGTGGTGCCATTTCACCACGGCTTCGG
CATGTTCACCACGCTGGGCTACTTGATCTGCGGCTTTCGGGTCGTGCTCAT
GTACCGCTTCGAGGAGGAGCTATTCTTGCGCAGCTTGCAAGACTATAAGA
TTCAATCTGCCCTGCTGGTGCCCACACTATTTAGCTTCTTCGCTAAGAGCA
CTCTCATCGACAAGTACGACCTAAGCAACTTGCACGAGATCGCCAGCGG
CGGGGCGCCGCTCAGCAAGGAGaTAGGTGAGGCCGTGGCCAAACGCTTC
CACCTACCAGgtaagtattgatttGTCGATTTGCAACTACAGGGCTCCATA
TAGACATCTAGCTTGAATTTATACACTTTCTTTCATTGATGTCCCTGGACT
AAAAAATGTTAAATATTTCTAACCGCTGTACTTAAAGTCCATTACAAACGA
AGACTACTGTTGTTAAGTTGAATAGGCATCTTATATATTTTTCACCGGTGC
AATAAATAACTTCTATTCCCTTCTAACATCTGCTTGCGTTGCACTGAGAGT
ACACTATTGATTAGCAATAGGTTCGTGATTACAGCCCTTCTATAATTAATT
GTTAGGTTAACATATTATTCATAAAATATTATTTTATTAATTTTTACTTGA
TTTGCTACTGGATGCTTAGAAATAGCTATGAGTATATTGGTAGAACCAGTA
CTTATATTTTATTACATTTTTACATTTCATAAAATTTAAGTGATATAAAAA
TCCTGAGGAAGTATGCCACAAAAGTGGTCTCAGTGGAAATTTAAATATGTT
AACATTTATTTTTAAAATGTAGCGTGAAATAGACAACTTTAAAAGCTCAGC
```

TTAAAAAAAAAAACTCAAGGAAGCTGAACTTGACTTTTTAAAGCACTGAAG

TGCAATATTTAATGTAGGTCAACATGTTTAAATGGGAAAATTTTTTTCCTA

ATTACAGCCAAATCCCTAGCTGTAATTAACTTAAAATTTGTATACTATTTC

ACAACAGAGTCAGCATATACCACTTTCTTATAAAATTAGAAAGATCTAAA

ATTTTAGAGCTTATTTGGTGAAACAGGCATATTGCTACATCTTTGTTTATA

AATTATAATGTGCCTTTAGAGCCCAATAACAGATAACAAGATTTTGAAAA

TTCAGGTGAATTAGAGTTATCAGAGGGAATGTTAATACACTCTATTCAAA

TACTATATGAGTAAGACATTTAAAATAGGAAACAATACTTTATATATTAT

AGAAAAATAATCTTCCAGTCGATTTAATCCACTTTATGAATTCTCTCCGTA

TATATATATTTATAGTATGGTATTCAATTTTTTTAATTTTCTCATTTCTTA

CCATCTTAATTTGGATTAGATTGAGCCTAGTTCAGAAATGACATTATACAG

GTTTATACCTGTTCATAGTATAAGCACATCAGTTATCTAAATAATAAAAT

ACTTGTATGATTAAGAGAAGAATTTCAATCTGGGAAAAAGTATATGACT

TACCTAAGGAAGTAGTTTAACTACAAAGTTTAGTTCTTTATTTTATCTATC

TATAATCAAGAAGATTTTCAAAACCAAGACTTAATTATTCAAAATATCTT

TTGATGAGGCTATAATTCTTTAACTTTGGCAAGGGGTGTGTGTGTGTGTGT

GTGTGTGTGTGTGTGTGTGTGTGTGTGTGTGTGTGTGTTTAGGTCAA

CTAATGTGTTTATTTTGTACAAAATATGAATTGTATCTACTTTCTGAATAA

TGTAACATGAATAAAGAGGGAAAGAGGAGGTGGGCAAAGACAACTGAC

ATAATTCCAAAATCTTCTTTTTAATACATCTTAACGAAAGATATTCATCAA

TGAGTTGTTCTAGCTTCCTGAATATTAAAATCCACCTATTATGTGGATGAT

GGGTGGGATGCAAGAGCTTGGCAAAAGAACGAAGTTTTCATTGTTCATA

ACAATAGTCTCATTTGGTAAATAAAGGCCAAGTCTTCCTTTACGAAACAA

GACACATTAACATCAACAACTGGAAGCATAATACAAAATCCCATTTATAA

ACTCTCTAGGCTTTCCAACTGCAGCAGCACGCATTTGGCTTTCTGTGCCTT

CAATACATTCCAAGGGAAATTTAAATGATGATTGAATTTGACAGTAACCT

TTTTGAGGTTTTGTTTTCCCCATTAAACTTGTACCTCTTTGGCTCAAGTTC

CCCTTCAAGAATGTATTCACAAATGTGGTGAAACTAGAGGTAAGTGACACT

ATCACTTTTTTTAGCTTCATAGTCATATTCATAGCTATTTTTAAAACTAAG

CAAAGATCTGTCTTTCCTACAAAACAATCATTTATAATTGCTTTCTAAAAT

CTTCTTGAAAAACAACTGAGATTCAGCTTGTTGAAGTTAAAATATATTGA

AGATATTCACCTTTAAGCAATCATGGGTGATTTTAAAGCAAACTTCAAG

TTTAAAATAGCAGAAAACCACTAACTAGCCACAAGTATATATTTTAGTAT

ATGAAAAAAGAAATAAAAAATTTCTTTACTGCTGTTGATTAATGGTTGA

TAGGTTCTTTAATGTTAGTGCCTTTCACCCTGCTTATAATCTCTCATGAAA

TATTCTTCTAAAGAAAGCTTAAAAAGTCTGCTAAAATGTTTTCATTCCTAT

TAGATCTGTCGCCCTACCTCTTTTTTCTGTCTGACAGCTGTTTGCAGACCT

CCTGCCACCGCAGATTCAGGCTTCCCAATTTTTCCTGTAGAATACTGGCA

TCTGTTTTTGAGGATTGCTGAATTATTTCTTCCCCAGTTGCATTCAATGTT

CTGACAACAGTTTGCCGCTGCCCAATGCCATCCTGGAGTTCCTGTAAGAT

ACCAAAAAGGCAAAACAAAAATGAAGCCCCATGTCTTTTTATTTGAGAA

AAGATTAAACAGTGTGCTACCACATGCAGTTGTACTGGCAAAGAAAGAA

ATACAAAAGCTCCATGTGAAAATTTCCCTATGAAACTGACATGCCCATAT

CCAAAGGATACAAGACAGAAAGACACCTTTTATGTGTCAGGGAAAAAG

CACCCTCTCGGTTAGCTCCAGTTTTTATTTTTGTAAGCTTGTCAGCTAGAG

GATGTTATAATGTCCTACAAATCAATTAGTTGGAAACCTTTTCAAGAGCA

AATTCGATTTCTTGTCCCCACAAGGATGTTCCATGTTTAATAGTCTATGAA

ATGTTGTAAAATTTAAACATGAACAAAGTATTTGGGTTTCTTAGTGATCG

TGGATACGAGAGGTGAAAAAGAACAAACATAGGTTAGTCACAGTATTAA

AAAAAAACTCTAGAGATATTTAAATAAAATTAATTGCTATATTAGAAGAA

AATTCATTTCAAATTCTGTCTGCGTCAATGTATTTTGCATTAGAAGCCACA

AAAAACTGAGAATTAATTGCTTTCAGGAGCATCCCATCAAGATATCCCTA

AGCTACAGTAATAAATTTTAAAATAATCTATAGTCACCAGAGCATTTTTA

TGATTGTCAAGCTTAAATATTGTTTACTTTTTTCCTGAATGAAATTTTAAG

AGTAAAGTATCAGAAAAATAGCTCAATTGAAAAGGAGAATATTACAACC

AAGTACACACAAAAACAAAAATGCTTTTTACCATTAAATAAAAATGGCA

ATTACGTTCTATTTAACTTTTTAAAAAAGATAATCTAGAATTTGTAAGGCC

ATTAAAATAACATATTAACTAAATACGAACCTTAGAAAATGAAATAATAT

CTGAGAACTTGAGGTACCTACCGTATTTAAATCTGAATGACTCAAATCCT

TATGTCACTGACAGAATAATGTGCGTATGTAGAAAACTCTCCTAATAGAT

GTGATTCATATTCTCTAATATTTTTGTATTCTCCTACTCCTTGACACAATA

GCAAGCTGACAGTAGACCCCAGTACATGCTTCCTAAATGAAGGAAGGAA

TGCATGTTTTCTGAGACTGAGGTAAAGCTCCCTTAGACTCTCGTTTCACAT

ACATTTCTTGGCTTTTTTCTTTTTCTACATTCAAGCAAAATTATTTTCGAA

TACTGGAAATTTTGGTAGCATACAGTTAGCAATTAAAATACTCTGTAAATC

AGCAAACCGGTGACACGGTGCCTCACAATGAATATAAAACTATGCACAG

TTACTGAACTATTCACAAGCTGTCCTGGCCATACTCTCTTGAATGCCCATG

AGATGTGCTCTAGTAAACATGTGATATTTCCTTGTAACTAGTTGGCTTTGC

TCCATTGCTCGACgtttgcattaacaaatagtttgagaactatgttggaaa aaaaaataacaatttt attcttctttct ccagGCATCCGCCAGGGCTACGGCCTGACAGAAACAACCAGCGCCATTCTG

ATCACCCCGAAGGGGACGACAAGCCTGGCGCAGTAGGCAAGGTGGTGC

CCTTCTTCGAGGCTAAGGTGGTGGACTTGGACACCGGTAAGACACTGGGT

GTGAACCAGCGCGCGAGCTGTGCGTCCGTGGCCCCATGATCATGAGCG

GCTACGTTAACAACCCCGAGGCTACAAACGCTCTCATCGACAAGGACGG

CTGGCTGCACAGCGGCGACATCGCCTACTGGGACGAGGACGAGCACTTC

TTCATCGTGGACCGGCTGAAGAGCCTGATCAAATACAAGGGCTACCAGG

TAGCCCCAGCCGAACTGGAGAGCATCCTGCTGCAACACCCCAACATCTTC

GACGCCGGGGTCGCCGGCCTGCCCGACGACGATGCCGGCGAGCTGCCCG

CCGCAGTCGTCGTGCTGGAACACGGTAAAACCATGACCGAGAAGGAGAT

CGTGGACTATGTGGCCAGCCAGGTTACAACCGCCAAGAAGCTGCGCGGT

-continued

GGTGTTGTGTTCGTGGACGAGGTGCCTAAAGGACTGACCGGCAAGTTGG

ACGCCCGCAAGATCCGCGAGATTCTCATTAAGGCCAAGAAGGGCGGCAA

GATCGCCGTGTAA

<Exon Skipping Reporter Assay Using Luc Reporter>

A mixture of 40 ng of the pPV-EF1a-Luc2(V323I)hDMD-Ex45[+] vector, 20 ng of the phRL-TK vector, which expresses Renilla Luc, 280 ng of the pHL-EF1a vector (Addgene), which expresses CRISPR-Cas, and 280 ng of the pHL-H1-sgRNA-mEF1a-RiH vector, which expresses a guide RNA, was prepared, and then diluted with 25 µl of Opti-MEM. With 25 µl of Opti-MEM, 0.7 µl of Lipofectamine 2000 was diluted, and the resulting dilution was incubated at room temperature for 3 to 5 minutes, followed by mixing the dilution with the above DNA solution, and then incubating the resulting mixture at room temperature for additional 20 minutes. The cell number of 293T cells suspended by trypsin-EDTA treatment was counted, and then the cells were diluted to 60,000 cells/100 µl with a medium, followed by plating the cells on a 96-well plate containing the above DNA-Lipofectamine complex at 100 µl/well. After culturing the cells for 48 hours with 5% $CO_2$ at 37° C., the 96-well plate was allowed to cool to room temperature, and then Dual-Glo Reagent was added thereto, followed by incubation at room temperature for 30 minutes to lyse the cells to cause the luciferase reaction. To a white 96-well plate, 100 µl of the supernatant was transferred, and the luminescence intensities of Firefly and Renilla were measured using Centro LB960 (Berthold Technologies). Since firefly Luc emits light only when exon skipping is induced, the luminescence value of firefly was normalized against the luminescence value of Renilla to measure the exon skipping efficiency.

<Results>

In order to develop a therapeutic method for Duchenne muscular dystrophy, induction of exon skipping in the dystrophin gene was studied. FIG. 1 shows its overview.
(1) In the skeletal muscle isoform (Dp427m) of the dystrophin gene in healthy individuals, 79 exons are linked to each other by splicing, and a dystrophin protein composed of 3685 amino acids is encoded.
(2) However, in DMD patients lacking exon 44, the size of exon 44 is not a multiple of 3, and therefore the reading frame of the protein shifts to generate a stop codon in the following exon 45, resulting in discontinuity of the dystrophin protein.
(3) Here, by disrupting the splice acceptor sequence portion of exon 45 by genome editing, recognition of exon 45 can be prevented during splicing, so that, instead, the following exon 46 can be linked to exon 43, resulting in recovery of the reading frame of the dystrophin protein.

The splice acceptor is constituted by a branching sequence, polypyrimidine (C/U) sequence, and an "AG" acceptor sequence. Since, among these, the "AG" acceptor sequence is most highly conserved during the splicing reaction, deletion of these two bases may enable induction of exon skipping.

Figure 2:
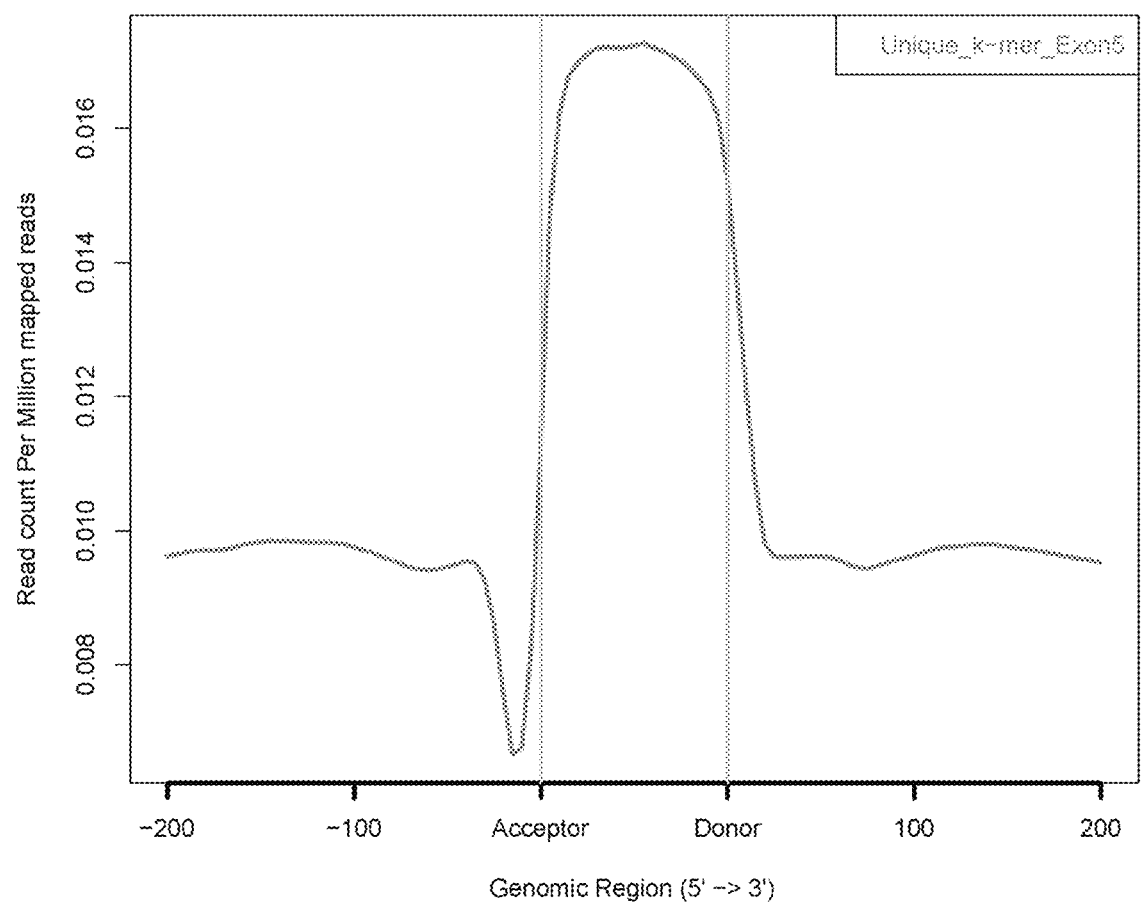
FIG. 2 shows that the sequence specificity of the splice acceptor sequence region is generally low, and that similar sequences are present also in other regions in the genome, indicating that designing of a highly specific CRISPR guide RNA and the like therefor is difficult. Among arbitrary DNA sequences having lengths of 10 bases to 16 bases, unique sequences (unique k-mer) present only at one position in a human genome sequence (hg19) were used to prepare a database, and the distribution of the unique sequences was plotted in terms of the relative positions in all exons of the human RefSeq genes. It can be seen that the inside of human exons generally shows accumulation of unique sequences and hence high specificity, but that the splice acceptor portion has very low specificity.

In designing of gRNAs for CRISPR systems, from the viewpoint of the off-target risk, that is, recognition and cleavage of sequences other than the target sequence in the genome, the unique k-mer method [Li H L et al., Stem Cell Reports, 2015] was used to investigate the sequence specificity in the region around the splice acceptor. As a result, it became clear that the region near the splice acceptor has an especially low specificity compared to the exon regions and other intron regions (FIG. 2).

Figure 5:
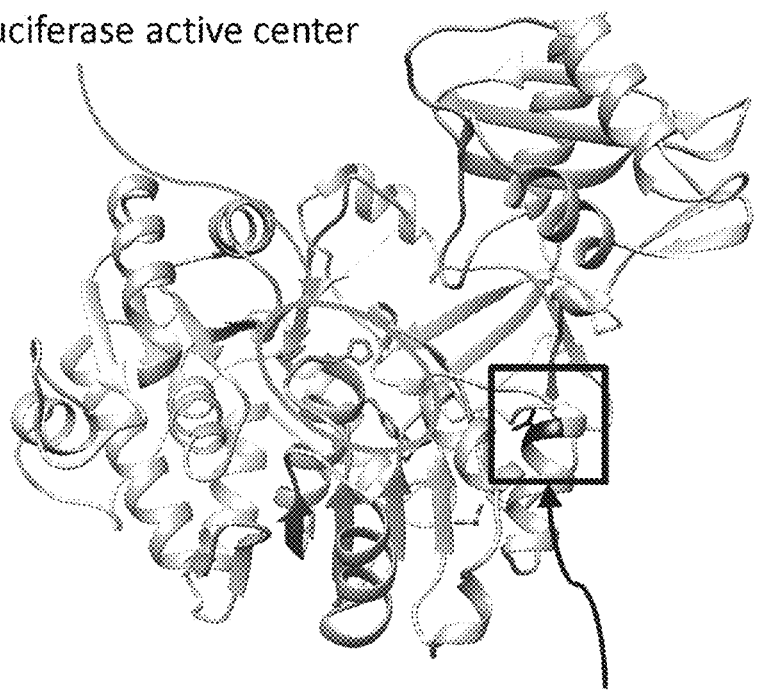
FIG. 5 shows the result of analysis of the crystal structure of the firefly luciferase protein (PDB code: 1BA3) for prediction of the influence of the amino acid modification site on the activity of the firefly luciferase. Since the Val residue at the 323th position (square) was sufficiently distant from the active-center residue (circle) [Branchini B R et al., JBC, 1997], it was expected that there may be no direct interaction, and that the modification of this amino acid may hardly influence the enzyme activity. Since the Val residue is positioned in the middle of the α-helix, it was altered to an Ile residue, which is less likely to change the α-helix structure, and which has a similar structure and chemical properties.

In order to simply and highly sensitively detect the exon skipping efficiency in the dystrophin gene, a reporter vector was constructed using the firefly luciferase (Luc) gene. A vector in which Luc cDNA was divided into two parts, and a synthetic intron sequence was inserted thereto (Luc+Int), and a vector in which a sequence around human dystrophin exon 45 was further inserted thereto (Luc+hEx45), were prepared (FIG. 3). Each vector was introduced into 293T cells, and mRNA was recovered, followed by performing reverse transcription and then PCR amplification. As a result, it was found that the first half of the Luc cDNA contains a pseudo-splicing donor sequence, causing extra splicing (FIG. 4, Panel (a)). In order to disrupt this pseudo-splicing donor sequence, splicing donor sequences and acceptor sequences were extracted from all exon sequences contained in the human dystrophin gene from the Ensemble Biomart database (http://www.ensembl.org), and common bases were analyzed with Weblogo software (http://weblogo.threeplusone.com/). As a result, they were found to be matching well with known splicing donor and acceptor sequences (FIG. 4, Panel (b)). Thus, it was expected that, by converting the "G" at the center of the pseudo-splicing donor sequence "AG<u>G</u>TA" to a "sequence other than G", the pseudo-splicing donor sequence can be prevented from functioning as a splicing donor. However, since this base is the first base of the codon "<u>G</u>TA", which encodes a Val amino acid, alteration of this base inevitably changes the amino acid sequence. Alteration to "A" results in generation of the codon "<u>A</u>TA", which encodes an Ile amino acid (FIG. 4, Panel (c)), and alteration to "C" or "T" results in generation of a codon "<u>C</u>TA" or "<u>T</u>TA", which encodes a Leu Amino acid. In order to confirm that this amino acid conversion does not affect the Luc activity, the present inventors downloaded the spatial structure of luciferase protein (PDB code: 1BA3) from the PDB database. By using Chimera software, it could be confirmed that the G967A (V323I) mutant amino acid site is distant from the active residue [Branchini B R et al., J Biol Chem. 1997 Aug. 1; 272(31): 19359-64.], and hence that there is no direct interaction (FIG. 5).

Figure 6:
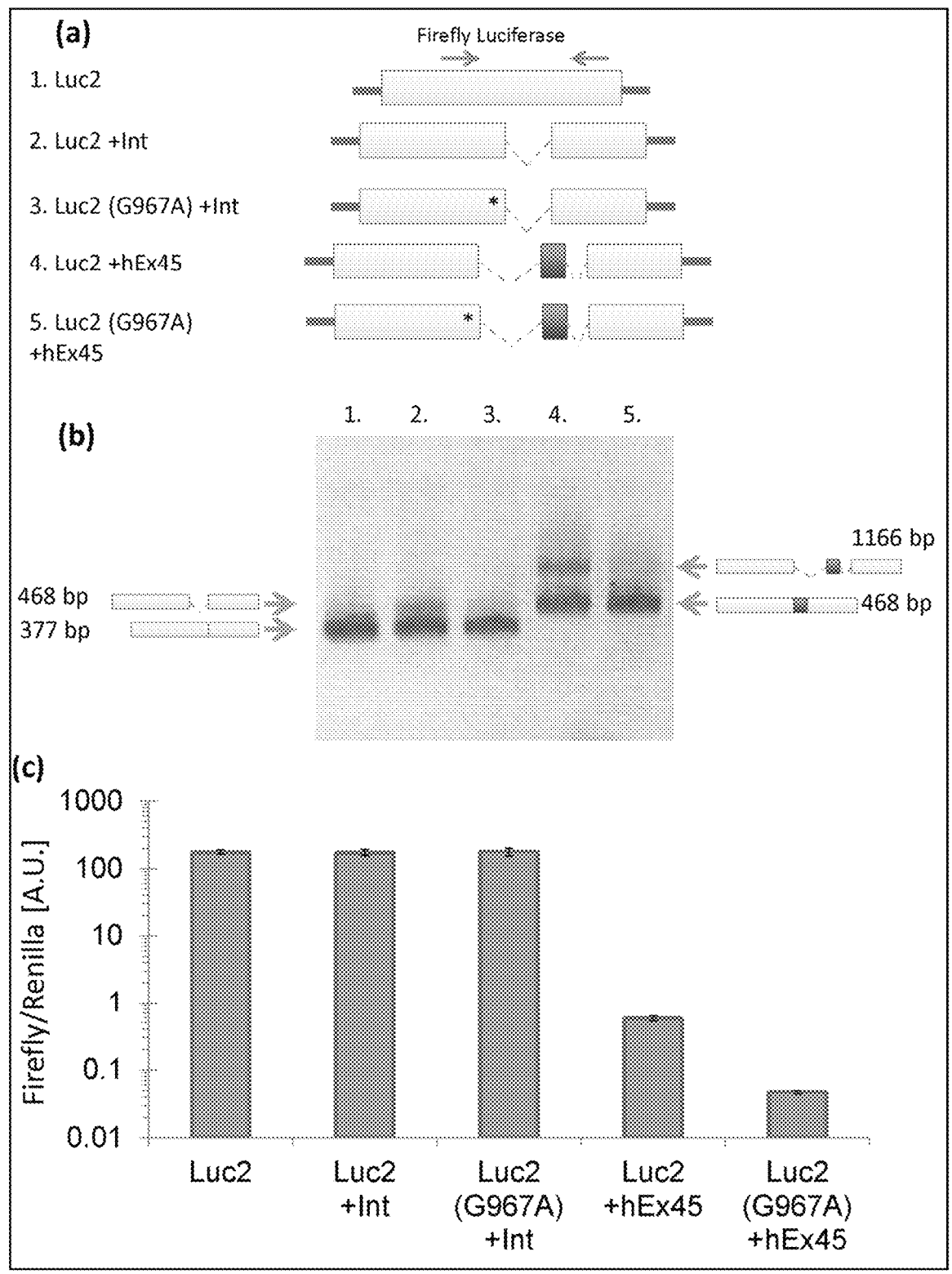
FIG. 6 shows the results of investigation of the influence of the G967A (V323I) mutation on splicing and the Luc activity. Panel (a) shows Luc expression cassettes used for comparative analysis. All of these were prepared by insertion into the piggyBac vector (System Biosciences) pPV-EF1a-GW-iP-A. * represents the G967A (V323I) mutation; each dotted line represents an intron; and each box represents an exon. Panel (b) shows the results of analysis of the splicing pattern, which analysis was carried out by introducing each vector into 293T cells, extracting mRNA therefrom, and then performing PCR with primers including an intron portion. Lane 2, which is for a case where the intron was inserted into Lu2, showed a band indicating remaining of the intron (468 bp) as well as a band (377 bp) indicating occurrence of the expected splicing. Lane 4, which is for a case where exon 45 of dystrophin was inserted, showed the same trend, showing a band of 1166 bp including the intron as well as the band of 468 bp which indicates occurrence of the expected splicing. Lane 3 and lane 5, which are for cases where the point mutation (G967A (V323I) mutation) was introduced into the Luc2 cDNA, indicated the fact that the splicing occurred more efficiently in each of them. Panel (c) shows that the introduction of the G967A (V323I) mutation into the Luc2 cDNA hardly influenced the luciferase activity (based on comparison between No. 2 and No. 3). On the other hand, in the Luc2 vector in which dystrophin exon 45 is inserted, as the splicing efficiency increases to allow higher incorporation of exon 45 into Luc2, the luciferase activity is expected to decrease due to occurrence of a frameshift in Luc2. Since the background level of the luciferase activity decreased due to the introduction of the G967A (V323I) mutation, highly sensitive detection of low-frequency exon skipping became possible.

Subsequently, in order to investigate whether the expected splicing pattern actually occurs or not, the vectors shown in FIG. 6, Panel (a) were introduced into 293T cells, and mRNA was extracted therefrom, followed by performing reverse transcription and then PCR amplification. As a result of investigation of the cDNA size by gel electrophoresis, the vectors into which the G967A(V323I) mutation was not introduced (lanes 2 and 4) showed a band corresponding to the non-spliced transcript with high intensity. On the other hand, it could be confirmed that splicing with the expected size occurred in almost the entire transcripts from the vectors into which the G967A(V323I) mutation was introduced (lanes 3 and 5) (FIG. 6, Panel (b)). Further, according to the result of investigation of the luciferase activity of each vector, the insertion of the intron sequence or the introduction of the G967A(V323I) mutation hardly caused changes. On the other hand, in the cases where the human exon 45 sequence was inserted, the vector without the G967A (V323I) mutation showed some luciferase activity through the pseudo-splicing donor, and therefore exhibited a high background level. In contrast, by the introduction of the G967A(V323I) mutation, the Luc cDNA sequence containing human exon 45 became the majority, and therefore only very low luciferase activity was found (FIG. 6, Panel (c)).

Figure 7:
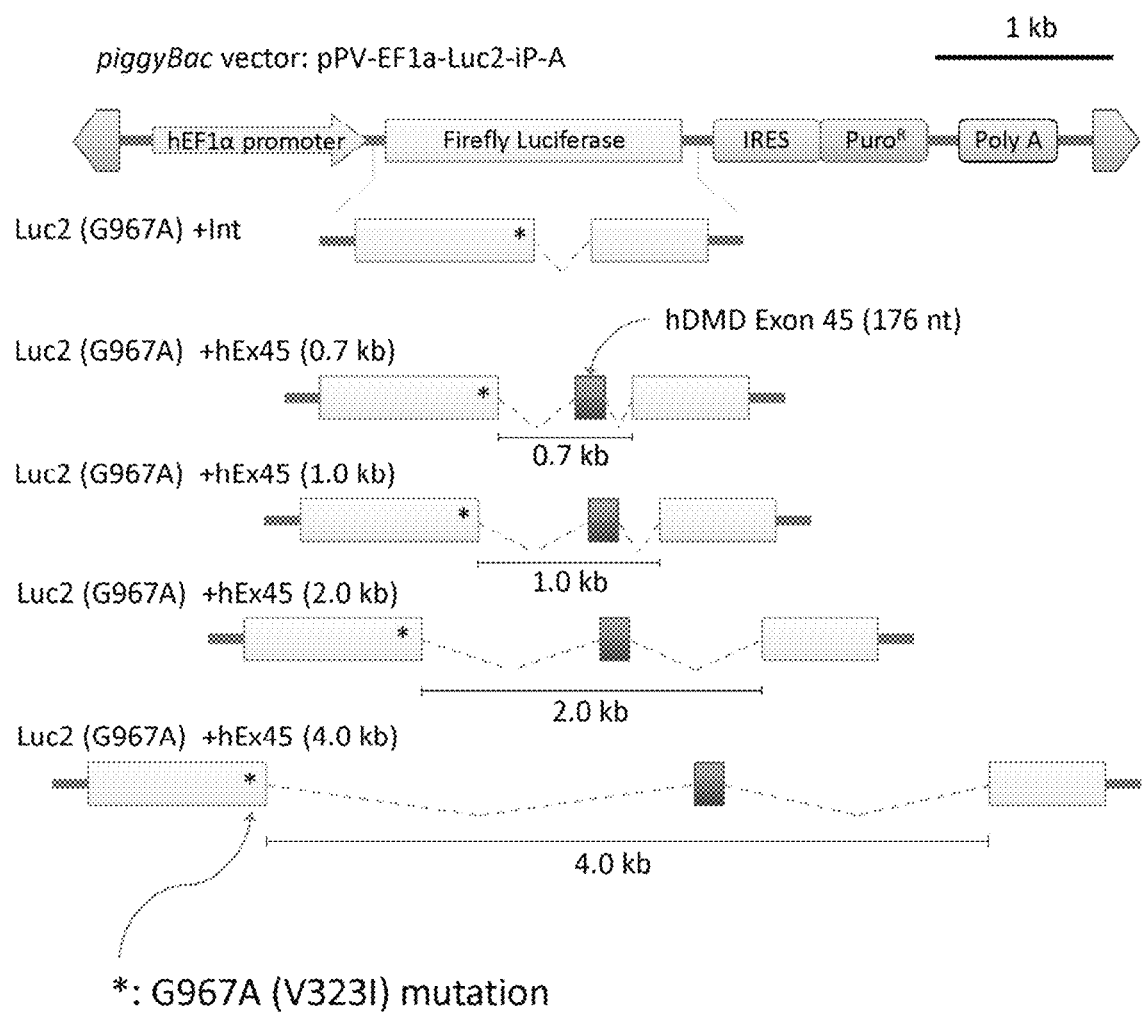
FIG. 7 shows vectors having various lengths which were constructed for the purpose of investigation of the influence of the lengths of the introns before and after exon 45 on the splicing. A luciferase reporter is loaded on the piggyBac vector, and, by introducing this vector together with a piggyBac transposase expression vector, stable incorporation of the luciferase reporter into the chromosome of the host cell is possible. Further, a puromycin resistance gene is also loaded following IRES so that only cells with the reporter vector introduced can be enriched.
Figure 8A:
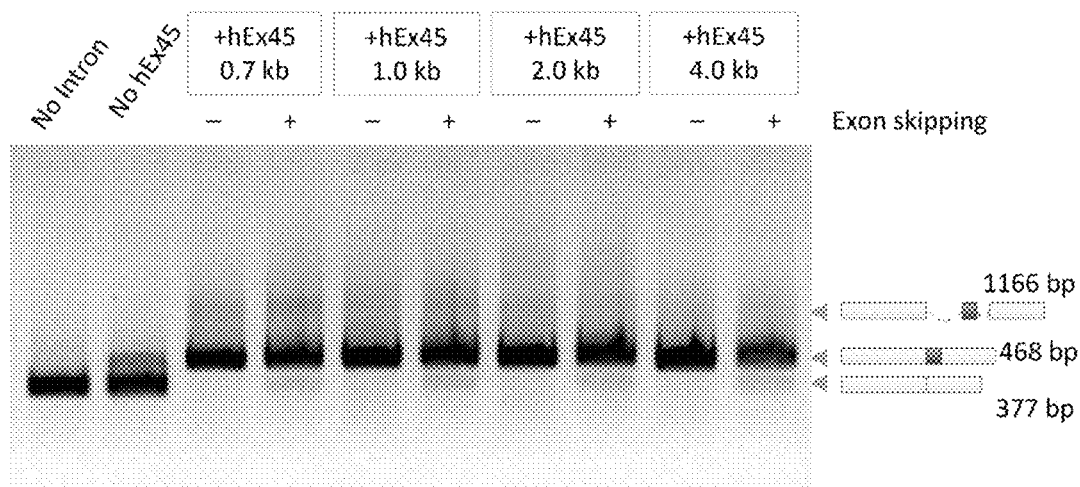
FIG. 8a shows the results of analysis of the splicing pattern carried out by transfecting 293T cells with the exon skipping vectors (Luc2 G967A) of FIG. 7, extracting mRNA from the cells two days later, and then performing PCR analysis. The unspliced band (1166 bp) tended to become weak as the lengths of the introns before and after exon 45 (0.7 to 4.0 kb) increased. However, in all cases, a band indicating efficient splicing (468 bp) was found. Further, gRNA1 and an SpCas9-expressing plasmid were simultaneously introduced to induce exon skipping (exon skipping "+"). As a result, in the reporters with any intron length, a band indicating induction of skipping (377 bp) was found.
Figure 8B:
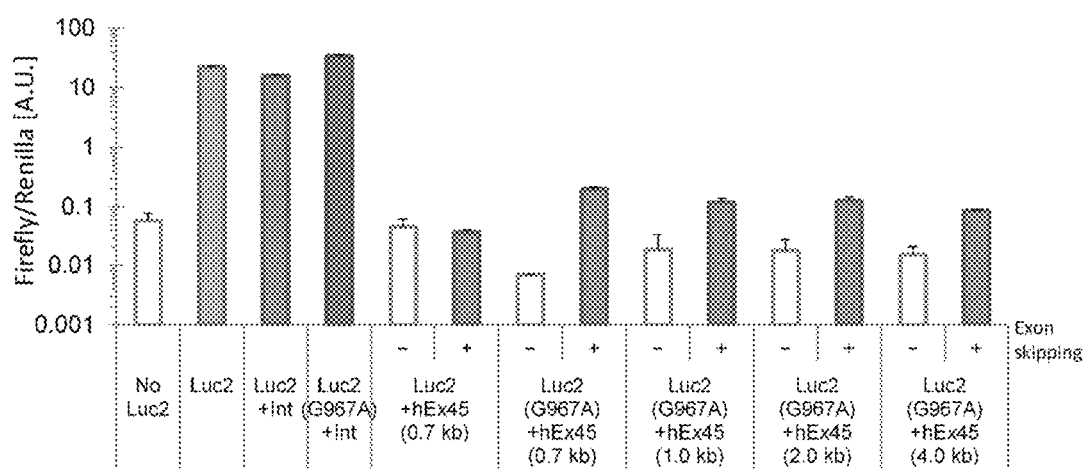
FIG. 8b shows the results of measurement of the induction efficiency of exon skipping, which measurement was carried out by a luciferase assay. Regarding the reporter vector in which the G967A point mutation was not introduced (Luc2+hEx45 (0.7 kb)), the background level was high even without induction of exon skipping, and no difference was found between the values before and after the induction. In contrast, regarding the exon skipping vectors into which the G967A mutation was introduced, exon skipping was induced by introduction of a vector expressing SpCas9 and sgRNA-DMD1, so that increases in the luciferase activity could be found.

Subsequently, analysis of the splicing pattern depending on the lengths of the intron sequences before and after exon 45 was carried out. Vectors were constructed by inserting, other than the originally constructed 0.7-kb sequence, a sequence with a length of 1.0 kb, 2.0 kb, or 4.0 kb (FIG. 7). According to the result of analysis of the splicing patterns of these vectors (FIG. 8a), the vectors mostly showed almost expected splicing patterns (the band of 468 bp), but, as the intron size increased, the band of the residual intron (1166 bp) tended to disappear. On the other hand, as a result of investigation of the luciferase activity, it was found that, as the intron size increases, the introduction activity into the cells decreases, resulting in a rather high background activity. With any of the vectors, an increase in the luciferase activity could be found when exon skipping was induced using CRISPR-sgRNA-DMD1 (FIG. 8b). Thus, the vectors were found to be useful as reporter vectors that enable simple and sensitive measurement.

Figure 9:
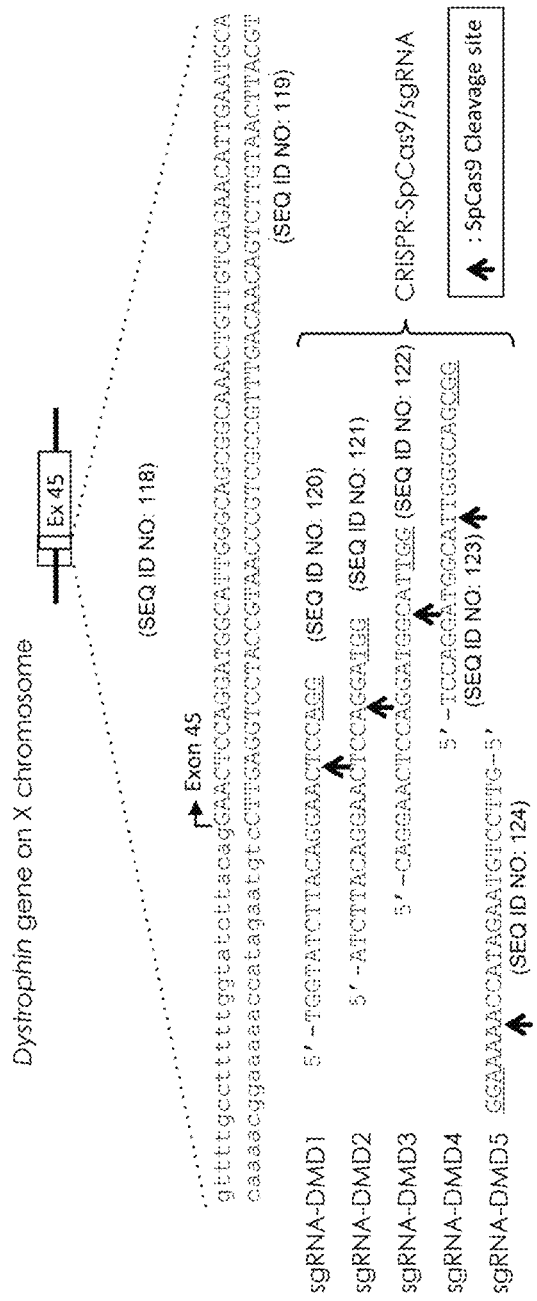
FIG. 9 shows target sequences of CRISPR SpCas9 gRNA for the splice acceptor site of exon 45 in the human dystrophin gene.

In order to induce exon skipping of dystrophin while minimizing the off-target risk, a plurality of gRNAs were designed at the splice acceptor site of exon 45 (FIG. 9), and an SSA (Single Strand Annealing) assay was carried out for the cleavage pattern by an ordinary wild-type SpCas9 and a gRNA, and for cases where a D10A nickase-type SpCas9 and two gRNAs were used in combination. The DNA cleavage activities for the target site were measured. As a result, as shown in FIG. 10, any of five kinds of gRNAs exhibited a high DNA cleavage activity. Further, it was found that, in the double nicking method, the cleavage activity is low when two gRNAs are overlapping, and that induction of efficient DNA cleavage requires the presence of a certain distance.

Subsequently, in order to investigate DNA cleavage patterns obtained under various conditions, the target site was amplified by PCR, and sequence analysis with a next-generation sequencer MiSeq was carried out. As a result, when two gRNAs were designed such that they were arranged at an appropriate distance in the double nicking method, DNA cleavage patterns with occurrence of deletion between the nicking induction sites of the gRNAs were frequently observed. Thus, it was discovered that, in cases where a splice acceptor sequence, especially the "AG" acceptor sequence, is included in this region, efficient induction of exon skipping is possible (FIG. 11).

For studying gRNA sequences, types of CRISPR (SpCas9, AsCpf1, and the like), and genome editing methods (double-nicking) that enable efficient induction of exon skipping, a study was carried out using the exon skipping reporters developed as described above.

Figure 12:
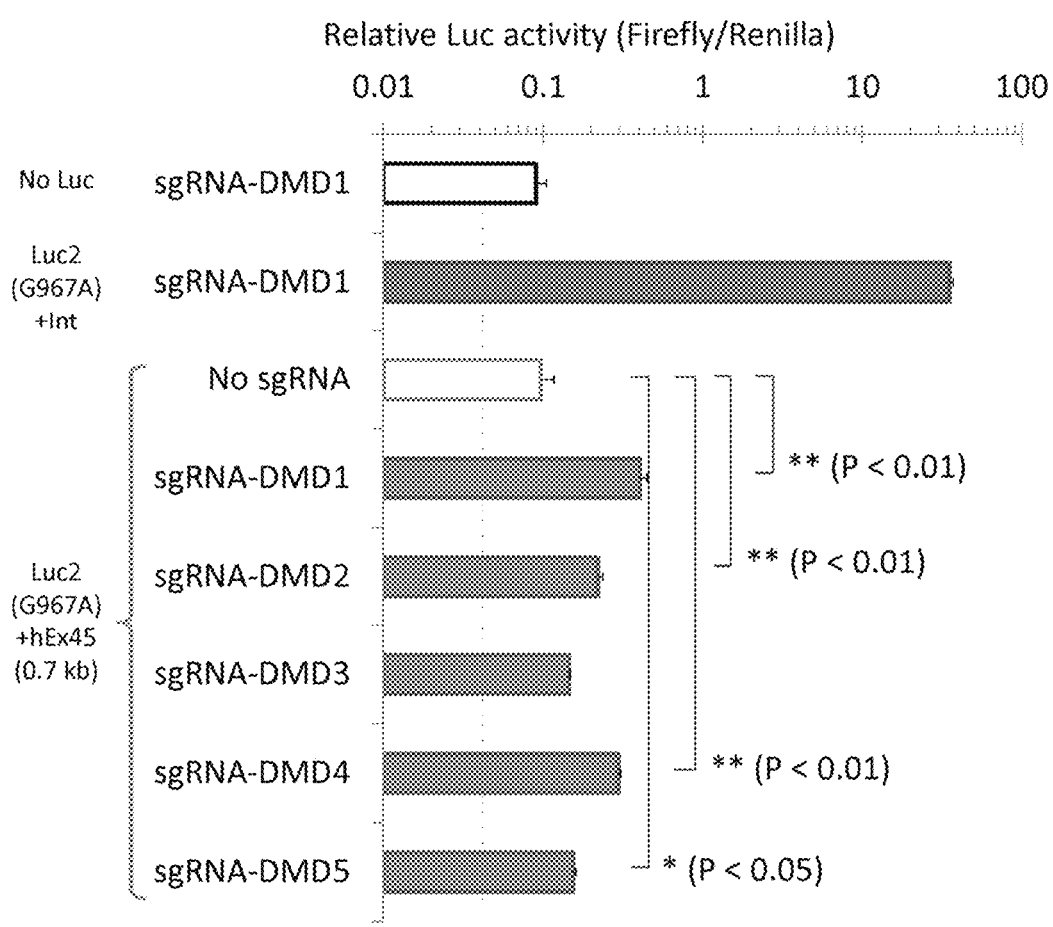
FIG. 12 shows the results of measurement of the exon skipping efficiencies of sgRNA-DMD 1 to 5 in 293T cells using Luc2 (G967A)+hEx45 (0.7 kb) as an exon skipping reporter. As a result, increased luciferase activities were found for sgRNA-DMD1, sgRNA-DMD4, and sgRNA-DMD2 with significant differences at P<0.01 compared to a sample without gRNA.
Figure 14A:
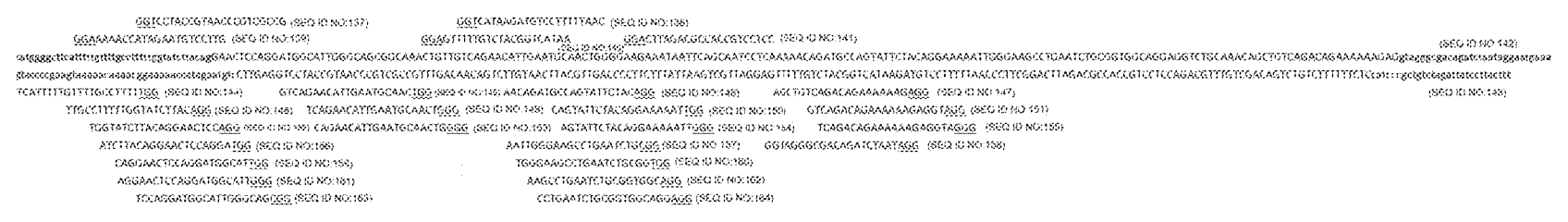
Figure 14C:
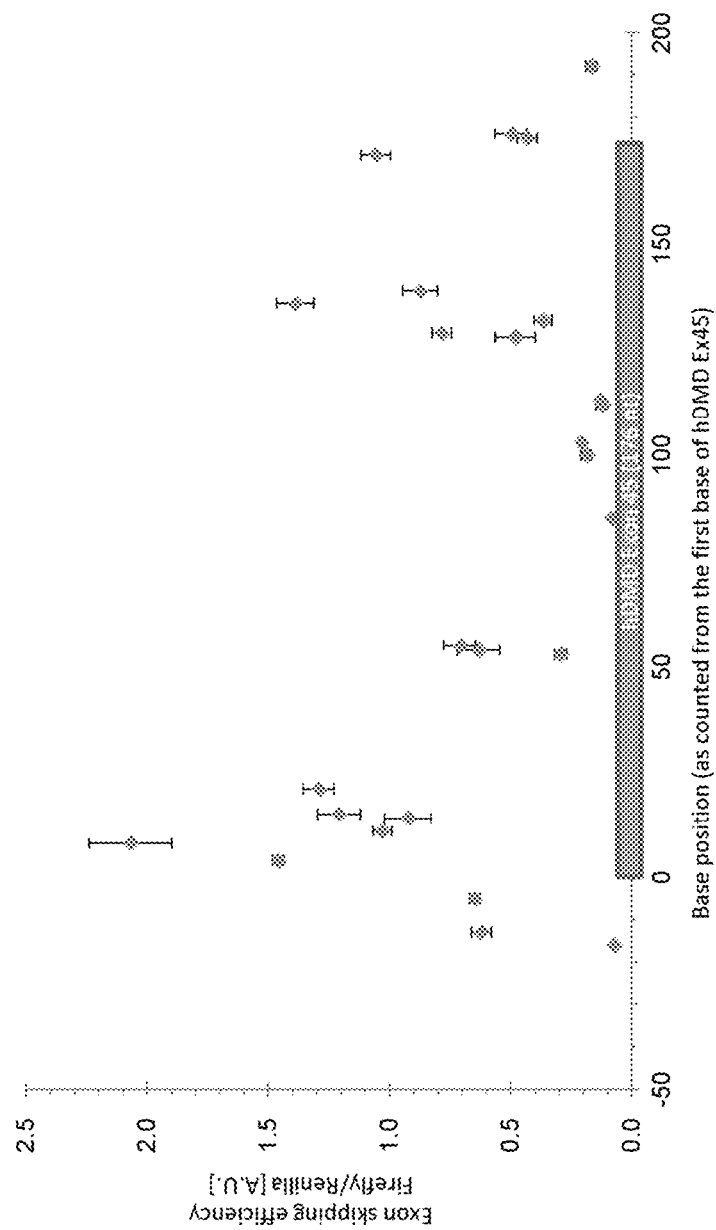
FIG. 14c shows the results of measurement of the exon skipping efficiencies of sgRNA-DMD 1 to 26 in 293T cells using Luc2 (G967A)+hEx45 (0.7 kb) as an exon skipping reporter. As a result, it was found that gRNAs targeting positions near the splice acceptor, and gRNAs targeting positions near the splicing donor, of exon 45 have high exon skipping efficiencies.

As shown in FIG. 12, five kinds of gRNA sequences of SpCas9 were tested, and, as shown in FIGS. 13a to 13d, comparative analysis was carried out for SpCas9, SaCas9, AsCpf1, and the SpCas9 double-nicking method. As shown in FIGS. 14a to 14c, in order to measure the exon skipping efficiency for all sequences that can be designed in human exon 45 (sgRNA sequences including the NGG PAM sequence), 26 kinds of gRNAs were designed (FIG. 14a).

The 26 kinds of gRNAs were introduced into human 293T cells, and the target DNA cleavage activity was measured by a T7E1 assay (FIG. 14b). As a result, although sgRNA-DMD6 showed a low DNA cleavage activity, other gRNAs basically showed cleavage activities of not less than 10%. In view of this, the 26 kinds of gRNAs were subjected to measurement of the exon skipping efficiency in 293T cells using the Luc2 (G967A)+hEx45 (0.7 kb) reporter. As a result, it was found that the gRNA design site and the distance from the splice acceptor or the splicing donor are important for the exon skipping efficiency (FIG. 14c).

Further, seven kinds of gRNAs that individually showed exon skipping activity (DMD #1, 2, 4, 8, 9, 20, and 23) were selected, and arbitrary combinations of two sgRNAs among these were subjected to measurement of the exon skipping efficiency in 293T cells using the Luc2 (G967A)+hEx45 (0.7 kb) reporter. As a result, it was found that the exon skipping efficiency can be further increased by simultaneous introduction of two kinds of gRNAs (FIG. 15).

REFERENCES

1. Li H L, Fujimoto N, Sasakawa N, Shirai S, Ohkame T, Sakuma T, et al. Precise correction of the dystrophin gene in duchenne muscular dystrophy patient induced pluripotent stem cells by TALEN and CRISPR-Cas9. Stem Cell Reports. 2015 Jan. 13; 4(1): 143-54.
2. Mali P, Aach J, Stranges P B, Esvelt K M, Moosburner M, Kosuri S, et al. CAS9 transcriptional activators for target specificity screening and paired nickases for cooperative genome engineering. Nat Biotechnol. 2013 September; 31(9): 833-8.
3. Ran F A, Hsu P D, Lin C-Y, Gootenberg J S, Konermann S, Trevino A E, et al. Double nicking by RNA-guided CRISPR Cas9 for enhanced genome editing specificity. Cell. 2013 Sep. 12; 154(6): 1380-9.
4. Ousterout D G, Kabadi A M, Thakore P I, Majoros W H, Reddy T E, Gersbach C A. Multiplex CRISPR/Cas9-based genome editing for correction of dystrophin mutations that cause Duchenne muscular dystrophy. Nat Commun. 2015; 6: 6244.
5. Iyombe-Engembe J-P, Ouellet D L, Barbeau X, Rousseau J, Chapdelaine P, Lague P, et al. Efficient Restoration of the Dystrophin Gene Reading Frame and Protein Structure in DMD Myoblasts Using the CinDel Method. Mol Ther Nucleic Acids. 2016; 5:e283.
6. Long C, Amoasii L, Mireault A A, McAnally J R, Li H, Sanchez-Ortiz E, et al. Postnatal genome editing partially restores dystrophin expression in a mouse model of muscular dystrophy. Science. 2016 Jan. 22; 351(6271): 400-3.
7. Nelson C E, Hakim C H, Ousterout D G, Thakore P I, Moreb E A, Castellanos Rivera R M, et al. In vivo genome editing improves muscle function in a mouse model of Duchenne muscular dystrophy. Science. 2016 Jan. 22; 351(6271): 403-7.
8. Tabebordbar M, Zhu K, Cheng J K W, Chew W L, Widrick J J, Yan W X, et al. In vivo gene editing in dystrophic mouse muscle and muscle stem cells. Science. 2016 Jan. 22; 351(6271): 407-11.

What is claimed is:

1. A method of skipping a target exon 45 of a human dystrophin gene in a genome, the method comprising using CRISPR-Cas and two or more kinds of guide RNAs, wherein each guide RNA contains a spacer sequence configured to position the site of cleavage by the CRISPR-Cas within 80 bases from the splice acceptor site immediately before the target exon or the splice donor site immediately after the target exon, wherein the CRISPR-Cas is Cas9, and wherein at least one guide RNA contains a spacer sequence having the base sequence of bases from 17th to 36th in the base sequence of SEQ ID NO:17.

2. The method according to claim 1, wherein the CRISPR-Cas is a nickase-modified Cas containing a substitution in the nuclease activity residue in the RuvC domain, and wherein a guide RNA for the sense strand and a guide RNA for the antisense strand of the human dystrophin gene are used, the guide RNAs containing spacer sequences for positioning the cleavage site in the sense strand of the human dystrophin gene and the cleavage site in the antisense strand of the human dystrophin gene within 80 bases from the splice acceptor site immediately before the target exon or the splice donor site immediately after the target exon.

3. The method according to claim 1, wherein the Cas9 is derived from *Streptococcus pyogenes*, or derived from *Staphylococcus aureus*.

4. The method according to claim 1, wherein at least one guide RNA contains a spacer sequence having the base sequence of bases from $17^{th}$ to $36^{th}$ in the base sequence of any of SEQ ID NOs:18 to 42, the base sequence of bases from $17^{th}$ to $39^{th}$ in the base sequence of any of SEQ ID NOs:44 to 45, or the base sequence of bases from $24^{th}$ to $43^{rd}$ in the base sequence of any of SEQ ID NOs:50 to 53.

5. A reagent for skipping a target exon 45 of a human dystrophin gene in a genome, the reagent comprising CRISPR-Cas and two or more kinds of guide RNAs, wherein each guide RNA contains a spacer sequence configured to position the site of cleavage by the CRISPR-Cas within 80 bases from the splice acceptor site immediately before the target exon or the splice donor site immediately after the target exon, wherein the CRISPR-Cas is Cas9, and wherein at least one guide RNA contains a spacer sequence having the base sequence of bases from 17th to 36th in the base sequence of SEQ ID NO:17.

6. A method of skipping a target exon 45 of a human dystrophin gene in a genome, the method comprising using CRISPR-Cas and two or more kinds of guide RNAs, wherein each guide RNA contains a spacer sequence configured to position the site of cleavage by the CRISPR-Cas within 80 bases from the splice acceptor site immediately before the target exon or the splice donor site immediately after the target exon, wherein the CRISPR-Cas is Cas9, and wherein the spacer sequences of the two or more kinds of guide RNA include the combinations of sgRNA-DMD1 (the base sequence of bases from $17^{th}$ to $36^{th}$ in SEQ ID NO:17), sgRNA-DMD2 (the base sequence of bases from $17^{th}$ to $36^{th}$ in SEQ ID NO:18), sgRNA-DMD4 (the base sequence of bases from $17^{th}$ to $36^{th}$ in SEQ ID NO:20), sgRNA-DMD8 (the base sequence of bases from $17^{th}$ to $36^{th}$ in SEQ ID NO:24), or sgRNA-DMD9 (the base sequence of bases from $17^{th}$ to $36^{th}$ in SEQ ID NO:25) with sgRNA-DMD23 (the base sequence of bases from $17^{th}$ to $36^{th}$ in SEQ ID NO:39) or sgRNA-DMD20 (the base sequence of bases from $17^{th}$ to $36^{th}$ in SEQ ID NO:36).

7. The method according to claim 6, wherein the spacer sequences of the two or more kinds of guide RNA include the combinations of sgRNA-DMD1 (the base sequence of bases from $17^{th}$ to $36^{th}$ in SEQ ID NO:17), sgRNA-DMD2 (the base sequence of bases from $17^{th}$ to $36^{th}$ in SEQ ID NO:18), sgRNA-DMD4 (the base sequence of bases from $17^{th}$ to $36^{th}$ in SEQ ID NO:20), sgRNA-DMD8 (the base sequence of bases from $17^{th}$ to $36^{th}$ in SEQ ID NO:24), or sgRNA-DMD9 (the base sequence of bases from $17^{th}$ to $36^{th}$ in SEQ ID NO:25) with sgRNA-DMD23 (the base sequence of bases from $17^{th}$ to $36^{th}$ in SEQ ID NO:39).

8. A reagent for skipping a target exon 45 of a human dystrophin gene in a genome, the reagent comprising CRISPR-Cas and two or more kinds of guide RNAs, wherein each guide RNA contains a spacer sequence configured to position the site of cleavage by the CRISPR-Cas within 80 bases from the splice acceptor site immediately before the target exon or the splice donor site immediately after the target exon, wherein the CRISPR-Cas is Cas9, and wherein the spacer sequences of the two or more kinds of guide RNA include the combinations of sgRNA-DMD1 (the base sequence of bases from $17^{th}$ to $36^{th}$ in SEQ ID NO:17), sgRNA-DMD2 (the base sequence of bases from $17^{th}$ to $36^{th}$ in SEQ ID NO:18), sgRNA-DMD4 (the base sequence of bases from $17^{th}$ to $36^{th}$ in SEQ ID NO:20), sgRNA-DMD8 (the base sequence of bases from $17^{th}$ to $36^{th}$ in SEQ ID NO:24), or sgRNA-DMD9 (the base sequence of bases from $17^{th}$ to $36^{th}$ in SEQ ID NO:25) with sgRNA-DMD23 (the base sequence of bases from $17^{th}$ to $36^{th}$ in SEQ ID NO:39) or sgRNA-DMD20 (the base sequence of bases from $17^{th}$ to $36^{th}$ in SEQ ID NO:36).

9. The reagent according to claim 8, wherein the spacer sequences of the two or more kinds of guide RNA include the combinations of sgRNA-DMD1 (the base sequence of bases from $17^{th}$ to $36^{th}$ in SEQ ID NO:17), sgRNA-DMD2 (the base sequence of bases from $17^{th}$ to $36^{th}$ in SEQ ID NO:18), sgRNA-DMD4 (the base sequence of bases from $17^{th}$ to $36^{th}$ in SEQ ID NO:20), sgRNA-DMD8 (the base sequence of bases from $17^{th}$ to $36^{th}$ in SEQ ID NO:24), or sgRNA-DMD9 (the base sequence of bases from $17^{th}$ to $36^{th}$ in SEQ ID NO:25) with sgRNA-DMD23 (the base sequence of bases from $17^{th}$ to $36^{th}$ in SEQ ID NO:39).

* * * * *